United States Patent [19]

Zahler et al.

[11] Patent Number: 4,576,749

[45] Date of Patent: Mar. 18, 1986

[54] 3-ACYLAMINO-1-CARBOXYMETHYLAMINOCARBONYL-2-AZETIDINONES

[75] Inventors: Robert Zahler, Princeton; William H. Koster, East Amwell Township, Hunterdon County; William A. Slusarchyk, Belle Mead, all of N.J.

[73] Assignee: E. R. Squibb & Sons, Inc., Princeton, N.J.

[21] Appl. No.: 599,841

[22] Filed: Apr. 13, 1984

Related U.S. Application Data

[63] Continuation-in-part of Ser. No. 538,719, Oct. 3, 1983, abandoned.

[51] Int. Cl.⁴ .................. C07D 205/08; C07D 403/12; C07D 401/12; A61K 31/395

[52] U.S. Cl. .................. 260/239 A; 544/311; 544/312; 260/239.3 R; 544/316; 544/317; 260/245.4; 544/319; 544/320; 260/330.3; 544/321; 544/322; 260/330.9; 544/323; 544/324; 514/210; 544/325; 544/326; 544/54; 544/327; 544/331; 544/96; 544/332; 544/333; 544/111; 544/334; 544/335; 544/121; 544/359; 544/364; 544/122; 544/366; 544/369; 544/123; 544/370; 544/371; 544/124; 544/372; 544/374; 544/129; 544/379; 546/187; 544/130; 546/208; 546/256; 544/131; 546/275; 544/132; 544/133; 544/134; 544/137; 544/139; 544/140; 544/141; 544/146; 544/147; 544/182; 544/215; 544/279; 544/295; 544/296; 544/300; 544/301; 544/310

[58] Field of Search ......... 260/239 A, 245.4, 239.3 R, 260/330.3, 330.9; 544/54, 96, 111, 121, 122, 123, 124, 129, 130, 131, 132, 133, 134, 137, 139, 140, 141, 146, 147, 182, 215, 279, 295, 296, 300, 301, 310, 311, 312, 316, 317, 319, 320, 321, 322, 323, 324, 325, 326, 327, 331, 332, 333, 334, 335, 359, 364, 366, 369, 370, 371, 372, 374, 379; 546/187, 208, 256, 275

[56] References Cited

PUBLICATIONS

"The Synthesis of Peptide β-Lactams as Potential Protease Inhibitors", Wharton et al., Journal of Chemical Society, Perkin Transcripts, 1984, pp. 29–39.

Primary Examiner—Mark L. Berch
Attorney, Agent, or Firm—Lawrence S. Levinson; Donald J. Barrack

[57] ABSTRACT

Antibacterial activity is exhibited by 2-azetidinones having a 3-acylamino substituent and a 1-substituent of the formula

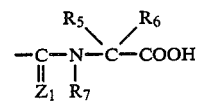

(or a salt or ester thereof).

32 Claims, No Drawings

3-ACYLAMINO-1-CARBOXYME-THYLAMINOCARBONYL-2-AZETIDINONES

RELATED APPLICATIONS

This application is a continuation-in-part of copending U.S. patent application Ser. No. 538,719, filed Oct. 3, 1983, now abandoned.

U.S. patent application Ser. No. 515,727, filed July 21, 1983, discloses β-lactam antibiotics and intermediates comprising a 2-azetidinone having in the 1-position a group of the formula

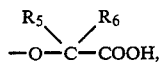

and salts and esters thereof, wherein $R_5$ and $R_6$ are as defined hereinafter.

U.S. patent application Ser. No. 252,672, filed Apr. 1, 1982, now abandoned discloses β-lactam antibiotics and intermediates comprising a 2-azetidinone having in the 1-position a group of the formula

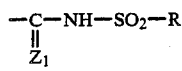

wherein $Z_1$ is as defined hereinafter and R is one of the organic substituents recited therein.

BRIEF DESCRIPTION OF THE INVENTION

Compounds having the formula

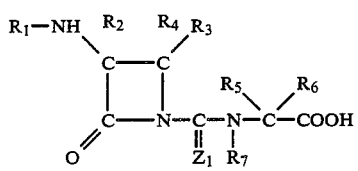

I and esters and salts thereof, have antibacterial activity. In formula I, and throughout the specification, the symbols are as defined below.

$Z_1$ is oxygen or sulfur;

$R_1$ is acyl;

$R_2$ is hydrogen or methoxy;

$R_3$ and $R_4$ are the same or different and each is hydrogen, alkyl, alkenyl, alkynyl, cycloalkyl, phenyl, substituted phenyl or a 4, 5, 6 or 7-membered heterocycle (referred to hereinafter as $R_x$) or one of $R_3$ and $R_4$ is hydrogen and the other is azido, halomethyl, dihalomethyl, trihalomethyl, alkoxycarbonyl, 2-phenylethenyl, 2-phenylethynyl, carboxy, —$CH_2X_1$ [wherein $X_1$ is azido, amino (—$NH_2$), hydroxy, carboxy, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano, —S—$X_2$, or —O—$X_2$ (wherein $X_2$, is as hereinafter defined)], —S—$X_2$ or —O—$X_2$ [wherein $X_2$ is alkyl, phenyl, or substituted phenyl],

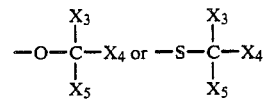

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxy, alkoxycarbonyl, aminocarbonyl

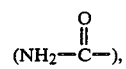

(substituted amino)carbonyl, or cyano (—C≡N)], or

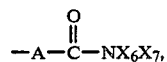

(wherein A is —CH=CH—, —$(CH_2)_n$—, —$CH_2$—O—, —$CH_2$—NH—, —$CH_2$—S—$CH_2$—, or —$CH_2$—O—$CH_2$—, n is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, or 6-membered nitrogen containing heterocycle);

$R_5$ and $R_6$ are the same or different and each is hydrogen, alkyl, alkenyl, alkynyl, phenyl, substituted phenyl, cycloalkyl or $R_x$, or $R_5$ and $R_6$ together with the carbon atom to which they are attached are cycloalkyl, or one of $R_5$ and $R_6$ is hydrogen and the other is halomethyl, dihalomethyl, trihalomethyl, alkoxycarbonyl, alkenyl, alkynyl, 2-phenylethenyl, 2-phenylethynyl, carboxy, —$CH_2$—$X_1$, or

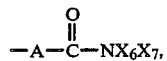

or $R_6$ is hydrogen and $R_5$ together with $R_7$ and the atoms to which they are attached form a 4, 5, or 6-membered nitrogen containing heterocycle; and $R_7$ is hydrogen, alkyl, phenyl, substituted phenyl, cycloalkyl, $R_x$,

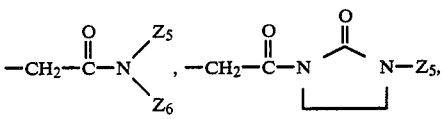

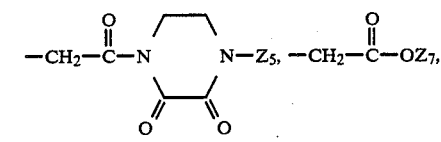

or —(CH$_2$)$_n$—Z$_3$ wherein n is 2, 3 or 4 and Z$_3$ is azido, —NZ$_5$Z$_6$, halogen, hydroxy,

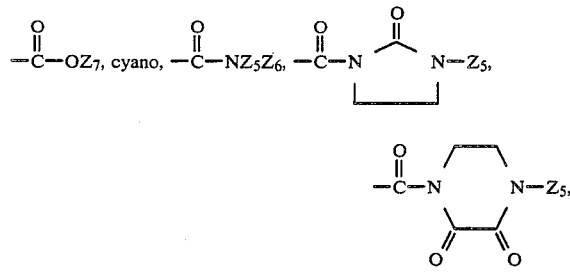

alkanoyloxy, alkoxy, phenyloxy, (substituted phenyl)oxy, R$_x$—oxy, mercapto, alkylthio, phenylthio, (substituted phenyl)thio, alkylsulfinyl, alkylsulfonyl,

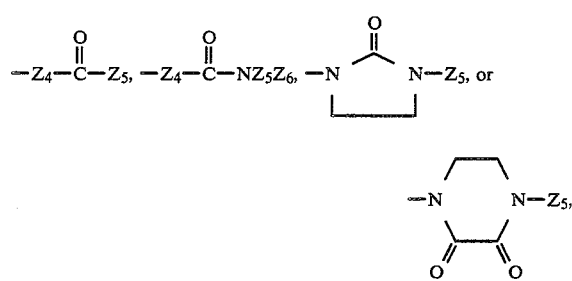

wherein Z$_4$ is oxygen, sulfur or

Z$_5$ is hydrogen, alkyl, phenyl, substituted phenyl, phenylalkyl or (substituted phenyl)alkyl, Z$_6$ is hydrogen, alkyl, phenyl, substituted phenyl, phenylalkyl, (substituted phenyl)alkyl, alkanoyl, phenylcarbonyl, or (substituted phenyl)carbonyl, and Z$_7$ is hydrogen, alkyl, phenyl or substituted phenyl.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one or more (preferably 1, 2 or 3) azido, amino (—NH$_2$), halogen, hydroxy, carboxy, cyano, alkoxycarbonyl, aminocarbonyl, alkanoyloxy, alkoxy, phenyloxy, (substituted phenyl)oxy, R$_x$—oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "protected carboxy" refers to a carboxy group which has been esterified with a conventional acid protecting group. These groups are well known in the art; see, for example, U.S. Pat. No. 4,144,333, issued Mar. 13, 1979. The preferred protected carboxy groups are benzyl, benzhydryl, t-butyl, and p-nitrobenzyl esters.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4,5,6 or 7-membered heterocycle" (referred to as "R$_x$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

benzylideneamino and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NZ$_8$Z$_9$ wherein Z$_8$ is hydrogen, alkyl, phenyl, substituted phenyl, phenylalkyl or (substituted phenyl)alkyl, and Z$_9$ is alkyl, phenyl, substituted phenyl, phenylalkyl, (substituted phenyl)alkyl, hydroxy, cyano, alkoxy, phenylalkoxy, or amino (—NH$_2$).

The expression "a 4, 5, or 6-membered nitrogen containing heterocycle" refers to 1-pyrrolidinyl, Δ$^3$-pyrrolin-1-yl, 1-azetidinyl, 1-piperidinyl, Δ$^3$-piperidein-1-yl, Δ$^4$-piperidein-1-yl, 3-oxazolidinyl, 3-thiazolidinyl, 1-imidazolidinyl, 4-thiomorpholinyl, 4-morpholinyl, 1-piperazinyl, 1-hexahydropyrimidinyl, tetrahydro-2H-

1,3-thiazin-3-yl, tetrahydro-2H-1,3-oxazin-3-yl, 3-thiazolidinyl, 1-oxide, 3-thiazolidinyl,1,1-dioxide, 4-thiomorpholinyl,1-oxide, 4-thiomorpholinyl,1,1-dioxide, tetrahydro-2H-1,3-thiazin-3-yl,1-oxide, tetrahydro-2H-1,3-thiazin-3-yl,1,1-dioxide, or one of the above groups substituted with one or more (preferably 1, 2 or 3) oxo, halogen, hydroxy, amino, cyano, trifluoromethyl, alkyl of 1 to 4 carbon atoms, alkoxy of 1 to 4 carbon atoms, alkylsulfonyl, phenyl, substituted phenyl, azido, carboxy, aminocarbonyl, $OZ_{10}$, $NHZ_{10}$, or $SZ_{10}$ where $Z_{10}$ is alkanoyl, aminocarbonyl, aminosulfonyl, phenylcarbonyl, (substituted phenyl)carbonyl, alkyl, substituted alkyl, phenyl or substituted phenyl.

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, Cephalosporins and Penicillins, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, British Pat. No. 1,348,894, published Mar. 27, 1974, and European patent application No. 75,805, published Apr. 6, 1983. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

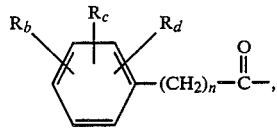

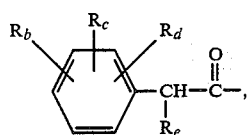

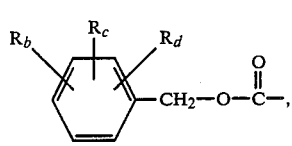

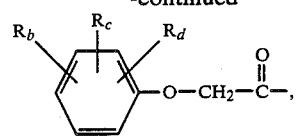

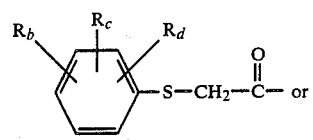

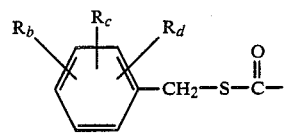

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

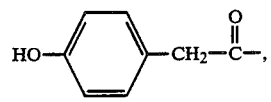

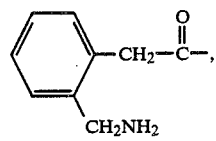

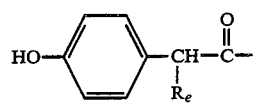

($R_e$ is preferably a carboxyl salt or sulfo salt) and

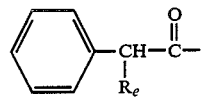

($R_e$ is preferably a carboxyl salt or sulfo salt).

(c) Heteroaromatic groups having the formula

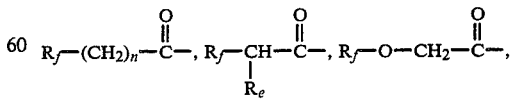

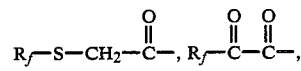

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifuoromethyl, alkyl of 1 to 4 carbon atoms, alkoxy of 1 to 4 carbon atoms, or

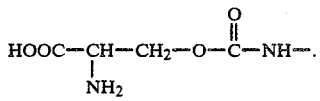

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

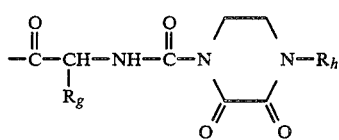

wherein $R_g$ is an aromatic group (including carbocyclic aromatics such as those of the formula

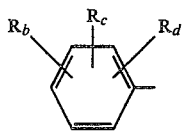

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

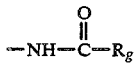

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula

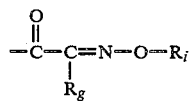

wherein $R_g$ is as defined above and $R_i$ is hydrogen, alkyl, cycloalkyl, alkylaminocarbonyl, arylaminocarbonyl (i.e.,

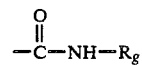

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl substituents, 1-piperazinylcarbonyl, or 4-methyl-1-piperazinylcarbonyl).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

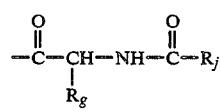

wherein $R_g$ is as defined above and $R_j$ is

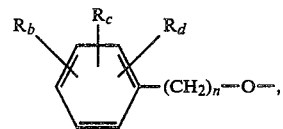

amino, alkylamino, (cyanoalkyl)amino, amido, alkylamido, (cyanoalkyl)amido,

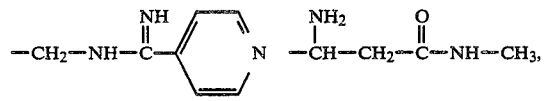

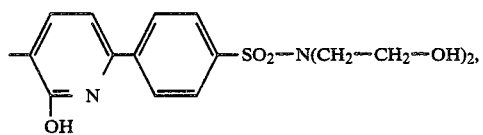

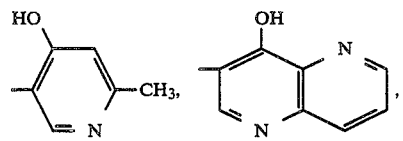

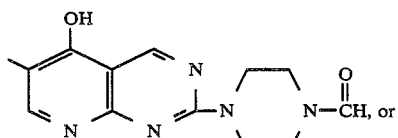

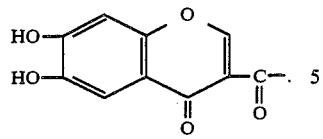

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

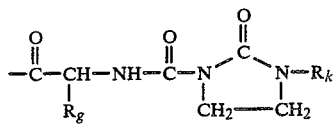

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The terms "salt" and "salts" refer to basic salts formed with inorganic and organic bases. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, pharmacetically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

As set forth throughout the specification, β-lactams having in the 1-position an ester of the group

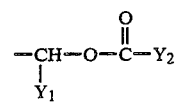

are contemplated as an integral part of this invention. Exemplary esters include alkyl, alkenyl, alkynyl, cycloalkyl, (cycloalkyl)alkyl, $R_x$-alkyl, trialkylsilylalkyl, mono-, di- or trihaloalkyl, hydroxyalkyl, alkoxyalkyl, carboxyalkyl, alkoxycarbonylalkyl, diphenylmethoxycarbonylalkyl, carbamoylalkyl, alkylcarbamoylalkyl, dialkylcarbamoylalkyl, indanyl, phenyl, substituted phenyl, phenylalkyl, (substituted phenyl)alkyl, $R_x$-carbonylalkyl, $$-CH-O-\overset{O}{\underset{}{\overset{\|}{C}}}-Y_2$$
$$\quad |$$
$$\quad Y_1$$

[wherein $Y_1$ is hydrogen, alkyl or phenyl and $Y_2$ is hydrogen, alkyl, cycloalkyl, (cycloalkyl)oxy, phenyl, or alkoxy, or together $Y_1$ and $Y_2$ are —(CH$_2$)$_2$—, —(CH$_2$)$_3$—, —CH=CH—, or

[benzene ring diagram], and

[cyclic carbonate diagram with —CH—Y$_1$, Y$_1$]

esters.

Hydrolyzable esters are those esters that can be hydrolyzed in vivo to give the parent carboxylic acid product; they exhibit the antibiotic activity of the parent carboxylic acid. Non-hydrolyzable esters (esters that do not hydrolze in vivo to the parent carboxylic acid) are contemplated for use in this invention as intermediates; some of them are also active as antibiotics.

β-Lactams having a

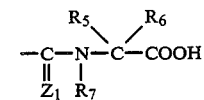

substituent (or an ester or salt thereof) in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins, (e.g., cephamycin C).

With respect to the preferred β-lactams of formula I, the structural formulas have been drawn to show the stereochemistry at the chiral center in the 3-position.

Also included within the scope of this invention are racemic mixtures which contain the above-described β-lactams.

DETAILED DESCRIPTION OF THE INVENTION

The β-lactams of formula I, and esters and salts thereof, have activity against a range of gram-negative and gram-positive organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The products of formula I can be prepared from a 3-protected amino-2-azetidinone having the formula

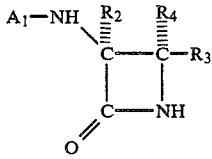

wherein the symbol "$A_1$" represents an amino protecting group (e.g., t-butoxycarbonyl, benzyloxycarbonyl, o-nitrophenylsulfenyl, etc.).

Those products of formula I wherein $R_7$ is hydrogen can be prepared by reacting a compound of formula II with an isocyanate, or thioisocyanate, having the formula

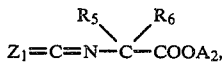

wherein the symbol "$A_2$" represents a carboxyl protecting group. The reaction proceeds by the sequential addition of a strong base (e.g., an alkyl lithium) to a compound of formula II followed by the addition of a compound of formula III, and after aqueous workup yields a compound having the formula

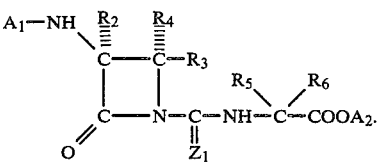

Alternatively, if $Z_1$ is oxygen, the reaction proceeds in the absence of base at elevated temperatures.

Those products of formula I wherein $R_7$ is as defined above, but no hydrogen (this subgenus is referred to hereinafter as $R_7'$) can be prepared by reacting a compound of formula II with a compound having the formula

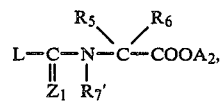

wherein L is a leaving group such as a halogen or imidazole. The reaction proceeds in the presence of a base (such as triethylamine), and a catalytic amount of 4-dimethylaminopyridine, and yields a compound having the formula

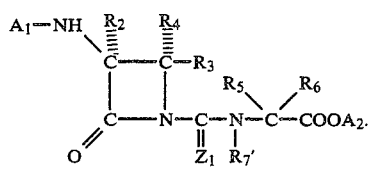

Compounds of formula V can be prepared by reacting a compound having the formula

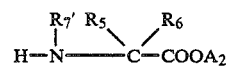

with phosgene or thiophosgene in the presence of base (such as triethylamine or pyridine).

Alternatively, an intermediate of formula VI can be prepared by reacting a compound of formula II with phosgene or thiophosgene in the presence of a base (such as triethylamine) followed by the addition of a compound of formula VII in the presence of a base (such as triethylamine).

A compound of formula I can be prepared from a corresponding compound of formula IV or VI by (i) Removing the $A_1$ and $A_2$ protecting groups simultaneously to obtain a compound having the formula

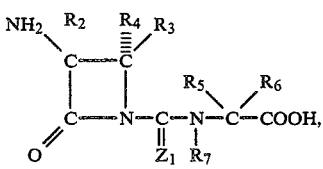

or a salt thereof, and then acylating the compound of formula VIII.

(ii) Removing the $A_2$ protecting, then removing the $A_1$ protecting group, to obtain a compound of formula VIII, or a salt thereof, and then acylating the compound of formula VIII.

(iii) Removing the $A_1$ protecting group to obtain a compound having the formula

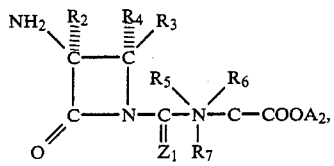

acylating the intermediate of formula IX, and then removing the A₂ protecting group.

The deprotection reactions can be run using art-recognized techniques. If, for example, the protecting group is t-butoxycarbonyl, trifluoroacetic acid can be used to deprotect the amino group. If the protecting group is benzyloxycarbonyl, catalytic (e.g., palladium on charcoal) hydrogenation can be used. If the protecting group is o-nitrophenylsulfenyl, p-toluenesulfonic acid can be used in combination with p-thiocresol. Alternatively, a compound of formula IV or VI can be reacted with N-methyl-N-trimethylsilyl-trifluoroacetamide (MSTFA) and a silane such as iodotrimethylsilane to cleave the "A₁" and "A₂" groups (e.g., when A₁ is t-butoxycarbonyl or benzyloxycarbonyl and A₂ is alkyl or cycloalkyl) and yield the corresponding 3-trimethylsilylamino compound which can then be acylated.

The acylation reactions can also be run using art-recognized techniques. Exemplary techniques include reaction with a carboxylic acid ($R_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reaction intermediate in situ such as N-hydroxybenzotriazole or N-hydroxysuccinimide. In those instances wherein the acyl group ($R_1$) contains reactive functionality (such as amino or carboxyl groups) it may be necessary to first protect these functional groups, then carry out the acylation reaction, and finally deprotect the resulting product.

When preparing an ester of a compound of formula I, it is also possible to choose the "A₂" group to correspond to the desired ester group. This avoids the need for deprotecting and then re-esterifying the carboxyl group.

Methodology for the preparation of the starting 2-azetidinones of formula II is described in United Kingdom patent application No. 2,071,650, published Sept. 23, 1981. These azetidinones are obtainable using any one of numerous procedures.

Reacting an olefin having the formula

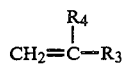

with a halosulfonylisocyanate (preferably chlorosulfonylisocyanate) having the formula

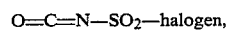

yields an azetidinone having the formula

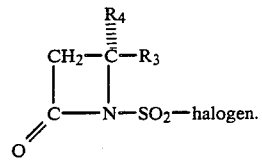

Reductive hydrolysis of an azetidinone of formula XII yields an N-unsubstituted β-lactam having the formula

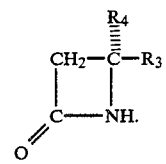

For a more detailed description of the above-described reaction sequence, reference can be made to the literature; see, for example, Chem. Soc. Rev., 5, 181 (1976) and J. Org. Chem., 35, 2043 (1970).

An azido group can be introduced in the 3-position of an azetidinone of formula XIII by reaction of the compound with an arylsulfonyl azide (such as toluenesulfonyl azide) to obtain an azetidinone having the formula

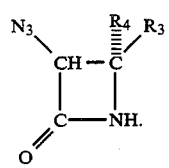

The reaction proceeds best by first protecting the azetidinone nitrogen with a silyl residue (e.g., t-butyldimethylsilyl, or t-butyldiphenylsilyl), then generating the anion at the 3-position of the nucleus with a strong organic base (e.g., lithium diisopropylamine) at a low temperature, and then treating the anion with toluenesulfonyl azide. The resulting intermediate is quenched with trimethylsilyl chloride, and subsequent acid hydrolysis or fluoride solvolysis of the N-protecting group yields the compound of formula XIV.

A 3-azido-2-azetidinone of formula XIV wherein $R_4$ is hydrogen can also be prepared by first reacting a primary amine having the formula

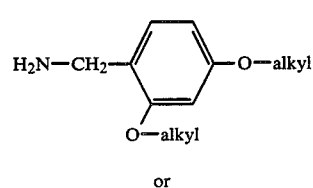

or

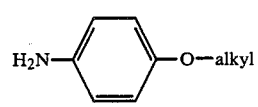

with an aldehyde having the formula

 XVII (or a hemiacetal) to yield the corresponding Schiff base. A [2+2] cycloaddition reaction of the Schiff base with an activated form of α-azidoacetic acid yields a 3-azido-2-azetidinone having the formula

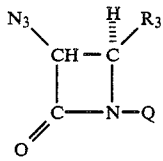 XVIII wherein Q is

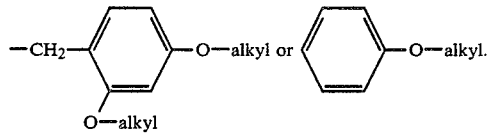

Oxidative removal of the 1-substituent yields the corresponding compound having the formula

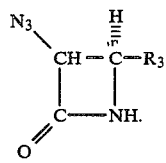 XIX

A 3-azido-2-azetidinone of formula XIV or XVIII can be reduced to the corresponding 3-amino-2-azetidinone having the formula

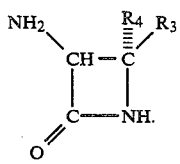 XX

The reduction can be accomplished by catalytic (e.g., palladium on charcoal, or platinum oxide) hydrogenation or with reducing agents such as zinc or triphenylphosphine. A 3-amino-2-azetidinone can be converted to a corresponding 3-protected amino-2-azetidinone of formula II using art-recognized techniques.

A compound of formula II wherein $R_3$ is hydrogen can also be obtained using a procedure analogous to that described above for the preparation of a 3-azido-2-azetidinone wherein $R_3$ is hydrogen. In place of an activated form of α-azidoacetic acid, an activated form of α-phthalimidoacetic acid is used, yielding a compound having the formula

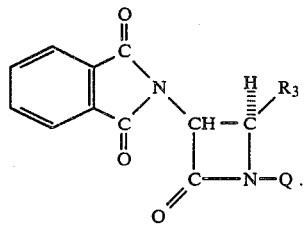 XXI

Treatment of a compound of formula XXI with base yields the corresponding 4α compound having the formula

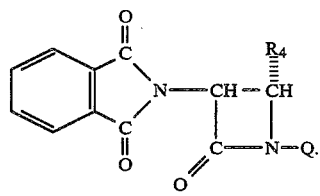 XXII

Reaction of a compound of formula XXI or XXII with a reagent such as methyl hydrazine (to cleave the phthaloyl group), followed by the introduction of a protecting group on the 3-nitrogen substituent, and oxidative removal of the 1-protecting group will yield a compound of formula II wherein $R_2$ and $R_4$ are hydrogen.

The starting 2-azetidinones of formula II wherein $R_2$ is methoxy can be prepared by methoxylating the corresponding non-methoxylated compound of formula II. Chlorination of a nonmethyoxylated compound of formula II yields a compound having the formula

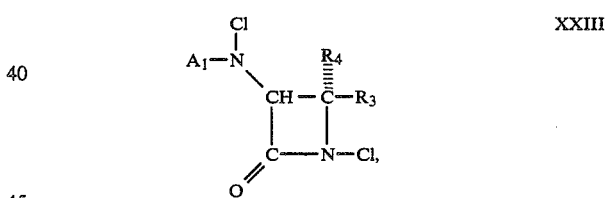 XXIII and can be accomplished by reaction of a compound of formula II with a reagent such as t-butyl hypochlorite, sodium hypochlorite, chlorine or other reagent useful for N-chlorinating amides. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of a compound of formula XXIII with a methoxylating agent, e.g., an alkali metal methoxide, and subsequently adding a reducing agent such as trimethylphosphite, yields a compound having the formula

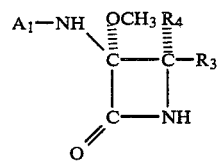 XXIV in combination with its enantiomers.

Additional methodology for the preparation of the starting 2-azetidinones of formula II is described in United Kingdom patent application No. 2,071,650, published Sept. 23, 1981. The cyclization of amino acids to yield 2-azetidinones is described as in the degradation of 6-aminopenicillanic acids and 7-aminopenicillanic acids to yield 2-azetidinones.

Compounds of formula III can be prepared by the general methods described in *Ann. Chem.*, 575:217 (1951), *Angew. Chem. Int. Ed. Eng.*, 18:474 (1979), and *Coll. Czech. Chem. Comm.*, 40:2845 (1975).

The following examples are specific embodiments of this invention.

EXAMPLE 1

[3S-[3α(Z),4β]]-N-[[3-[[(2-Amino-4-thiazolyl)(metoxyimino)acetyl]amino-4-methyl-2-oxo-1-azetidinyl]carbonyl]glycine, potassium salt

(A)

(3S-trans)-N-[[3-[[(t-Butyloxy)carbonyl]amino]-4-methyl-2-oxo-1-azetidinyl]carbonyl]glycine, t-butyl ester To a suspension of potassium cyanate (186 mg, 2.3 mmol) in 2 ml of dimethylformamide was added t-butyl bromoacetate (0.356 ml, 2.2 mmol). The mixture was heated to 100° C. for 1 hour and cooled to room temperature. (3S-trans)-3-[[(t-Butyloxy)carbonyl]amino]-4-methyl-2-azetidinone (400 mg, 2.0 mmol) was then added, and the mixture was heated to 140° C. for 1 hour. Upon cooling to room temperature, the crude product was extracted from ice cold 5% HCl with three portions of ethyl acetate. The combined organic layers were extracted twice with water, once with aqueous potassium bicarbonate, and dried over sodium sulfate. The volatiles were removed, and the residue was subjected to chromatography on silica gel (eluting with 40% ethyl acetate-hexane) yielding 149 mg of the title compound.

(B)

[3S-[3α(Z),4β]]-N-[[3-[[(2-Amino-4-thiazolyl)(methoxyimino)acetyl]amino-4-methyl-2-oxo-1-azetidinyl]carbonyl]glycine, potassium salt 1-Hydroxybenzotriazole hydrate (55 mg, 0.407 mmol) and 82 mg (0.407 mmol) of (Z)-2-amino-α-(methoxyimino)-4-thiazoleacetic acid were dissolved in 1.1 ml of dimethylformamide and cooled to 0° C. N,N-Dicyclohexylcarbodiimide (84 mg, 0.407 mmol) was added and the mixture was warmed to room temperature. The reaction mixture was stirred for 30 minutes to yield the hydroxybenzotriazole ester of the starting acid which was then cooled to 0° C.

(3S-trans)-N-[[3-[[(t-Butyloxy)carbonyl]amino]-4-methyl-2-oxo-1-azetidinyl]carbonyl]glycine, t-butyl ester (121 mg, 0.339 mmol) was dissolved in 0.15 ml of anisole and cooled to 0° C. Trifluoroacetic acid (1.5 ml) was added and the resulting mixture was stirred at 0° C. for 4 hours. The volatiles were evaporated and the residue was triturated with hexane and anhydrous ether. The residue was cooled to 0° C. and dissolved in 1.1 ml of water. The pH was adjusted to 6.5 with solid KHCO$_3$ and this solution was immediately added to the above hydroxybenzotriazole ester at 0° C. The resulting mixture was stirred at 0° C. for 3 hours while maintaining the pH at 6.5-7.0 with aqueous HCl and KHCO$_3$. The reaction mixture was stirred at 5° C. overnight.

The reaction mixture was filtered to remove the dicyclohexylurea precipitate, and the volatiles were evaporated. The residue was purified by column chromatography with water on Dowex 50X2-400** resin (K+ form) followed by chromatography on HP-20* (eluting with water and 5% acetone-water) to yield 54 mg of the title compound, melting point 190°-195° C., dec.

*HP-20 is a macroporous styrene-divinylbenzene copolymer manufactured by Mitsubishi Chemical Industries.
** Dowex 50X2 is a strongly acidic cation exchange resin made by the nuclear sulfonation of styrene-divinylbenzene beads containing 2% divinylbenzene and 98% styrene and other monovinyl monomers.

EXAMPLE 2

[3S(Z)]-N-[[3-[[(2-Amino-4-thiazolyl)(methoxyimino)acetyl]amino]-2-oxo-1-azetidinyl]carbonylglycine, potassium salt

(A)

(S)-N-[[3-[[(t-Butyloxy)carbonyl]amino]-2-oxo-1-azetidinyl]carbonyl]glycine, t-butyl ester To a suspension of potassium cyanate (186 mg, 2.3 mmol) in 2 ml of dimethylformamide was added t-butyl bromoacetate (0.356 ml, 2.2 mmol). The mixture was heated to 100° C. for 1 hour and cooled to room temperature. (3S)-3-[[(t-Butyloxy)carbonyl]amino]-2-azetidinone (372 mg, 2.0 mmol) was then added, and the mixture was heated from 65° C. to 140° C. over a period of 3.5 hours, finally maintaining the temperature at 140° C. for 0.5 hours. Upon cooling to room temperature, the crude product was extracted from ice cold 5% HCl with three portions of ethyl acetate. The combined organic layers were extracted twice with water and once with aqueous potassium bicarbonate. The organic layers were then dried over sodium sulfate and filtered through a pad of silica gel. The volatiles were removed, and the residue was subjected to chromatography on silica gel (eluting with 40% ethyl acetate-hexane) yielding 180 mg of the title compound.

(B)

[3S(Z)]-N-[[3-[[(2-Amino-4-thiazolyl)(methoxyimino)acetyl]amino]-2-oxo-azetidinyl]carbonyl]-glycine, potassium salt 1-Hydroxybenzotriazole hydrate (83 mg, 0.61 mmol) and 123 mg (0.61 mmol) of (Z)-2-amino-α-(methoxyimino)-4-thiazoleacetic acid were dissolved in 1.5 ml of dimethylformamide and cooled to 0° C. N,N-Dicyclohexylcarbodiimide (126 mg, 0.61 mmol) was added, and the mixture was warmed to room temperature. The reaction mixture was stirred for 30 minutes to yield the hydroxybenzotriazole ester of the starting acid which was then cooled to 0° C.

(S)-N-[[3-[[(t-Butyloxy)carbonyl]amino]-2-oxo-1-azetidinyl]carbonyl]glycine, t-butyl ester (175 mg, 0.51 mmol) was dissolved in 0.23 ml of anisole and cooled to 0° C. Trifluoroacetic acid (2.3 ml) was added and the resulting mixture was stirred at 0° C. for 4 hours. The volatiles were evaporated and the residue was triturated with hexane and anhydrous ether. The residue was cooled to 0° C. and dissolved in 1.5 ml of water. The pH was adjusted to 6.5, with solid KHCO$_3$, and this solution was immediately added to the above hydroxybenzotriazole ester at 0° C. The resulting mixture was stirred at 0° C. for 2-½ hours while maintaining the pH at 6.5-7.0 with aqueous HCl and KHCO$_3$. The reaction mixture was then stirred at 5° C. overnight.

The reaction mixture was filtered to remove the dicyclohexyl urea precipitate, and the volatiles were evaporated. The residue was purified by column chromatography with water on Dowex 50X2-400 resin (K+ form)

followed by chromatography on HP-20 (eluting with water) to yield 74 mg of the title compound, melting point 162°–172° C., dec.

EXAMPLE 3

[3S-[3α(Z), 4α]]-N-[[3-[[(2-Amino-4-thiazolyl)(methoxyimino)acetyl]amino]-4-methyl-2-oxo-1-azetidinyl]carbonyl]glycine, potassium salt (A)

(3S-cis)-N-[[3-[[(t-Butyloxy)carbonyl]amino]-4-methyl-2-oxo-1-azetidinyl]carbonyl]glycine, t-butyl ester To a suspension of potassium cyanate (558 mg, 6.9 mmol) in 6 ml of dimethylformamide was added t-butyl bromoacetate (1.1 ml, 6.6 mmol). The mixture was heated to 100° C. for 1 hour and cooled to room temperature. (3s-cis)-3-[[(t-butyloxy)carbonyl]amino]-4-methyl-2-azetidinone (1.2 g, 6.0 mmol) was then added, and the mixture was heated to 65° C. After being stirred at 65° C. for 1 hour, the mixture was heated to 100° C. and stirred for an additional hour. Additional isocyanate was prepared (using 558 mg potassium cyanate and 1.1 ml of t-butyl bromoacetate as described above) and added to the reaction mixture at room temperature. After being heated at 65° C. for 1 hour and 100° C. for 1 hour, the reaction mixture was stirred at room temperature overnight.

The crude product was extracted from ice cold 5% HCl with three portions of ethyl acetate. The combined organic layers were extracted twice with water and once with aqueous potassium bicarbonate. The organic layers were then dried over sodium sulfate, filtered, and the volatiles were removed. The residue was subjected to flash chromatography on silica gel (eluting with 40% ethyl acetate-hexane) yielding 993 mg of the title compound.

(B)

[3S-[3α(Z),4α]]-N-[[3-[[(2-Amino-4-thiazolyl)(methoxyimino)acetyl]amino]-4-methyl-2-oxo-1-azetidinyl]carbonyl]glycine, potassium salt 1-Hydroxybenzotriazole hydrate (81 mg, 0.6 mmol) and 121 mg (0.6 mmol) of (Z)-2-amino-α-(methoxyimino)-4-thiazoleacetic acid were dissolved in 1.5 ml of dimethylformamide and cooled to 0° C. N,N-Dicyclohexylcarbodiimide (124 mg, 0.6 mmol) was added, and the mixture was warmed to room temperature. The reaction mixture was stirred for 30 minutes to yield the hydroxybenzotriazole ester of the starting acid which was then cooled to 0° C.

(3S-cis)-N-[[3-[[(t-Butyloxy)carbonyl]amino]-4-methyl-2-oxo-1-azetidinyl]carbonyl]glycine, t-butyl ester (179 mg, 0.5 mmol) was dissolved in 0.23 ml of anisole and cooled to 0° C. Trifluoroacetic acid (2.3 ml) was added and the resulting mixture was stirred at 0° C. for 2 hours. The volatiles were evaporated and the residue was triturated with hexane and anhydrous ether. The residue was cooled to 0° C. and dissolved in 1.5 ml of water. The pH was adjusted to 6.5 with solid KHCO₃, and this solution was immediately added to the above hydroxybenzotriazole ester at 0° C. The resulting mixture was stirred at 0° C. for 2 hours while maintaining the pH at 6.5–7.0 with aqueous HCl and KHCO₃. The reaction mixture was then stirred at 5° C. overnight.

The reaction mixture was filtered to remove the dicyclohexylurea precipitate, and the volatiles were evaporated. The residue was purified by column chromatography with water on Dowex 50X2-400 resin (K+ form) followed by chromatography on HP-20 (eluting with water) to yield 73 mg of the title compound, melting point 190°–200° C., dec.

EXAMPLE 4

[3S(Z)]-2-[[[1-(2-Amino-4-thiazolyl)-2-[[1-[[(carboxymethyl)amino]carbonyl]-2-oxo-3-azetidinyl]amino]-2-oxoethylidene]amino]oxy]-2-methylpropanoic acid (A)

(S)-N-[[3-[[(t-Butyloxy)carbonyl]amino]-2-oxo-1-azetidinyl]carbonyl]glycine, t-butyl ester To a suspension of potassium cyanate (933 mg, 11.5 mmol) in 10 ml of dimethylformamide was added t-butyl bromoacetate (1.8 ml, 11 mmol). The mixture was heated to 100° C. for 1 hour and cooled to room temperature. (S)-3-[[(t-Butyloxy)carbonyl]amino]-2-azetidinone (1.860 g, 10 mmol) was then added, and the mixture was heated to 65° C. After being stirred at 65° C. for 1 hour, the mixture was heated to 100° C. and stirred for an additional hour. Additional isocyanate was prepared (using 933 mg of potassium cyanate and 1.8 ml of t-butyl bromoacetate as described above) and added to the reaction mixture at room temperature. After being heated at 65° C. for 1 hour and 100° C. for 1 hour, the reaction mixture was stirred at room temperature overnight.

The crude product was extracted from ice cold 5% HCl with three portions of ethyl acetate. The combined organic layers were extracted twice with water and once with aqueous potassium bicarbonate. The organic layers were then dried over sodium sulfate, filtered, and the volatiles removed. The residue was subjected to flash chromatography on silica gel (eluting with 40% ethyl acetate-hexane) yielding 1.136 g of the title compound.

(B)

[3S(Z)]-2-[[[1-(2-Amino-4-thiazolyl)-2-[[1-[[(carboxymethyl)amino]carbonyl]-2-oxo-3-azetidinyl]amino]-2-oxoethylidene]amino]oxy]-2-methylpropanoic acid, diphenylmethyl ester Diisopropylethylamine (0.165 ml, 0.86 mmol) was added to 342 mg (0.78 mmol) of (Z)-2-amino-α-[[2-(diphenylmethoxy)-1,1-dimethyl-2-oxoethoxy]imino]-4-thiazoleacetic acid in 2.5 ml of dimethylformamide at room temperature. The mixture was cooled to −20° C., diphenyl chlorophosphate (0.162 ml, 0.78 mmol) was added, and the resulting mixture was stirred for 30 minutes to yield a mixed anhydride.

(S)-N-[[3-[[(t-Butyloxy)carbonyl]amino]-2-oxo-1-azetidinyl]carbonyl]glycine, t-butyl ester (224 mg, 0.65 mmol) was suspended in 0.3 ml of anisole and cooled to 0° C. Trifluoroacetic acid (3 ml) was added, and the resulting mixture was stirred at 0° C. for 3.5 hours. The volatiles were evaporated, and the residue was triturated with hexane and anhydrous ether to yield at yellow-white solid. The residue was dissolved in 2.2 ml of dimethylformamide at 0° C. and 0.55 ml of diisopropylethylamine was added. The mixed anhydride prepared above was then added immediately, and the reaction was stirred at 5° C. overnight.

The volatiles were removed under vacuum. The residue was purified by column chromatography with 20% acetone-water on Dowex 50X2-400 resin (K+ form) followed by chromatography on HP-20 (eluting with water, 5% acetone-water, 10% acetone-water and 20% acetone-water) to give 125 mg of the title compound.

(C)
[3S(Z)]-2-[[[1-(2-Amino-4-thiazolyl)-2-[[1-[[(carboxymethyl)amino]carbonyl]-2-oxo-3-azetidinyl]amino]-2-oxoethylidene]amino]oxy]-2-methylpropanoic acid

[3S(Z)]-2-[[[1-(2-Amino-4-thiazolyl)-2-[[1-[[(carboxymethyl)amino]carbonyl]-2-oxo-3-azetidinyl]amino]-2-oxoethylidene]amino]oxy]-2-methylpropanoic acid, diphenylmethyl ester (125 mg) was dissolved in 1.5 ml of anisole and cooled to 0° C. Trifluoroacetic acid (3 ml) was added, and the resulting mixture was stirred at 0° C. for 1 hour. The volatiles were evaporated and the residue was triturated with hexane and anhydrous ether to yield a white solid. The residue was dissolved in 2 ml of water at 0° C. and the pH was adjusted to 2.55 with aqueous KHCO$_3$. This solution was subjected to chromatography on HP-20 (eluting with water, 10% acetone-water, and 20% acetone-water) to yield 24 mg of the title compound, melting point 160°–165° C., dec.

EXAMPLE 5

[3S(Z)]-[[[3-[[(2-Amino-4-thiazolyl)[(cyanomethyoxy)imino]acetyl]amino]-2-oxo-1-azetidinyl]carbonyl]amino]acetic acid, monopotassium salt 1-Hydroxybenzotriazole hydrate (97 mg, 0.72 mmol) and 163 mg (0.72 mmol) of (Z)-2-amino-α-(cyanomethoxyimino)-4-thiazoleacetic acid were dissolved in 2 ml of dimethylformamide and cooled to 0° C. N,N-Dicyclohexylcarbodiimide (149 mg, 0.72 mmol) was added and the mixture was warmed to room temperature. The reaction mixture was stirred for 30 minutes to yield a hydroxybenzotriazole ester.

(S)-N-[[3-[[(t-Butyloxy)carbonyl]amino]-2-oxo-1-azetidinyl]carbonyl]glycine, t-butyl ester (206 mg, 0.6 mmol; see example 4A) was dissolved in 6 ml of dry acetonitrile cooled to 0° C. N-Methyl-N-trimethylsilyl trifluoroacetamide (0.244 ml, 1.32 mmol) was added and the mixture was warmed to room temperature. After stirring for 45 minutes at room temperature, trimethylsilyliodide (0.188 ml, 1.32 mmol) was added dropwise and the reaction mixture was stirred for 15 minutes at room temperature. The volatiles were evaporated without external heating, the residue was dissolved in 4 ml of dimethylformamide and this solution was immediately added to the hydroxybenzotriazole ester. The reaction mixture was stirred at room temperature overnight.

The reaction mixture was filtered to remove the dicyclohexyl urea precipitate and then cooled to 0° C. After adding 1 ml of water and stirring at 0° C. for 30 minutes, the volatiles were evaporated. The residue was suspended in water at 0° C. and the pH was adjusted to 6.5 with aqueous KHCO$_3$. Purification by column chromatography on HP-20 (eluting with water) yielded 86 mg of the title compound, melting point 160°–165° C., dec.

EXAMPLE 6

[3S(Z)]-N-[[3-[[(2-Amino-4-thiazolyl)(ethoxyimino)acetyl]amino]-2-oxo-1-azetidinyl]carbonyl]glycine, potassium salt 1-Hydroxybenzotriazole hydrate (97 mg, 0.72 mmol) and 155 mg (0.72 mmol) of (Z)-2-amino-α-(ethoxyimino)-4-thiazoleacetic acid were dissolved in 2 ml of dimethylformamide and cooled to 0° C. N,N-Dicyclohexylcarbodiimide (149 mg, 0.72 mmol) was added, and the mixture was warmed to room temperature. The reaction mixture was stirred for 30 minutes to yield a hydroxybenzotriazole ester.

(S)-N-[[3-[[(t-Butyloxy)carbonyl]amino]-2-oxo-1-azetidinyl]carbonyl]glycine, t-butyl ester (206 mg, 0.6 mmol; see example 4A) was dissolved in 6 ml of dry acetonitrile and cooled to 0° C. N-Methyl-N-(trimethylsilyl)trifluoroacetamide (0.244 ml, 1.32 mmol) was added and the mixture was warmed to room temperature. After stirring for 45 minutes at room temperature, trimethylsilyliodide (0.188 ml, 1.32 mmol) was added dropwise, and the reaction mixture was stirred for 15 minutes at room temperature. The volatiles were evaporated without external heating, the residue was dissolved in 4 ml of dimethylformamide, and this solution was then immediately added to the hydroxybenzotriazole ester. The reaction mixture was stirred at room temperature overnight.

The reaction mixture was filtered to remove the dicyclohexylurea precipitate and was then cooled to 0° C. After adding 1 ml of water and stirring at 0° C. for 30 minutes, the volatiles were evaporated. The residue was suspended in water at 0° C. and the pH was adjusted to 6.5 with aqueous KHCO$_3$. Purification by column chromatography on HP-20 (eluting with water) yielded 60 mg of the title compound, melting point 175°–180° C., dec.

EXAMPLE 7

[3S(Z)]-N-[[3-[[(2-Amino-4-thiazolyl)(methoxyimino)acetyl]amino]-2-oxo-1-azetidinyl]carbonyl]-DL-alanine (A) [1-[(Phenylmethoxy)carbonyl]ethyl]isocyanate Benzyl alaninate hydrochloride (9.3 g, 43 mmol) was suspended in 150 ml of dry toluene under a positive pressure of argon. The reaction mixture was heated to reflux and phosgene was bubbled through for 2 hours. Nitrogen was then bubbled through while the reaction mixture continued to reflux for 15 minutes. The reaction mixture was cooled to room temperature while nitrogen was bubbled through for an additional hour to remove any phosgene present. The toluene was evaporated, and the residue was distilled (97°–107° C., 0.3 mm of Hg) to yield the title compound.

(B)
(S)-N-[[3-[[(Phenylmethoxy)carbonyl]amino]-2-oxo-1-azetidinyl]carbonyl]-DL-alanine, phenylmethyl ester A solution of (S)-3-[[(phenylmethoxy)carbonyl]amino]-2-azetidinone (416 mg, 2.0 mmol) in 12 ml of dry tetrahydrofuran at 75° C. was treated with 1.28 ml (2.2 mmol) of 1.72N n-butyl lithium. After 30 minutes, a solution of [1-[(phenylmethoxy)carbonyl]ethyl]isocyanate (0.548 ml, ~2.2 mmol—corrected for ~73% purity by weight) in 2 ml of dry tetrahydrofuran was added to the reaction mixture.

After stirring at −75° C. for 45 minutes, the reaction mixture was poured into aqueous KH$_2$PO$_4$ and extracted with 3 portions of ethyl acetate. The combined organic layers were extracted once with water, dried with Na$_2$SO$_4$, and filtered. The volatiles were removed, and the residue was subjected to chromatography on silica gel (eluting with 40% ethyl acetate-hexane) yielding 524 mg of the title compound.

(C)

[3S(Z)]-N-[[3-[[(2-Amino-4-thiazolyl)(methoxyimino)acetyl]amino]-2-oxo-1-azetidinyl]carbonyl]-DL-alanine Diisopropylethylamine (0.283 ml, 1.62 mmol) was added to 296 mg (1.47 mmol) of (Z)-2-amino-α-(methoxyimino)-4-thiazoleacetic acid in 4.5 ml of dimethylformamide at 23° C. The mixture was cooled to −20° C. and diphenylchlorophosphate (0.305 ml, 1.47 mmol) was added. The resulting mixture was stirred for 30 minutes to yield a mixed anhydride.

(S)-N-[[3-[[(Phenylmethoxy)carbonyl]amino]-2-oxo-1-azetidinyl]carbonyl]-DL-alanine, phenylmethyl ester (518 mg, 1.22 mmol) was dissolved in 4.5 ml of dimethylformamide and 232 mg (1.22 mmol) of p-toluenesulfonic acid monohydrate was added. Hydrogenolysis of the protecting groups at room temperature over 252 mg of 10% palladium on charcoal was complete after 1-½ hours. The reaction mixture was placed under nitrogen and cooled to 0° C. Diisopropylethylamine (0.7 ml, 4.02 mmol) was then added to the azetidinone, followed by the mixed anhydride prepared above. After stirring at 0° C. for 1 hour, the reaction mixture was stirred at 5° C. overnight.

The volatiles were removed under vacuum. The residue was purified by column chromatography with water on Dowex 50X2-400 resin (K+ form) followed by chromatography on HP-20 resin (eluting with water) to yield the title compound contaminated with potassium tosylate. This material was cooled to 0° C. and acidified to pH 2.5 by addition of 1N HCl. Chromatography on HP-20 resin (eluting with water, 5% acetone-water, and 10% acetone-water) followed by lyophilization yielded 140 mg of the title compound, melting point 140°–150° C.

EXAMPLE 8

[3S(Z)]-[N-[[3-[[(2-Amino-4-thiazolyl)(methoxyimino)acetyl]amino]-2-oxo-1-azetidinyl]carbonyl]methylamino]acetic acid (A)
(S)-[N-[[3-[[(Phenylmethoxy)carbonyl]amino]-2-oxo-1-azetidinyl]carbonyl]methylamino]acetic acid, phenylmethyl ester Potassium carbonate (553 mg, 4 mmol) was added to a rapidly stirring solution of benzyl sarcosine hydrochloride (431 mg, 2.0 mmol) in 5 ml of dichloromethane at 0° C. (pH ∼8). The mixture was extracted 3 times with dichloromethane and the combined organic layers were dried over Na2SO4 and filtered. The volume of solvent was reduced to ∼2 ml by evacuation and dried with 4A molecular sieves to yield the free amine of the starting sarcosine.

The solution containing the free amine was cooled to 0° C. and 0.32 ml (2.3 mmol) of triethylamine was added. The resulting mixture was immediately added dropwise to a solution of 12.5% phosgene in toluene (2.9 ml, 3.4 mmol) at −25° C. After stirring at −25° C. for 1 hour, the volatiles were evaporated without external heating to yield crude N-(chlorocarbonyl)-N-methylglycine, phenylmethyl ester. The compound was not characterized but was used as a crude intermediate.

The crude N-(chlorocarbonyl)-N-methylglycine, phenylmethyl ester was redissolved in 4 ml of dichloromethane and cooled to 0° C. (S)-3-[[(Phenylmethoxy)carbonyl]amino-2-azetidinone (440 mg, 2.0 mmol) and 24 mg of dimethylaminopyridine were added to the stirring solution. Triethylamine (0.307 ml, 2.2 mmol) was added dropwise, and the reaction mixture was warmed to room temperature.

After stirring for 45 hours at room temperature, the crude reaction mixture was poured into aqueous KH2PO4 and extracted 4 times with ethyl acetate. The combined organic layers were dried over Na2SO4 and filtered. The volatiles were removed, and the residue was subjected to chromatography on silica gel (eluting with 50% ethyl acetate-hexane) yielding 231 mg of the title compound.

(B)
[3S(Z)]-[N-[[3-[[(2-Amino-4-thiazolyl)(methoxyimino)acetyl]amino]-2-oxo-1-azetidinyl]carbonyl]methylamino]acetic acid Diisopropylethylamine (0.204 ml, 1.17 mmol) was added to 213 mg (1.06 mmol) of (Z)-2-amino-α-(methoxyimino)-4-thiazoleacetic acid in 3.3 ml of dimethylformamide at 23° C. The mixture of cooled to −20° C. and diphenylchlorophosphate (0.220 ml, 1.06 mmol) was added, and the resulting mixture was stirred for 30 minutes to yield a mixed anhydride.

(S)-[N-[[3-[[(Phenylmethoxy)carbonyl]amino]-2-oxo-1-azetidinyl]carbonyl]methylamino]acetic acid, phenylmethyl ester (372 mg, 0.88 mmol) was dissolved in 3.3 ml of dimethylformamide and 167 mg (0.88 mmol) of p-toluenesulfonic acid monohydrate was added. Hydrogenolysis of the phenylmethyl and (phenylmethoxy)carbonyl protecting groups at room temperature over 182 mg of 10% palladium on charcoal was complete after 1-½ hours. The reaction mixture was placed under nitrogen and cooled to 0° C. Diisopropylethylamine (0.506 ml, 2.90 mmol) was then added to the azetidinone followed by the mixed anhydride in the presence of 3A molecular sieves. After stirring at 0° C. for 2 hours, the reaction mixture was stirred at 5° C. overnight.

The volatiles were removed under vaccum. The residue was purified by column chromatography with water on Dowex 50X2-400 resin (K+ form) followed by chromatography on HP-20 resin (eluting with water) to yield 165 mg of crude product. The product was cooled to 0° C. and acidified to a pH of 2.5 with the addition of 1N HCl. Chromatography on HP-20 resin (eluting with water, 5% acetone-water, and 10% acetone-water) followed by lyophilization yielded 139 mg of the title compound, melting point 145°–150° C., dec.

EXAMPLE 9

[3S(Z)]-N-[[3-[[(2-Amino-4-thiazolyl)(methoxyimino)acetyl]amino]-2-oxo-1-azetidinyl]thioxomethyl]glycine, potassium salt (A)
(S)-N-[[3-[[(t-Butyloxy)carbonyl]amino]-2-oxo-1-azetidinyl]thioxomethyl]glycine, t-butyl ester A solution of (S)-3-[[(t-butyloxy)carbonyl]amino]-2-azetidinone (186 mg, 1 mmol) in 6 ml of dry tetrahydrofuran at −75° C. was treated with 0.65 ml (1.1 mmol) of 1.68N n-butyl lithium. After 30 minutes, a solution of t-butyl isothiocyanatoacetate (0.17 ml, 1.1 mmol) in 1 ml of dry tetrahydrofuran was added to the reaction mixture. After stirring at −75° C. for 2 hours, the reaction mixture was placed at −70° C. overnight.

The crude product was extracted from aqueous KH2PO4 with three portions of ethyl acetate. The combined organic layers were extracted once with water, dried over Na₂SO₄ and filtered. The volatiles were removed, and the residue was subjected to chromatography on silica gel (eluting with 20% ethyl acetate-hexane) yielding 168 mg of the title compound.

(B)
[3S(Z)]-N-[[3-[[(2-Amino-4-thiazolyl)(methoxyimino)acetyl]amino]-2-oxo-1-azetidinyl]thioxomethyl]glycine, potassium salt 1-Hydroxybenzotriazole hydrate (74 mg, 0.55 mmol) and 111 mg (0.55 mmol) of (Z)-2-amino-α-(methoxyimino)-4-thiazoleacetic acid were dissolved in 2 ml of dimethylformamide and cooled to 0° C. N,N-Dicyclohexylcarbodiimide (114 mg, 0.55 mmol) was added, and the mixture was warmed to room temperature. The reaction mixture was stirred for 30 minutes to yield a hydroxybenzotriazole ester.

(S)-N-[[3-[[(t-Butyloxy)carbonyl]amino]-2-oxo-1-azetidinyl]thioxomethyl]glycine, t-butyl ester (164 mg. 0.46 mmol) was dissolved in 5 ml of dry acetonitrile and cooled to 0° C. N-Methyl-N-(trimethylsilyl)trifluoroacetamide (0.187 ml, 1.01 mmol) was added and the mixture was warmed to room temperature. After stirring for 45 minutes at room temperature, trimethylsilyl iodide (0.144 ml, 1.01 mmol) was added dropwise, and the reaction mixture was stirred for 15 minutes at room temperature. The volatiles were evaporated without external heating, the residue was dissolved in 3 ml of dimethylformamide, and this solution was then immediately added to the ester. The reaction mixture was stirred at room temperature overnight.

The reaction mixture was filtered to remove the dicyclohexylurea precipitate and cooled to 0° C. After adding 1 ml of water and stirring at 0° C. for 30 minutes, the volatiles were evaporated. The residue was suspended in water at 0° C. and the pH was adjusted to 6.5 with aqueous KHCO₃. Purification by column chromatography on HP-20 (eluting with water) yielded 66 mg of the title compound, melting point 180°–190° C., dec.

EXAMPLE 10

[3S(Z)]-N-[[3-[[(2-Amino-4-thiazolyl)(ethoxyimino)acetyl]amino]-2-oxo-1-azetidinyl]carbonyl]-N-methylglycine, potassium salt (A)
(S)-[(3-Amino-2-oxo-1-azetidinyl)carbonyl]-N-methylglycine, p-toluenesulfonate To a solution of (S)-[N-[[3-[[(phenylmethoxy)carbonyl]amino]-2-oxo-1-azetidinyl]carbonyl]methylamino]acetic acid, phenylmethyl ester (581 mg, 1.37 mmol; see example 8A) in dimethylformamide (4 ml) was added 10% palladium on charcoal (284 mg) and p-toluene-sulfonic acid (260 mg, 1.37 mmol). The nitrogen atmosphere was replaced with hydrogen and the slurry was stirred for 1.5 hours to yield the title compound.

(B)
[3S(Z)]-N-[[3-[[(2-Amino-4-thiazolyl)(ethoxyimino)acetyl]amino]-2-oxo-1-azetidinyl]carbonyl]-N-methyglycine, potassium salt To a slurry of N-hydroxybenzotriazole (185 mg, 1.37 mmol) and (Z)-2-amino-α-(ethoxyimino)-4-thiazoleacetic acid (294 mg, 1.37 mmol) in dimethylformamide (7 ml) at 0° C. was added dicyclohexylcarbodiimide (310 mg, 1.5 mmol). After stirring for 30 minutes, ethyldiisopropylamine (1 ml, 5.48 mmol) and the azetidinone from above were added without filtering. This was stirred at room temperature for 20 hours. The slurry was filtered and washed with dimethylformamide. The filtrate was concentrated in vacuo. The residue was suspended in acetone (7 ml) and a small amount of precipitate filtered. To the filtrate was then added perfluorobutanesulfonic acid, potassium salt (463 mg, 1.36 mmol). After agitating for 10 minutes, ether (12 ml) was added and the slurry was cooled to 5° C. and filtered. The precipitate was washed with ether (two 5 ml portions) and dried to give 800 mg of material, which was dissolved in water, applied to a column of HP20 (2.5×20 cm) and eluted with a gradient of 0–30% acetone. The product was eluted with 30% acetone. The product was still impure by TLC and was rechromatographed on HP20 at pH 7 (K₂CO₃) and was eluted with 15% acetone. This was concentrated to give 45 mg of product, melting point 180°–190° C., dec.

Analysis calc'd for C₁₄H₁₇N₆O₆SK.H₂O: C, 37.00; H, 4.21; N, 18.49; S, 7.05. Found: C, 37.10; H, 4.29; N, 18.05; S, 6.20.

EXAMPLE 11

[3S(Z)]-2-[[[1-(2-Amino-4-thiazolyl)-2-[[1-[[(carboxymethyl)methylamino]carbonyl]-2-oxo-3-azetidinyl]amino]-2-oxoethylidene]amino]oxy]-2-methylpropanoic acid (A)
[3S(Z)-2-[[[1-(2-Amino-4-thiazolyl)-2-[[1-[[(carboxymethyl)methylamino]carbonyl]-2-oxo-3-azetidinyl]amino]-2-oxoethylidene]amino]oxy]-2-methylpropanoic acid, diphenylmethyl ester, potassium salt Diisopropylethylamine (0.185 ml, 1.05 mmol) was added to 376 mg of (Z)-2-amino-α-[[2-(diphenylmethoxy)-1,1-dimethyl-2-oxoethoxy]imino]-4-thiazoleacetic acid in 3 ml of dimethylformamide at room temperature. The mixture was cooled to −20° C., diphenyl chlorophosphate was added and the resulting mixture was stirred for 30 minutes to yield a mixed anhydride.

(S)-[N-[[3-[[(Phenylmethoxy)carbonyl]amino]-2-oxo-1-azetidinyl]carbonyl]methylamino]acetic acid, phenylmethyl ester (340 mg, 0.8 mmol; see example 8A) was dissolved in 3 ml of dimethylformamide and 152 mg (0.8 mmol) of p-toluenesulfonic acid monohydrate was added. Hydrogenolysis of the protecting groups at room temperature over 165 mg of 10% palladium on charcoal was complete after 70 minutes. The reaction mixture was placed under nitrogen and cooled to 0° C. Diisopropylethylamine (0.464 ml, 2.66 mmol) was then added to the azetidinone immediately followed by the above prepared mixed anhydride. After stirring at 0° C. for 1 hour, the reaction mixture was stirred at 5° C. overnight.

The reaction mixture was filtered to remove the palladium on charcoal and the volatiles were removed under vacuum. The residue was purified by column chromatography with 20% acetone-water on Dowex 50X2-400 resin (K⁺ form) followed by chromatography on HP-20 (eluting with water, 10% acetone-water, and 20% acetone-water) to give ∼200 mg of the title compound.

(B)

[3S(Z)]-2-[[[1-(2-Amino-4-thiazolyl)-2-[[1-[[(carboxymethyl)methylamino]carbonyl]-2-oxo-3-azetidinyl]amino]-2-oxoethylidene]amino]oxy]-2-methylpropanoic acid

[3S(Z)]-2-[[[1-(2-Amino-4-thiazolyl)-2-[[1-[[(carboxymethyl)methylamino]carbonyl]-2-oxo-3-azetidinyl]amino]-2-oxoethylidene]amino]oxy]-2-methylpropanoic acid (~190 mg) was cooled to −20° C. and a solution containing 4 ml of trifluoroacetic acid, 4 ml of dichloromethane, and 2 ml of anisole at 0° C. was added. After stirring at −20° C. for 30 minutes, the volatiles were evaporated and the residue was triturated with hexane and anhydrous ether to yield a white solid. The residue was dissolved in ~2 ml of water at 0° C. and the pH was adjusted to 2.5 with aqueous $KHCO_3$. This solution was subjected to chromatography on HP-20 (eluting with water, 10% acetone-water, and 20% acetone-water) to yield 35 mg of the title compound, melting point 150°–160° C., dec.

EXAMPLE 12

[3S(Z)-N-[[3-[[(2-Amino-4-thiazolyl)(methoxyimino)acetyl]amino]-2-oxo-1-azetidinyl]carbonyl]-N-methyl-DL-alanine, potassium salt (A) N-Methyl-DL-alanine Pyruvic acid (2.5 ml, 0.036 mol) and benzylmethylamine (2.9 ml, 0.022 mol) were added to ethanol (50 ml) containing Pearlman's catalyst ($Pd(OH)_2$, 0.5 g). The mixture was vigorously stirred under one atmosphere of hydrogen at ambient temperature until an equivalent amount of hydrogen had reacted. The mixture was filtered through Celite and ethanol was removed in vacuo. The filter cake was extracted with hot ethanol and the combined filtrates crystallized upon standing in the freezer. Upon filtration, the desired product was collected and dried yielding a solid (725 mg).

(B) N-Methyl-DL-alanine, benzyl ester

A mixture of N-methyl-DL-alanine (2.5 g, 0.024 mol), benzyl alcohol (12.5 g, 0.116 mol) and p-toluenesulfonic acid monohydrate (5.04 g, 0.026 mol) were heated at reflux for 48 hours in benzene (75 ml) under a Dean-Stark trap to remove water. After cooling to room temperature, the mixture was diluted with ether (100 ml) and allowed to stand in the freezer. The toluenesulfonate salt of the desired product was collected by filtration, washed with ether, and then dried in vacuo, yielding crystals (7.46 g).

The free amine was obtained by dissolving the salt (5.48 g, 0.015 mol) in water (15 ml) and adjusting to pH 8 with dilute potassium carbonate solution. After extracting three times with ethyl acetate, the extracts were combined, washed with saturated NaCl solution, dried ($Na_2SO_4$), and solvent was removed in vacuo yielding the desired product as an oil (2.8 g).

(C)

(S)-N-[[3-[[(Phenylmethoxy)carbonyl]amino]-2-oxo-1-azetidinyl]carbonyl]N-methyl-DL-alanine, phenylmethyl ester A solution of phosgene in toluene (4.7 ml of a 20% solution, 9.36 mmol) was cooled to −25° C. under argon. While stirring, a solution (pre-cooled to 0° C.) of N-methyl-DL-alanine, benzyl ester (1.0 g, 5.2 mmol) and triethylamine (870 μl, 6.25 mmol) in dichloromethane (5 ml) was added over 5 minutes maintaining the temperature at −20° to −25° C. After stirring at −25° C. for 1 hour, solvent and excess phosgene were removed in vacuo. The residue was dissolved in dichloromethane (12 ml), cooled to 0° C. and then (S)-3-[[(phenylmethoxy)carbonyl]amino]-2-azetidinone (1.15 g, 5.2 mmol), dimethylaminopyridine (63 mg, 0.52 mmol), and triethylamine (870 μl, 6.2 mmol) were added sequentially. Stirring was continued for 10 minutes at 0° C. and then overnight at room temperature. After refluxing for an additional 7 hours, the mixture was again stirred overnight at room temperature. The mixture was washed with water, dried ($Na_2SO_4$) and solvent was removed in vacuo. The resulting oil was chromatographed on silica gel eluting with a 4:6 ethyl acetate:hexane mixture. The desired product was obtained as an oil (580 mg).

(D)

(S)-[(3-Amino-2-oxo-1-azetidinyl)carbonyl]-N-methyl-DL-alanine, phenylmethyl ester, p-toluenesulfonate (S)-N-[[3-[[(Phenylmethoxy)carbonyl]amino]-2-oxo-1-azetidinyl]carbonyl]-N-methyl-DL-alanine, phenylmethyl ester (105 mg, 0.24 mmol) was dissolved in dimethylformamide (3 ml), and p-toluenesulfonic acid monohydrate (46 mg, 0.24 mmol) and 10% palladium on charcoal (50 mg) were added. Stirring under a hydrogen atmosphere for 2.5 hours at room temperature cleaved both protecting groups.

(E)

[3S(Z)]-N-[[3-[[(2-Amino-4-thiazolyl)(methoxyimino)acetyl]amino]-2-oxo-1-azetidinyl]carbonyl]-N-methyl-DL-alanine, potassium salt (Z)-2-Amino-α-(methoxyimino)-4-thiazoleacetic acid (58 mg, 0.228 mmol) was dissolved in dimethylformamide (2 ml), cooled to −25° C., and diphenyl chlorophosphate (6 ml, 0.288 mmol) followed by diisopropylethylamine (56 μl, 0.32 mmol) was added. After stirring the mixture at −20° to −15° C. for 30 minutes, this solution was added to the hydrogenation mixture which had been cooled to 0° C. and treated with diisopropylethylamine (138 μl, 0.79 mmol). The reaction was maintained under argon at 0° to 5° C. for 18 hours. Solvent was removed in vacuo, the residue was taken up in water, and the pH was adjusted to 6.5 with dilute $KHCO_3$ solution. The mixture was chromatographed on an ion-exchange column (34 ml, Dowex 50X2-400, K+ form) eluting with water. The partially purified product was then chromatographed on an HP-20 resin column eluting with water. After lyophilization, the desired product was obtained as a powder (32 mg).

EXAMPLE 13

[3S-[3α(Z),4β]]-N-[[3-[[(2-Amino-4-thiazolyl)(methoxyimino)acetyl]amino]-4-methyl-2-oxo-1-azetidinyl]carbonyl]-N-methylglycine, potassium salt (A)

(3S-trans)-N-[[3-[[t-Butoxycarbonyl]amino]-4-methyl-2-oxo-1-azetidinyl]carbonyl]-N-methylglycine, t-butyl ester A solution of phosgene in toluene (1.35 ml of a 20% solution, 2.698 mmol) was cooled to −25° C. under an argon atmosphere. A solution of N-methylglycine, t-butyl ester (218 mg, 1.498 mmol) and triethylamine (251 μl, 1.798 mmol) in dichloromethane (2 ml) was added dropwise over 5 minutes. The reaction was stirred for 1 hour at −25° C. (after 15 minutes an additional 0.2 ml of dichloromethane was added to facilitate stirring). The volatiles were removed starting at −25° C. and slowly by warming to room temperature. The residue was dissolved in methylene chloride (5 ml), cooled to 0° C. and treated with (3S-trans)-3-[[t-butoxycarbonyl-]amino]-4-methyl-2-azetidinone (300 mg, 1.498 mmol; pre-dried over P$_2$O$_5$ at 25° C. under high vacuum), 4-dimethylaminiopyridine (18 mg, 0.149 mmol), and triethylamine (251 μl, 1.798 mmol). The resulting mixture was warmed to room temperature, stirred for 36 hours, treated with additional triethylamine (502 μl), and refluxed for 5 hours. The reaction was cooled, diluted with ethyl acetate, washed with pH 4.5 KH$_2$PO$_4$, and with brine, and then dried over sodium sulfate. Filtration and concentration in vacuo produced 525 mg of an oil which was chromatographed on 21 g of silica gel (230–400 mesh). Elution with 40% ethyl acetate-hexane gave 356 mg of the title compound as a white solid.

(B)

(3S-trans)-N-[(3-amino-2-methyl-4-oxo-1-azetidinyl)-carbonyl]-N-methylglycine, trifluoroacetic acid salt A solution of (3S-trans)-N-[[3-[[t-butoxycarbonyl-]amino]-b 4-methyl-2-oxo-1-azetidinyl]carbonyl]-N-methylglycine, t-butyl ester (140 mg, 0.377 mmol) in anisole (0.68 ml) was cooled to −30° C. under an argon atmosphere. Trifluoroacetic acid (1.4 ml) was added dropwise and the reaction was warmed to 0° C. and stirred for 1 hour, at 10° C. for 30 minutes, and at room temperature for 2.5 hours. The reaction was cooled to −15° C., treated sequentially with ether (9.5 ml) and hexane (4.8 ml), and stirred for 10 minutes. The cooling bath was removed and the mixture was stirred for 30 minutes. The precipitated white solid was isolated by centrifugation, washed with ether and hexane, and dried in vacuo. The yield of the title compound was 110 mg.

(C)

[3S-[3[(Z),4β]]-N-[[3-[[(2-Amino-4-thiazolyl)(methoxyimino)acetyl]amino]-4-methyl-2-oxo-1-azetidinyl]carbonyl]-N-methylglycine, potassium salt A solution of (Z)-2-amino-α-(methoxyimino)-4-thiazoleacetic acid (58 mg, 0.288 mmol) in dimethylformamide (1.3 ml) was treated with triethylamine (40 μl, 0.288 mmol) and stirred at room temperature for 10 minutes under an argon atmosphere. The mixture was cooled to −30° C. and diphenyl chlorophosphate (60 μl, 0.288 mmol) was added. The reaction mixture was stirred for 35 minutes at −25° C. to −30° C., cooled to −45° C., and treated with (3S-trans)-N-[(3-amino-2-methyl-4-oxo-1-azetidinyl)carbonyl]-N-methylglycine, trifluoroacetic acid salt (95 mg, 0.288 mmol) followed by N,N-diisopropylethylamine (251 μl, 1.44 mmol) and dimethylformamide (0.2 ml). The reaction was warmed to −25° C., stirred for 30 minutes, warmed to 5° C. and stirred overnight. The volatiles were removed under high vacuum, the residue was dissolved in water, and passed through a Dowex K+ ion-exchange resin (32 ml). Fractions 1–16 (3 ml fractions) were combined and lyophilized producing 100 mg of an orange solid. The crude product was chromatographed on 120 ml of HP-20. Fractions 1–20 (5 ml fractions) were eluted with water, fractions 21–40 with 5% acetone-water, and fractions 41–80 with 10% acetone-water. Fractions 60–62 were combined and lyophilized to afford 43 mg of the title compound as a white solid.

Analysis calc'd for C$_{14}$H$_{17}$N$_6$O$_6$SK.3.1H$_2$O: C,34.15; H,4.75 N,17.07. Found: C,34.13; H, 5.00; N, 16.90.

EXAMPLE 14

[3S(R)]-N-[[3-[[[[(4-Ethyl-2,3-dioxo-1-piperazinyl)carbonyl]amino]phenylacetyl]amino]-2-oxo-1-azetidinyl]-carbonyl]methylamino]acetic acid, potassium salt (A)

(S)-[[(3-Amino-2-oxo-1-azetidinyl)carbonyl]methylamino]acetic acid, p-toluenesulfonate To a solution of (S)-[[[3-[[(phenylmethoxy)carbonyl-]amino]-2-oxo-1-azetidinyl]carbonyl]methylamino]acetic acid, phenylmethyl ester (800 mg., 1.88 mmol) in dimethylformamide (5 ml) was added p-toluenesulfonic acid (357 mg, 1.88 mmol) and 10% palladium on charcoal (388 mg). The nitrogen atmosphere was replaced with hydrogen and the slurry was stirred for 1 hour at room temperature to yield the title compound.

(B)

[3S(R)]-[[[3-[N-[[[(4-Ethyl-2,3-dioxo-1-piperazinyl)carbonyl]amino]phenylacetyl]amino]-2-oxo-1-azetidinyl]-carbonyl]methylamino]acetic acid, potassium salt Dicyclohexylcarbodiimide (426 mg, 2 mmol) was added to a slurry of N-hydroxybenzotriazole (254 mg, 1.88 mmol) and α-[[(4-ethyl-2,3-dioxo-1-piperazinyl)-carbonyl]amino]benzeneacetic acid (600 mg, 1.88 mmol) at 0° C. After 30 minutes, ethyldiisopropylamine (1.3 ml, 7.96 mmol) was added to (S)-[N-[(3-amino-2-oxo-1-azetidinyl)carbonyl]methylamino]acetic acid, p-toluenesulfonate, and this mixture was then added to the benzeneacetic acid derivative containing mixture. This was stirred at room temperature for 20 hours, filtered, and the solvents removed in vacuo. The residue was triturated with acetone and dicyclohexylurea was filtered off. The acetone was evaporated in vacuo and the residue was dissolved in water and the pH raised to 7 with KHCO$_3$. Purification on Dowex 50WX2 (200–400 mesh, K+ form) gave 400 mg of product which was further purified by chromatographing it twice on HP20, eluting with a 0–30% gradient of acetone, and yielding 33 mg of the title compound, melting point 155° C., dec.

EXAMPLE 15

[3S(Z)]-N-[[3-[[(2-Amino-4-thiazolyl)(methoxyimino)acetyl]amino]-2-oxo-1-azetidinyl]carbonyl]-N-ethylglycine, potassium salt (A)

(S)-[N-[[3-[[(Phenylmethoxy)carbonyl]amino]-2-oxo-1-azetidinyl]carbonyl]ethylamino]acetic acid, phenylmethyl ester (S)-3-[[(Phenylmethoxy)carbonyl]amino]-2-azetidinone was suspended in 5 ml of dichloromethane and cooled to −10° C. A solution of 12.5% phosgene in toluene (2.9 ml, 3.4 mmol) was added dropwise to the rapidly stirring mixture. After stirring at −10° C. for 2 hours, the volatiles were evaporated without external heating. The residue was cooled to −10° C. and dissolved in 5 ml of dichloromethane to give (S)-1-chlorocarbonyl-3-[[(phenylmethoxy)carbonyl]amino]-2-azetidinone. The compound was not characterized, but was used as a crude intermediate.

Potassium carbonate (608 mg, 4.4 mmol) was added to a rapidly stirring solution of N-ethylglycine benzyl ester hydrochloride (505 mg, 2.2 mmol) in 5 ml of water and 5 ml of dichloromethane at 0° C. (pH~8). The mixture was extracted three times with dichloromethane and the combined organic layers were dried over $Na_2SO_4$ and filtered. The volume of solvent was reduced to ~2 ml by evacuation and dried with 4A molecular sieves to yield the free amine of the benzyl ester.

Triethylamine (0.307 ml, 2.2 mmol) was added to the solution containing the free amine and the resulting mixture was immediately added to the solution containing (S)-1-chlorocarbonyl-3-[[(phenylmethoxy)carbonyl]amino]-2-azetidinone at −10° C. After stirring at −10° C. for 0.5 hour, the reaction mixture was poured into aqueous $KH_2PO_4$ and extracted three times with dichloromethane. The combined organic layers were dried over $Na_2SO_4$ and filtered. The volatiles were removed and the residue was subjected to chromatography on silica gel (eluting with 40% ethyl acetate hexane) yielding 296 mg of the title compound.

(B)
[3S(Z)]-N-[[3-[[(2-Amino-4-thiazolyl)(methoxyimino)acetyl]amino]-2-oxo-1-azetidinyl]carbonyl]-N-ethylglycine, potassium salt Diisopropylethylamine (0.155 ml, 0.89 mmol) was added to 163 mg (0.81 mmol) of (Z)-2-amino-α-(methoxyimino)-4-thiazoleacetic acid in 2.7 ml of dimethylformamide at 23° C. The mixture was cooled to −20° C. and diphenylchlorophosphate (0.168 ml, 0.81 mmol) was added and the resulting mixture was stirred for 30 minutes to yield a mixed anhydride.

(S)-[N-[[3-[[(Phenylmethoxy)carbonyl]amino]-2-oxo-1-azetidinyl]carbonyl]ethylamino]acetic acid, phenylmethyl ester (296 mg, 0.67 mmol) was dissolved in 2.7 ml of dimethylformamide and 128 mg (0.67 mmol) of p-toluenesulfonic acid monohydrate was added. Hydrogenolysis of the protecting groups at room temperature over 139 mg of 10% palladium on charcoal was complete after 1 hour and 30 minutes. The reaction mixture was placed under nitrogen and cooled to 0° C. Diisopropylethylamine (0.387 ml, 2.21 mmol) was then added to the azetidinone immediately followed by the mixed anhydride, and the resulting mixture was stirred at 5° C. overnight.

The reaction mixture was filtered to remove the palladium on charcoal and the volatiles were removed under vacuum. The residue was purified by column chromatography with water on Dowex 50x2-400 resin (K+ form) followed by chromatography on HP-20 (eluting with water) to yield, after lyophilization, 109 mg of the title compound, melting point 187°-195° C., dec.

EXAMPLE 16
[3S(Z)]-N-[[3-[[(2-Amino-4-thiazolyl)(methoxyimino)acetyl]amino]-2-oxo-1-azetidinyl]carbonyl]methylamino]acetic acid, methyl ester (A)
[3S(Z)]-N-[[3-[[(2-Amino-4-thiazolyl)(methoxyimino)acetyl]amino]-2-oxo-1-azetidinyl]carbonyl]methylamino]acetic acid, potassium salt

[3S(Z)]-[[[3-[[(2-Amino-4-thiazolyl)(methoxyimino)acetyl]amino]-2-oxo-1-azetidinyl]carbonyl]methylamino]acetic acid (~8 g of crude) was dissolved in 10 ml of 0.1 m $KHCO_3$. The pH was adjusted to 6.5 with a concentrated solution of $K_2CO_3$ in water, and the material was purified on Dowex 50WX2 (K+ form). The fractions containing the desired material were combined and purified on HP20 (5×30 cm) eluting with water. Fractions 37-40 contained the title compound plus p-toluenesulfonic acid, potassium salt in the molar ratio of 6.5/10.

(B)
[3S(Z)]-[N-[[3-[[(2-Amino-4-thiazolyl)(methoxyimino)acetyl]amino]-2-oxo-1-azetidinyl]carbonyl]methylamino]acetic acid, methyl ester

[3S(Z)]-[[[3-[[(2-Amino-4-thiazolyl)(methoxyimino)acetyl]amino]-2-oxo-1-azetidinyl]carbonyl]methylamino]acetic acid, potassium salt (318 mg of a mixture containing 150 mg of the potassium salt) was dissolved in dimethylformamide (5 ml) and the volume reduced to 1 ml. Methyl iodide (22 μl) was added, and after 1 hour an additional 22 μl of methyl iodide was added. After another hour, the solvents were removed, the product was extracted in acetone, and the solvent was removed.

The residue was chromatographed on silica gel in 2% acetonitrile/ethyl acetate and fractions 7-18 were concentrated to give 110 mg of the title compound. This was combined with other smaller reactions for a total of 180 mg of an oil which was triturated with ethyl acetate and ether to give 99 mg of a solid, melting point 132°-136° C.

Analysis calc'd for $C_{14}H_{18}N_6O_6S \cdot H_2O$: C, 39.95; H, 4.91; N, 17.76. Found: C, 39.95; H, 4.54; N, 18.55.

EXAMPLE 17
[3S(Z)]-[N-[[[3-[[(2-Amino-4-thiazolyl)(methoxyimino)acetyl]amino]-2-oxo-1-azetidinyl]carbonyl]methylamino]acetyl]oxy]acetic acid, 1,1-dimethylethyl ester

[3S(Z)]-[[[3-[[(2-Amino-4-thiazolyl)(methoxyimino)acetyl]amino]-2-oxo-1-azetidinyl]carbonyl]-methylamino]acetic acid, potassium salt (544 mg of a mixture containing 200 mg of the potassium salt) was dissolved in dimethylformamide (5 ml) and the volume was reduced to 1 ml. t-Butyl bromoacetate (102 μl, 0.708 mmol) was added and the reaction was stirred for 1.5 hours at room temperature. The solvents were removed, the product was extracted into acetone and the acetone was evaporated.

The residue was chromatographed on silica gel (1.1×30 cm) in hexane/ethyl acetate (3:1). Fractions 11-23 were concentrated and triturated with ether to give 130 mg of the title compound, melting point 100°-104° C.

Analysis calc'd: $C_{19}H_{26}N_6O_8S$: C, 45.78; H, 5.22; N, 16.87. Found: C, 45.61; H, 5.50; N, 15.60.

EXAMPLE 18
[3S(Z)]-2,2'-[[[3-[[(2-Amino-4-thiazolyl)(methoxyimino)acetyl]amino]-2-oxo-1-azetidinyl]carbonyl]imino]bisacetic acid, dipotassium salt (A)
(S)-2,2'-[[[3-[[(t-Butoxy)carbonyl]amino]-2-oxo-1-azetidinyl]carbonyl]imino]bisacetic acid, dibenzyl ester Dibenzyl iminodiacetate hydrochloride (699 mg) and 3A sieves were suspended in 6 ml of dry toluene and cooled to −20° C. A phosgene solution (2.9 ml of 12.5% in toluene) was added to the reaction mixture followed by the dropwise addition of pyridine (0.348 ml) with rapid stirring. The reaction was stirred at −20° C. for 1 hour and then allowed to warm to room temperature. The precipitate of pyridinium hydrochloride was filtered under argon, and the volatiles were removed from the filtrate, which was dissolved in 4 ml of tetrahydrofuran and cooled to 0° C. To this solution was added the (S)-3-[[(t-butoxy)carbonyl]amino]-2-azetidinone (372 mg) and dimethylaminopyridine (36 mg). Triethylamine (0.307 ml) was then added dropwise and the reaction was allowed to warm to room temperature and stir for 5 hours. The product was extracted from dilute aqueous hydrochloric acid with ethyl acetate. The combined organic extracts were dried with sodium sulfate and the volatiles removed. The residue was purified by flash chromatography on silica gel (eluting with 35% ethyl acetate/hexane) to yield 566 mg of the title compound as a white solid.

(B)
[3S(Z)]-2,2′-[[[3-[[(2-Amino-4-thiazolyl)(methoxyimino)acetyl]amino]-2-oxo-1-azetidinyl]carbonyl]imino]bisacetic acid, dipotassium salt (S)-2,2′-[[[3-[[(t-Butoxy)carbonyl]amino]-2-oxo-1-azetidinyl]carbonyl]imino]bisacetic acid, dibenzyl ester (566 mg, 1.08 mmol) was dissolved in 6 ml of dry tetrahydrofuran. Hydrogenolysis of the benzyl protecting groups at room temperature over 283 mg of 10% palladium on charcoal was complete after 50 minutes. The reaction mixture was filtered to remove the palladium on charcoal catalyst and the volatiles were evaporated to yield (S)-2,2′-[[[3-[[(t-butoxy)carbonyl]amino]-2-oxo-1-azetidinyl]carbonyl]imino]bisacetic acid.

Diisopropylethylamine (0.25 ml, 1.44 mmol) was added to 264 mg (1.31 mmol) of (Z)-2-amino-α-(methoxyimino)-4-thiazoleacetic acid in 3.5 ml of dimethylformamide at 23° C. The mixture was cooled to −20° C. and diphenyl chlorophosphate (0.272 ml, 1.31 mmol) was added and the resulting mixture was stirred for 30 minutes to yield a mixed anhydride.

(S)-2,2′-[[[3-[[(t-Butoxy)carbonyl]amino]-2-oxo-1-azetidinyl]carbonyl]imino]biacetic acid was cooled to −20° C. and a solution containing 5 ml of trifluoroacetic acid, 5 ml of dichloromethane, and 1 ml of anisole at 0° C. was added. After stirring at −20° C. for 1 hour, the reaction mixture was warmed to 0° C. for 2 hours. Toluene (~2 ml) was added, and the volatiles were evaporated. The residue was triturated with hexane and anhydrous ether to yield a white solid. The residue was then dissolved in 5.3 ml of dimethylformamide and upon cooling to 0° C., 0.91 ml (5.2 mmol) of diisopropylethylamine was added. The reaction mixture containing the mixed anhydride was then immediately added, and the resulting mixture was stirred at 5° C. overnight.

The volatiles were removed under vacuum, and the residue was subjected to column chromatography with water on Dowex 50X2-400 resin (K+ form). The pH of the crude product was adjusted to 2.5 with 1N HCl, and this was then subjected to chromatography on HP-20 (eluting with water, 5% acetone-water, 10% acetone-water, and 20% acetone-water) to give the impure di-acid of title compound at 0° C. and the pH was adjusted to 6 with aqueous KHCO₃. Purification of this solution by column chromatography on HP-20 (eluting with water) yielded, upon lyophilization, 112 mg of the title compound, melting point 155°–165° C., dec.

EXAMPLE 19
[3S(Z)]-1-[[3-[[(2-Amino-4-thiazolyl)(methoxyimino)acetyl]amino]-2-oxo-1-azetidinyl]carbonyl]DL-proline, potassium salt (A)
(S)-1-[[3-[[(Phenylmethoxy)carbonyl]amino]-2-oxo-1-azetidinyl]carbonyl]-DL-proline, phenylmethyl ester A solution of d,l-proline, benzyl ester (1.13 grams, 5.5 mmol) in 6 ml of dichloromethane was cooled to 0° C. and 1.2 equivalents (0.92 ml) of triethylamine (668 mg, 6.6 mmol) was added. The resulting mixture was immediately added dropwise to a solution of 20% phosgene in toluene (6 ml, 9.9 mmol) at −25° C. After stirring at −25° C. for 1 hour, the volatiles were evaporated without external heating, and the residue was redissolved in 10 ml of dichloromethane and cooled to 0° C. (S)-3-[[(Phenylmethoxy)carbonyl]amino]-2-azetidinone (1.21 grams, 5.5 mmol) and dimethylaminopyridine (67 mg, 0.55 mmol) were added to the stirring solution. Triethylamine (0.92 ml, 6.6 mmol) was added and the reaction mixture was warmed to room temperature and stirred for 24 hours. The reaction mixture was washed with water, dried over anhydrous Na₂SO₄, filtered and the dichloromethane removed in vacuo. The residue was purified by flash chromatography on silica gel 230–400 mesh (eluting with 40% ethyl acetate in hexane) yielding 1.2 grams of the title compound as a colorless oil.

(B)
[3S(Z)]-1-[[3-[[(2-Amino-4-thiazolyl)(methoxyimino)acetyl]amino]-2-oxo-1-azetidinyl]carbonyl]-DL-proline, potassium salt 1-Hydroxybenzotriazole hydrate (54 mg, 0.40 mmol) and (Z)-2-amino-α-(methoxyimino)-4-thiazole-acetic acid (80.5 mg, 0.40 mmol) were dissolved in 3 ml of dimethylformamide and cooled to 0° C. N,N-Dicyclohexylcarbodiimide (83 mg, 0.40 mmol) was added, and the mixture was warmed to room temperature. The reaction mixture was stirred for 30 minutes to yield the N-hydroxybenzotriazole ester of the acid.

(S)-1-[[3-[[(Phenylmethoxy)carbonyl]amino]-2-oxo-1-azetidinyl]carbonyl]-DL-proline, phenylmethyl dimethylformamide and p-toluenesulfonic acid monohydrate (69 mg, 0.364 mmol) was added. Hydrogenolysis of the protecting groups at room temperature over 75 mg of 10% palladium on charcoal was complete after 2.5 hours. The reaction mixture was placed under argon and cooled to 0° C. Diisopropylethylamine (47 mg, 0.364 mmol) was then added to the azetidinone followed by the above-prepared ester. After stirring at 0° C. for 2 hours, the reaction mixture was stirred at 5° C. overnight.

The volatiles were removed under vacuum. The residue was dissolved in water (5 ml), the pH adjusted to pH 6.5 with KHCO₃ and the insoluble dicyclohexylurea was removed by filtration. The residue was purified by column chromatography with water on Dowex 50X2-400 resin (K+ form) followed by chromatography on HP-20 resin (eluting with water). Lyophilization yielded 32 mg of the title compound as a colorless solid, melting point 180° C., dec.

EXAMPLE 20

[3S(Z)]-N-[[3-[[(2-Amino-4-thiazolyl)(methoxyimino)acetyl]amino]-2-oxo-1-azetidinyl]carbonyl]-N-phenylglycine (A) Benzyl N-phenylglycine To a solution of benzyl bromoacetate (4.0 ml) and aniline (2.28 ml) in 25 ml of dry dimethylformamide was added sodium acetate (2.05 g). The reaction was stirred at room temperature overnight and extracted from water with three portions of ethyl acetate. The combined organic layers were washed with water and dried over sodium sulfate. The volatiles were removed, and the residue was purified by flash column chromatography on silica gel (eluting with 10% ethyl acetate/hexane) to yield 4.54 g of benzyl N-phenylglycinate.

(B) (S)-N-[[3-[[(Phenylmethoxy)carbonyl]amino]-2-oxo-1-azetidinyl]carbonyl]-N-phenylglycine, benzyl ester Benzyl N-phenylglycine (482 mg) was dissolved in 6 ml of dry toluene and cooled to −20° C. A phosgene solution (2.9 ml of 12.5% in toluene) was added to the reaction mixture followed by the dropwise addition of pyridine (0.348 ml) with rapid stirring. The reaction was stirred for 1 hour at −20° C. and then allowed to warm to room temperature. The precipitate of pyridinium hydrochloride was filtered under argon, and the volatiles were removed from the filtrate, which was dissolved in 4 ml of tetrahydrofuran and cooled to 0° C. To this solution was added the (S)-3-[[(phenylmethoxy)carbonyl]amino]-2-azetidinone (440 mg) and dimethylaminopyridine (36 mg). Triethylamine (0.307 ml) was then added dropwise and the reaction was allowed to warm to room temperature and stir overnight. The product was extracted with ethyl acetate from dilute aqueous hydrochloric acid. The combined organic extracts were dried with sodium sulfate and the volatiles removed. The residue was purified by flash chromatography on silica gel (eluting with 45% ethyl acetate/hexane) to yield 381 mg of the title compound.

(C) [3S(Z)]-N-[[3-[[(2-Amino-4-thiazolyl)(methoxyimino)acetyl]amino]-2-oxo-1-azetidinyl]carbonyl]-N-phenylglycine Diisopropylethylamine (0.249 ml) was added to 202 mg of (Z)-2-amino-α(methoxyimino)-4-thiazoleacetic acid (containing 0.38 molar equivalents of HCl) in 3.1 ml of dimethylformamide at 23° C. The mixture was cooled to −15° C. and diphenylchlorophosphate (0.195 ml) was added, and the resulting mixture was stirred for 30 minutes to yield a mixed anhydride.

(S)-N-[[3-[[(Phenylmethoxy)carbonyl]amino]-2-oxo-1-azetidinyl]carbonyl]-N-phenylglycine, phenylmethyl ester (378 mg) was dissolved in 3.1 ml of dimethylformamide and 148 mg of p-toluenesulfonic acid monohydrate was added. Hydrogenolysis of the protecting groups at room temperature over 189 mg of 10% palladium on charcoal was complete within 1 hour. The reaction mixture was placed under inert atmosphere and cooled to 0° C.

Diisopropylethylamine (0.451 ml) was then added to the azetidinone immediately followed by the mixed anhydride, and the resulting mixture was stirred at 0° C. for 3 hours.

The reaction mixture was filtered to remove the palladium on charcoal, and the volatiles were removed under vacuum. The residue was subjected to column chromatography with water on Dowex 50X2-400 resin (K+ form) followed by chromatography on HP-20 (eluting with water and 5% acetone-water) to yield impure product upon lyophilization. This material was dissolved in water, the pH adjusted to 3.0 with dilute hydrochloric acid, and purified by column chromatography on HP-20 (eluting with water, 5% acetone-water, 10% acetone-water and 20% acetone-water) to yield 143 mg of the title compound upon lyophilization, melting point 155°–160° C., dec.

EXAMPLE 21

[3S(Z)]-[N-[[3-[[(2-Amino-4-thiazolyl)(methoxyimino)acetyl]amino]-2-oxo-1-azetidinyl]carbonyl]methylamino]acetic acid, pivaloyloxymethyl ester

[3S(Z)]-[N-[[3-[[(2-Amino-4-thiazolyl)(methoxyimino)acetyl]amino]-2-oxo-1-azetidinyl]carbonyl]methylamino]acetic acid, potassium salt (647 mg of a mixture containing 238 mg or 0.564 mmol of the potassium salt) was dissolved in dimethylformamide (10 ml) and the volume was reduced to 1 ml. Chloromethyl pivalate (122 μl, 0.846 mmol) was added and the reaction was stirred for 8 hours at room temperature. Additional chloromethyl pivalate (366 μl) was added and the reaction was run overnight.

Solvent was removed, and the residue was dissolved in water and extracted with ethyl acetate (three 20 ml portions). The organic layers were dried (Na₂SO₄), filtered and concentrated.

The residue was chromatographed on silica gel (1.5×20 cm) in hexane: ethyl acetate (3:1) and ethyl acetate. The title compound was eluted with ethyl acetate, and after removal of the solvent, weighed 140 mg. Trituration with ether gave 100 mg of a solid, melting point 108°–113° C.

EXAMPLE 22

[3S(Z)]-1-[[3-[[(2-Amino-4-thiaozlyl)(methoxyimino)acetyl]amino]-2-oxo-1-azetidinyl]carbonyl]-D-proline, potassium salt (A) 1-(t-Butyloxycarbonyl)-D-proline A solution of D-proline (0.8 g, 6.94 mmole) in 50 ml of 1:1 acetone:water was treated with triethylamine (1.05 g, 10.4 mmole) and then 1,1-dimethylethoxycarboxylic anhydride (1.77 g, 8.1 mmole). After stirring at 25° C. overnight, most of the acetone was removed in vacuo, 1 g of solid sodium bicarbonate was added and the mixture was extracted two times with ethyl acetate. The aqueous layer was acidified with 10% potassium bisulfate and extracted with ethyl acetate, the organics were dried (sodium sulfate) and evaporated to give 1.6 g of a thick oil which solidified on standing.

(B) D-proline, phenylmethyl ester 1-(t-Butyloxycarbonyl)-D-proline (6.94 mmole) in 15 ml of dry dimethylformamide was treated with 1.2 g (15 mmole) of powdered sodium bicarbonate followed by 6 g (35 mmole) of benzyl bromide at 25° C. Stirring for 15 hours resulted in complete esterification as judged by TLC (RF=0.5, silica, hexane:ethyl acetate 4:1). Solvent was removed in vacuo, and the residue was partitioned between water and ethyl acetate, the organics were dried (sodium sulfate) and diluted with hexane. Washing through a tall pad of 60–200 mesh silica removed benzyl bromide. Subsequent washing with ethyl acetate gave 2.0 g of (t-butyloxycarbonyl)-D-proline, phenylmethyl ester as a thick oil. This was dissolved in 50 ml of ethyl acetate at −10° C. and treated with hydrogen chloride gas for 5 minutes. The mixture was warmed to 25° C. over 45 minutes and evaporated to an oil. A second addition and evaporation of ethyl acetate gave a white solid. Trituration with ethyl acetate gave 1.44 g of D-proline, benzyl ester, hydrochloride, $[\alpha]_D = +45.6°$ ($H_2O$), as a white solid.

(C)
(S)-1-[[3-[[(Phenylmethoxy)carbonyl]amino]-2-oxo-1-azetidinyl]carbonyl]-D-proline, phenylmethyl ester To a slurry of dried (S)-3-[[(phenylmethoxy)carbonyl]amino]-2-azetidinone (0.44 g, 2 mmoles) in 10 ml of dry dichloromethane under argon at −10° C. was added triethylamine (0.3 g, 3 mmoles) followed by 4 ml of 12.5% phosgene in toluene (5 mmoles). After stirring for 1.5 hours at −10° C., the solvent was evaporated, and the residue taken up in dichloromethane (10 ml) and chilled to −10° C. To this was added 0.48 g (2 mmoles) of D-proline, phenylmethyl ester, hydrochloride followed by 0.4 g (4 mmoles) of triethylamine. The mixture was stirred at −10° C. for 30 minutes, then quenched and washed with 10% monobasic potassium phosphate. The organics were washed with brine, dried (sodium sulfate), and chromatographed on silica (LPS-1) in 1:1 hexane:ethyl acetate. The pure product fractions (Rf=0.23 on silica, same system) were evaporated to give 0.42 g of a thick oil.

(D)
[3S(Z)]-1-[[3-[[(2-Amino-4-thiazolyl)(methoxyimino)acetyl]amino]-2-oxo-1-azetidinyl]carbonyl]-D-proline, potassium salt (S)-1-[[3-[[(Phenylmethoxy)carbonyl]amino]-2-oxo-1-azetidinyl]carbonyl]-D-proline, phenylmethyl ester was dissolved in 8 ml of dimethylformamide in the presence of 0.18 g (1 mmole) of toluenesulfonic acid, hydrate and 0.18 g of 10% palladium on charcoal and hydrogenated at 1 atmosphere and 25° C. for 3 hours. A solution of (Z)-2-amino-α-(methoxyimino)-4-thiazoleacetic acid (0.19 g, 1 mmole) and N-hydroxybenzotriazole (0.13 g, 1 mmole) in 8 ml of dimethylformamide was chilled to 0° C. and treated with 0.19 g (1 mmole) of dicyclohexylcarbodiimide, and then stirred for 1.5 hours at 25° C. The hydrogenation mixture was chilled to 0° C. and the N-hydroxybenzotriazole ester mixture was added along with 0.18 g (1.4 mmole) of diisopropylethylamine, and the mixture was stirred at 5° C. overnight. The solvent was evaporated at 15° C. in vacuo and the residue taken up in water and filtered through Celite, pH=3.45. The pH was adjusted to 6.9 with potassium bicarbonate, and the solution passed through 30 ml of Dowex AG-50 (K+ form). The eluent was concentrated in vacuo at 15° C. and chromatographed on HP-20 in water. Product (Rf=0.45, Q-1) was lyophilized to give 219 mg of a slightly yellow powder, melting point 190°–215° C. (dec.) which analyzed correctly for the presence of 3.0 moles of water.

EXAMPLE 23

[3S(Z)]-1-[[3-[[(2-Amino-4-thiazolyl)(methoxyimino)acetyl]amino]-2-oxo-1-azetidinyl]carbonyl]-L-proline, potassium salt Following the procedure of example 22, but substituting L-proline for D-proline and utilizing 0.36 g (instead of 0.18 g) of diisopropylethyl amine, yielded the title compound, melting point 190°–220° C. (dec.).

Anal. Calc'd. for $C_{15}H_{17}N_6O_6SK.2.34H_2O$: C, 36.72; H, 4.45; N, 17.13; S, 6.54. Found: C, 36.29; H, 4.03; N, 17.16; S, 6.45.

EXAMPLE 24

[3S(Z)]-1-[[3-[[(2-Amino-4-thiazolyl)[(1-carboxy-1-methylethoxy)imino]acetyl]amino]-2-oxo-1-azetidinyl]carbonyl]-L-proline (S)-1-[[3-[[(Phenylmethoxy)carbonyl]amino]-2-oxo-1-azetidinyl]carbonyl]-L-proline, phenylmethyl ester (0.45 g, 1 mmole; prepared as described in examples 22 and 23) was hydrogenated at 1 atmosphere of hydrogen and 25° C. over 0.2 g of 10% palladium on charcoal in the presence of 0.19 g (1 mmole) of p-toluenesulfonic acid for 3 hours. (Z)-2-Amino-α-[[2-(diphenylmethoxy)-1,1-dimethyl-2-oxoethoxy]imino]-4-thiazoleacetic acid (0.47 g, 1 mmole) and N-hydroxybenzotriazole (0.15 g, 1 mmole) in 4 ml of dimethylformamide at 0° C. was treated with 0.21 g (1 mmole) of dicyclohexylcarbodiimide and the mixture warmed to 20° C. for 2 hours. The hydrogenolysis mixture was chilled to 0° C. and treated with the solution of N-hydroxybenzotriazole ester, along with 0.14 g (1.1 mmole) of diisopropylethylamine. After 14 hours at 5° C., the mixture was evaporated at 15° C. in vacuo and diluted with water. The grey slurry was filtered on Celite and the pad washed with acetone which was added to the aqueous filtrate. The pH of the mixture (3.45) was adjusted to 6.75 with potassium bicarbonate, and the mixture was washed through a Dowex AG-50 (K+) column in 20% acetone-water. The product fractions (Rf=0.81) were combined and chromatographed on HP-20 in a water-acetone gradient. Those fractions containing mostly pure product were combined, evaporated and lyophilized to yield 0.28 g of the ester, potassium salt of the title compound.

The ester (0.28 g, 0.39 mmole) was slurried in 6 ml of anisole at 0° C. and 10 ml of cold trifluoroacetic acid was added and stirred for 1.5 hours. The mixture was evaporated in the cold (5° C.) and water and hexane were added, the organics being discarded. The aqueous layer was chromatographed on HP-20 with a water, acetone:water (1:1) gradient. Lyophilization gave 54 mg of white powder analyzing low in nitrogen. Rechromatography on HP-20 gave 24 mg of the title compound which analyzed for the presence of 0.82 moles of water, melting point 200°–220° C. (dec.).

Anal. Calc'd. for $C_{12}H_{22}N_6O_8S.0.82H_2O$: C, 43.48; H, 4.79; N, 16.90; S, 6.45. Found: C, 43.48; H, 4.60; N, 16.21; S, 6.27.

EXAMPLE 25

(trans)-1-[[3S(Z)]-3-[[(2-Amino-4-thiazolyl)(methoxyimino)acetyl]amino]-2-oxo-1-azetidinyl]carbonyl]-4-hydroxy-L-proline, potassium salt (A)

(trans)-1-[[3S-[[(Phenylmethoxy)carbonyl]amino]-2-oxo-1-azetidinyl]carbonyl]-4-hydroxy-L-proline, phenylmethyl ester A slurry of (S)-3-[[(phenylmethoxy)carbonyl]amino]-2-azetidinone (0.44 g, 2 mmole) in 10 ml of dichloromethane was chilled to −10° C. under argon and treated with 0.3 g (3 mmoles) of triethylamine followed by 3.0 ml (3.75 mmoles) of 12.5% phosgene in toluene. After 2 hours at −10° C., the mixture was evaporated in vacuo at 10° C., the residue taken up in 15 ml of dichloromethane at 0° C., and 0.51 g (2 mmole) of 4(R)-hydroxy-L-proline, phenylmethyl ester, hydrochloride added, followed by 0.4 g (4 mmole) of triethylamine. After 30 minutes, 10 ml of 10% monobasic potassium phosphate was added, and the organics were separated and washed with brine. Chromatography on silica (LPS-1) in ethyl acetate gave the title compound (0.3 g, Rf=0.57 (ethyl acetate)) as a thick oil.

(B)

(trans)-1-[[3S(Z)]-3-[[(2-Amino-4-thiazolyl)(methoxyimino)acetyl]amino]-2-oxo-1-azetidinyl]carbonyl]-4-hydroxy-L-proline, potassium salt (trans)-1-[[3S-[[(Phenylmethoxy)carbonyl]amino]-2-oxo-1-azetidinyl]carbonyl]-4-hydroxy-L-proline, phenylmethyl ester (0.3 g, 0.64 mmole) in 6 ml of dimethylformamide with 0.13 g (0.68 mmole) of p-toluenesulfonic acid and 0.2 g of 10% palladium on charcoal was hydrogenated at 1 atmosphere and 25° C. for 3 hours. 0.13 g (0.64 mmole) of (Z)-2-amino-α-(methoxyimino)-4-thiazoleacetic acid in 4 ml of dimethylformamide at 0° C. was treated with 0.1 g (0.64 mmole) of N-hydroxybenzotriazole and 0.13 g (0.64 mmole) of dicyclohexylcarbodiimide. After 2 hours at 25° C., the N-hydroxybenzotriazole ester mixture was chilled to 0° C. and added to the hydrogenation mixture at 0° C. After the resulting mixture was stirred at 5° C. for 14 hours, it was evaporated in vacuo at 15° C. The residue was taken up in water, filtered (pH=3.45), and adjusted to pH=6.75 with potassium bicarbonate. This solution was passed through a Dowex AG-50 (K+) column in water and lyophilized to a powder. This was chromatographed on HP-20, and the partially purified product lyophilized, taken up in a small amount of water and adjusted to pH=2.5. Two HP-20 chromatographies using a water-50% acetone/water gradient gave still impure product. Conversion back to the potassium salt (pH=6.9) with potassium bicarbonate and HP-70 chromatography gave 70 mg of nearly pure product. Chromatography on a 7 g Sephadex (LH-20) column in water gave product which was >80% pure by HI, and whose microanalysis was consistent with the presence of 2.16 moles of water and up to 19% of the dipotassium salt of the product of β-lactam ring opening. The yield was 35 mg., melting point 200°-220° C., dec.

Anal. Calc'd. for $C_{15}H_{17}N_6O_7SK.2.16H_2O$: C, 35.04; H, 4.22; N, 16.35; S, 6.23. Found: C, 35.04; H, 3.82; N, 16.07; S, 6.06.

EXAMPLE 26

[3S(Z)]-1-[[3-[[(2-Amino-4-thiazolyl)[(1-carboxy-1-methylethoxy)imino]acetyl]amino]-2-oxo-1-azetidinyl]carbonyl]-D-proline Following the procedure of example 24, but substituting (S)-1-[[3-[[(phenylmethoxy)carbonyl]amino]-2-oxo-1-azetidinyl]carbonyl]-D-proline, phenylmethyl ester for the corresponding L-proline derivative, yielded the title compound, melting point 180°–210° C., which analyzed for the presence of 1.07 moles of water.

Anal. Calc'd. for $C_{18}H_{22}N_6O_8S.1.07H_2O$: C, 43.09; H, 4.85; N, 16.75; S, 6.39. Found: C, 43.09; H, 4.57; N, 16.05; S, 5.98.

EXAMPLE 27

1-[[(3S)-3-(Benzoylamino)-2-oxo-1-azetidinyl]carbonyl]-L-proline

A solution of (S)-1-[[3-[[(phenylmethoxy)carbonyl]amino]-2-oxo-1-azetidinyl]carbonyl]-L-proline, phenylmethyl ester (0.35 g, 0.78 mmole; prepared as described in examples 22 and 23) in 4.5 ml of dimethylformamide with 0.15 g (0.8 mmole) of p-toluenesulfonic acid and 0.2 g of 10% palladium on charcoal was hydrogenated at 1 atmosphere and 25° C. for 3 hours. The solution was chilled to 0° C. and treated with 0.3 g (2.3 mmoles) of diisopropylethylamine followed by 0.16 g (1.1 mmole) of benzoyl chloride, and stirred at 5° C. for 3½ days. Water (10 ml) was added to the dimethylformamide solution and the slurry filtered on Celite. The pH was 3.35, and this was adjusted to 2.0 with dilute hydrochloric acid. The solution was extracted with ethyl acetate, saturated with solid sodium chloride and extracted again. The organics were dried (sodium sulfate) and evaporated to a yellow oil which showed one major component by TLC (Rf=0.56) with some less polar impurities. The oil was dissolved in dichloromethane and diluted to cloud with hexane. Scratching gave 70 mg of a white solid, melting point 148°–151° C.

A 20 mg sample of this solid was dissolved in 0.5 ml of acetone and diluted with 0.5 ml of water. Standing in an open vial at 25° C. overnight gave large, well-formed needles, 10 mg, suitable for x-ray analysis, which were found to be monohydrated.

Anal. Calc'd. for $C_{16}H_{17}N_3O_5.0.4H_2O$: C, 56.83; H, 5.29; N, 12.43. Found: C, 56.83; H, 5.07; N, 12.43.

EXAMPLE 28

(cis)-1-[[3S(Z)]-3-[[(2-Amino-4-thiazolyl)(methoxyimino)acetyl]amino]-2-oxo-1-azetidinyl]carbonyl]-4-hydroxy-L-proline, potassium salt (A)

(cis)-1-[[3S-[[(Phenylmethoxy)carbonyl]amino]-2-oxo-1-azetidinyl]carbonyl]-4-hydroxy-L-proline, phenylmethyl ester A slurry of 3S-[[(phenylmethoxy)carbonyl]amino]-2-azetidinone (0.44 g, 2.0 mmole) and 0.3 g (3 mmoles) of triethylamine in 15 ml dichloromethane at −10° C. under argon was treated with 3.0 ml (3.75 mmoles) of 12.5% phosgene in toluene and the resultant mixture stirred at −10° C. for 2 hours. Solvents were removed in vacuo at 10° C. and the residue taken up in 20 ml of dichloromethane at 0° C. and treated with 0.51 g (2 mmole) of 4(S)-hydroxy-L-proline, phenylmethyl ester followed by 0.4 g (4 mmole) of triethylamine. After 1.5 hours at 0° C., the mixture was washed with monobasic potassium phosphate, water and brine, dried (sodium sulfate), and chromatographed on silica (LPS-1) in ethyl acetate:dichloromethane, 6:1. Product fractions (Rf=0.46, ethyl acetate) were evaporated to give the title compound as a colorless oil, 0.36 g.

(B)
(cis)-1-[[3S(Z)]-[3-[[(2-Amino-4-thiazolyl)(methoxyimino)acetyl]amino]-2-oxo-1-azetidinyl]carbonyl]-4-hydroxy-L-proline, potassium salt (cis)-1-[[3S-[[(Phenylmethoxy)carbonyl]amino]-2-oxo-1-azetidinyl]carbonyl]-4-hydroxy-L-proline, phenylmethyl ester (0.36 g, 0.76 mmole) in 8 ml of dimethylformamide with 0.15 g (0.79 mmole) of p-toluenesulfonic acid and 0.25 g of 10% palladium on charcoal was hydrogenated at 1 atmosphere and 25° C. for 2.5 hours. 0.16 g (0.79 mmole) of (Z)-2-amino-$\alpha$-(methoxyimino)-4-thiazoleacetic acid and 0.12 g (0.78 mmole) of N-hydroxybenzotriazole in 5 ml of dimethylformamide at 0° C. was treated with 0.16 g (0.79 mmole) of dicyclohexylcarbodiimide, and the temperature allowed to come to 25° C. over 2 hours. The solutions were chilled to 0° C., combined, and treated with 0.09 g (0.7 mmole) of diisopropylethylamine. After 14 hours at 5° C., the solvent was removed in vacuo at 10° C. and the residue was slurried in water and filtered. The pH of the filtrate (pH=3.30) was adjusted to 6.75 with potassium bicarbonate and passed through a Dowex AG-50 (K+) column. The product fractions (Rf=0.37) were partially evaporated at 10° C. then chromatographed on HP-20 in water. Lyophilization of early, middle, and late pure product fractions gave a total of 0.21 g of final product. The more intense middle cut, 0.135 g, melting point 230°–240° C. (dec.) was submitted for analysis, and was found to contain 2.09 moles of water. 400 MHz NMR showed this sample to contain 5–10% of p-toluenesulfonic acid potassium salt, accounting for the low analysis.

Anal. Calc'd. for $C_{15}H_{17}N_6O_7SK.2.09H_2O$: C, 35.87; H, 4.25; N, 16.73; S, 6.38; K, 7.78. Found: C, 35.87; H, 3.85; N, 15.94; S, 6.33; K, 8.25.

EXAMPLE 29

(S)-4-[(Aminocarbonyl)oxy]-1-[[(S)-3-[[(2-amino-4-thiazolyl)(methoxyimino)acetyl]amino]-2-oxo-1-azetidinyl]carbonyl]-L-proline, potassium salt (A)
(cis)-1-[[3S-[[(Phenylmethoxy)carbonyl]amino]-2-oxo-1-azetidinyl]carbonyl]-4-[(aminocarbonyl)oxy]-L-proline, phenylmethyl ester A solution of (cis)-1-[[3S-[[(phenylmethoxy)carbonyl]amino]-2-oxo-1-azetidinyl]carbonyl]-4-hydroxy-L-proline, phenylmethyl ester (0.26 g, 0.56 mmole; see example 28A) in 8 ml of dry dichloromethane under argon at −10° C. was treated with 0.07 ml of chlorosulfonyl isocyanate (d=1.626, 0.11 g, 0.81 mmole) and stirred at this temperature for 20 minutes. A solution of 0.1 g of sodium sulfite in 1 ml of water was added to give a milky suspension. Stirring for 1 hour at 25° C. and adding more water and sodium sulfite did not change the TLC. Water and a large volume of ethyl acetate (200 ml) was added with vigorous shaking to dissolve a heavy oil. The organic phase contained material (Rf=0.49) virtually identical by TLC to the starting alcohol. Drying (sodium sulfate) and evaporation gave 0.32 g of a white solid.

A solution of the above solid (0.32 g, 0.56 mmole) in 8 ml of dimethylformamide with 0.12 g (0.62 mmole) of p-toluenesulfonic acid and 0.2 g of 10% palladium on charcoal was hydrogenated at 25° C. for 4 hours. A solution of 0.13 g (0.64 mmole) of (Z)-2-amino-$\alpha$-(methoxyimino)-4-thiazoleacetic acid and 1-hydroxybenzotriazole (0.1 g, 0.67 mmole) in 4 ml of dimethylformamide at 0° C. was treated with 0.13 g (0.63 mmole) of dicyclohexylcarbodiimide and warmed to 25° C. for 2 hours. The two solutions were chilled to 0° C., combined and treated with 0.1 g (0.78 mmole) of diisopropylethylamine. After 15 hours at 5° C., the mixture was evaporated in vacuo, taken up in water, filtered, and the pH of 3.05 adjusted to 6.90 with potassium bicarbonate. This solution was passed through Dowex AG-50 (K+), the product fractions (Rf=0.49) combined and partially evaporated, and the resultant mixture chromatographed on HP-20 in water. Product fractions were combined and lyophilized to give 0.14 g of the final product, melting point 225°–240° C. (dec.), which analyzed for 2.45 moles of water. NMR indicates the presence of 4–5% of p-toluenesulfonic acid.

Anal. Calc'd. for $C_{16}H_{18}N_7O_8SK.2.45H_2O$: C, 34.83; H, 4.18; N, 17.77; S, 5.81; K, 7.09. Found: C, 34.83; H, 3.75; N, 17.22; S, 5.69; K, 7.17.

EXAMPLE 30

(S)-1-[[(S)-3-[(Z)-[(2-Amino-4-thiazolyl)[(carboxymethoxy)imino]acetyl]amino]-2-oxo-1-azetidinyl]carbonyl]-2-azetidinecarboxylic acid (A)
(S)-1-[[(S)-3-[[(Phenylmethoxy)carbonyl]amino]-2-oxo-1-azetidinyl]carbonyl]-2-azetidinecarboxylic acid, phenylmethyl ester A slurry of (S)-3-[[(phenylmethoxy)carbonyl]amino]-2-azetidinone (0.78 g, 3.54 mmole) in dry dichloromethane was warmed briefly to 50° C. and then cooled to −5° C. Triethylamine (0.354 g, 3.54 mmole) and phosgene (5.7 ml of 12.5% phosgene/toluene) were added and the reaction was stirred at −5° C. for 2 hours. The reaction was concentrated to a residue and fresh dichloromethane was added. After the solution was cooled to −50° C., triethylamine (0.714 g, 7.08 mmole) and azetidine-2-carboxylic acid, benzyl ester hydrochloride (0.8 g, 3.54 mmole) were added. The reaction was stirred at −5° C. for 45 minutes. The reaction mixture was poured into 10% monobasic potassium phosphate and the dichloromethane layer was separated and washed with water and brine. After drying over sodium sulfate the solvent evaporated. The crude oil was flash chromatographed on silica (LPS-1) eluting with ethyl-/acetate:hexane (1:1). Fractions containing pure compound were concentrated to give 0.622 g of the title compound.

(B)
(S)-[[(S)-3-[(Z)-[(2-Amino-4-thiazolyl)[(carboxymethoxy)imino]acetyl]amino]-2-oxo-1-azetidinyl]carbonyl]-2-azetidinecarboxylic acid A mixture of (S)-1-[[(S)-3-[[(phenylmethoxy)carbonyl]amino]-2-oxo-1-azetidinyl]carbonyl]-2-azetidinecarboxylic acid, phenylmethyl ester (0.31 g, 0.71 mmole), p-toluenesulfonic acid (0.13 g, 0.71 mmole) and 10% palladium on charcoal (0.15 g) in dimethylformamide were stirred at room temperature under a stream of hydrogen for three hours. To a mixture of (Z)-2-amino-$\alpha$-[[2-(diphenylmethoxy)-2-oxoethoxy]imino]-4-thiazoleacetic acid (290 mg, 0.71 mmole) and N-hydroxybenzotriazole (96 mg, 0.71 mmole) in dimethylformamide at 0° C. was added dicyclohexylcarbodiimide (146 mg, 0.71 mmole). This was stirred at room temperature for 2 hours to form the N-hydroxybenzotriazole ester. The hydrogenated reaction mixture was cooled to 0° C. and diisopropylethylamine (0.12 ml, 0.71 mmole) was added followed immediately by the addition of the N-hydroxybenzotriazole ester mixture. This reaction mixture was stirred at 0° C. to 5° C. for 16 hours. The dimethylformamide was then removed under vacuum at room temperature. The residue was diluted with acetone and filtered through Celite. An equal volume of water was added and the solution was loaded onto an AG-50 (K+) column and eluted with acetone:water (1:1). Fractions containing product were adjusted to pH 6.7 and then concentrated to a slurry. The slurry was added to an HP-20 column and eluted with water until the N-hydroxybenzotriazole was removed and then eluted with an acetone/water gradient to remove the product from the column. The product fractions were lyophilized to a residue.

The lyophilate was added to a chilled solution of anisole/trifluoroacetic acid (6 ml/10 ml) and stirred at 0° C. for 1 hour. The solution was concentrated under vacuum. Water and hexane were added and the phases were separated. The aqueous layer was adjusted from pH 1.5 to 2.5 with 1N potassium bicarbonate and then chromatographed on an HP-20 column eluting first with water and then with an acetone/water gradient. Fractions containing pure product were lyophilized to a white solid (49.1 mg), melting point >200° C., dec.

Anal. Calc'd. for $C_{15}H_{16}N_6O_8S \cdot 1.3H_2O$: C, 38.82; H, 4.04; N, 18.11; S, 6.91. Found: C, 38.82; H, 3.70; N, 17.79; S, 6.59.

EXAMPLE 31

(S)-1-[[(S)-3-[[(Z)-(2-Amino-4-thiazolyl)[(1-carboxy-1-methylethoxy)imino]acetyl]amino]-2-oxo-1-azetidinyl]-carbonyl]-2-azetidinecarboxylic acid A mixture of (S)-1-[[(S)-3-[[(phenylmethoxy)carbonyl]amino]-2-oxo-1-azetidinyl]carbonyl]-2-azetidinecarboxylic acid, phenylmethyl ester (0.31 g, 0.71 mmole; see example 30A), p-toluenesulfonic acid (0.13 g, 0.71 mmole) and 10% palladium on charcoal (0.15 g) in dimethylformamide were stirred at room temperature under a stream of hydrogen for three hours. To a mixture of (Z)-2-amino-α-[[2-(diphenylmethoxy)-1,1-dimethyl-2-oxoethoxy]imino]-4-thiazoleacetic acid (330 mg, 0.71 mmole) and N-hydroxybenzotriazole (96 mg, 0.71 mmole) in dimethylformamide at 0° C. was added dicyclohexylcarbodiimide (146 mg, 0.71 mmole). This was stirred at room temperature for 2 hours to form the N-hydroxybenzotriazole ester. The hydrogenation reaction mixture was cooled to 0° C. and diisopropylethylamine (0.12 ml, 0.71 mmole) was added followed immediately by the addition of the N-hydroxybenzotriazole ester mixture. This reaction mixture was stirred at 0° C. to 5° C. for 16 hours. The dimethylformamide was then removed under vacuum at room temperature. The residue was diluted with acetone and filtered through Celite. An equal volume of water was added and the solution was loaded onto an AG-50 (K+) column and eluted with acetone:water (1:1). Fractions containing product were adjusted to pH 6.7 and then concentrated to a slurry. The slurry was added to an HP-20 column and eluted with water until the N-hydroxybenzotriazole was removed and then eluted with an acetone/water gradient to remove the product from the column. The product fractions were lyophilized to a residue.

The lyophilate was added to a chilled solution of anisole/trifluoroacetic acid (6 ml/10 ml) and stirred at 0° C. for 1 hour. The solution was concentrated under vacuum. Water and hexane were added and the phases were separated. The aqueous layer was adjusted from pH 1.9 to 2.5 with 1N potassium bicarbonate and then chromatographed on an HP-20 column eluting first with water and then with an acetone/water gradient. Fractions containing pure product were lyophilized to a white solid (94 mg), melting point >230° C., dec.

Anal. Calc'd. for $C_{17}H_{20}N_6O_8S \cdot 1.6H_2O$: C, 40.98; H, 4.90; N, 16.87; S, 6.41. Found: C, 40.98; H, 4.11; N, 16.74; S, 6.31.

EXAMPLE 32

(S)-1-[[3S(Z)]-[3-[[(2-Amino-4-thiazolyl)(methoxyimino)acetyl]amino]-2-oxo-1-azetidinyl]carbonyl]-2-azetidinecarboxylic acid (A) L-Azetidine-2-carboxylic acid, phenylmethyl ester L-Azetidine-2-carboxylic acid (0.88 g, 8.7 mmole) in 30 ml of 1:1 acetone:water was treated with 1.32 g (13.1 mmole) of triethylamine followed by 2.22 g (10.1 mmole) of 1,1-dimethylethoxycarboxylic anhydride. After 24 hours at 25° C., acetone was evaporated in vacuo, 1.0 g of sodium bicarbonate and 50 ml water were added, and the mixture was extracted with ethyl acetate. The aqueous layer was acidified (10% potassium bisulfate) and extracted with ethyl acetate. Drying (sodium sulfate) and evaporation gave 1.8 g of a low melting solid. This was dissolved in 6 ml of dimethylformamide and treated with 1.5 g of sodium bicarbonate and 6 g of benzyl bromide. Stirring at 25° C. for 14 hours caused complete reaction. Water and ethyl acetate were added, layers separated, and organics washed (water), dried (sodium sulfate) and evaporated to an oil. Chromatography on silica in hexane:ethyl acetate (1:1) gave 1-[(1,1-dimethylethoxy)carbonyl]-L-azetidine-2-carboxylic acid, phenylmethyl ester (1.8 g) as a colorless oil. This oil was treated with hydrogen chloride gas at 0° C. in 50 ml of ethyl acetate for 5 minutes, and warmed to 25° C. for 1 hour. Evaporation gave an oil which solidified with the addition of ether. The solid was washed with ether and ethyl acetate, and dried in vacuo to give 1.28 g of the title compound.

(B) (S)-1-[[(S)-3-[[(Phenylmethoxy)carbonyl]amino]-2-oxo-1-azetidinyl]carbonyl]-2-azetidinecarboxylic acid, phenylmethyl ester A slurry of (S)-3-[[(phenylmethoxy)carbonyl]amino]-2-azetidinone (0.44 g, 2 mmole) in 10 ml of dichloromethane was chilled to −10° C. under argon and treated with 0.3 g (3 mmoles) of triethylamine, followed by 3 ml (3.75 mmoles) of 12.5% phosgene in toluene. After 2 hours at −10° C., the mixture was evaporated in vacuo at 10° C., the residue taken up in 15 ml of dichloromethane at −10° C., and 0.4 g (4 mmole) of triethylamine was added followed by 0.45 g (2 mmole) of L-azetidine-2-carboxylic acid, phenylmethyl ester. After 30 minutes at 0° C., the reaction was extracted with 10% monobasic potassium phosphate and water, dried (sodium sulfate) and chromatographed on silica (LPS-1) (hexane:ethyl acetate, 1:1), to give the title compound (Rf=0.71 in ethyl acetate), 0.34 g.

(C)
(S)-1-[[3S(Z)]-[3-[[(2-Amino-4-thiazolyl)(methoxyimino)acetyl]amino]-2-oxo-1-azetidinyl]carbonyl]-2-azetidinecarboxylic acid (S)-1-[[(S)-3-[[(Phenylmethoxy)carbonyl]amino]-2-oxo-1-azetidinyl]carbonyl]-2-azetidinecarboxylic acid, phenylmethyl ester (0.34 g, 0.78 mmole) in 0.5 ml of dimethylformamide with 0.15 g (0.79 mmole) of p-toluenesulfonic acid hydrate and 0.2 g of 10% palladium on charcoal was hydrogenated at 1 atmosphere and 25° C. for 3 hours. (Z)-2-Amino-α-(methoxyimino)-4-thiazoleacetic acid (0.14 g, 0.7 mmoles) and 0.11 g (0.72 mmoles) of N-hydroxybenzotriazole in 4 ml of dimethylformamide at 0° C. was treated with 0.14 g (0.7 mmoles) of dicyclohexylcarbodiimide and warmed to 25° C. for 30 minutes. Both reactions were chilled to 0° C. and combined with 0.11 g (0.85 mmole) of diisopropylethylamine, and the mixture stirred for 14 hours at 5° C. Evaporation in vacuo at 15° C., slurrying in water, and filtering through a Celite pad gave a solution (pH 3.45). The pH was adjusted to 6.9 with potassium bicarbonate and this solution was passed through a Dowex AG-50 (K+) column. The eluate was concentrated in vacuo at 15° C. and chromatographed on HP-20 in water. The product (Rf=0.4) fractions were lyophilized to give 146 mg of the potassium salt of the title compound which was shown by microanalysis and NMR to contain 1 mole of the potassium salt of p-toluenesulfonic acid.

A solution of the salt in water was adjusted to pH 2.45 with dilute hydrochloric acid and chromatographed on HP-20 with a water-20% acetone/water gradient. Product fractions were partially evaporated, then lyophilized to give 60 mg of final product, melting point 170°–200° C. (dec.), which analyzed for the presence of 0.93 mmoles of water.

Anal. Calc'd. for $C_{14}H_{16}N_6O_6S \cdot 0.93H_2O$: C, 40.70; H, 4.35; N, 20.34; S, 7.76. Found: C, 40.70; H, 4.57; N, 19.90; S, 7.65.

EXAMPLE 33

[3S(Z)]-1-[[3-[[(2-Amino-4-thiazolyl)(methoxyimino)acetyl]amino]-2-oxo-1-azetidinyl]carbonyl]-2-piperidinecarboxylic acid, potassium salt (A) 1-[(1,1-Dimethylethoxy)carbonyl]-D,L-pipecolinic acid D,L-Pipecolinic acid (2.6 g, 0.02 mole) in 40 ml of 50% aqueous acetone was treated with 2.6 g (0.026 mole) of triethylamine followed by 4.8 g (0.022 mole) of 1,1-dimethylethoxycarboxylic anhydride at 20° C. After 24 hours, acetone was evaporated and water, ethyl acetate and 2 g of sodium bicarbonate were added. The organic layer was discarded and the aqueous layer was acidified (sodium sulfate), extracted (ethyl acetate) and evaporated to give 4.2 g of a white solid.

(B) D,L-Pipecolinic acid, phenylmethyl ester, hydrochloride

1-[(1,1-Dimethylethoxy)carbonyl]-D,L-pipecolinic acid (2 g, 8.7 mmole) in 6 ml of dimethylformamide and 1.5 g of sodium bicarbonate was treated with 6.0 g of benzyl bromide for 2½ days at 25° C. Evaporation and partitioning between ethyl acetate and water gave a crude product which was separated by silica (LPS-1) chromatography in hexane/ethyl acetate, 6:1. The colorless oil thus obtained (Rf=0.51, ethyl acetate) was treated at 0° C. in 50 ml of ethyl acetate with hydrogen chloride gas. Evaporation gave a solid which was triturated with ethyl acetate, filtered, and dried in vacuo to give 2.06 g of the title compound.

(C)
(3S)-1-[[3-[[(Phenylmethoxy)carbonyl]amino]-2-oxo-1-azetidinyl]carbonyl]-2-piperidinecarboxylic acid, phenylmethyl ester A slurry of (S)-3-[[(phenylmethoxy)carbonyl]amino]-2-azetidinone (1.32 g, 6 mmoles) in 50 ml of dichloromethane was treated with 0.9 g (9 mmoles) of triethylamine and chilled to −10° C. Phosgene (9.0 ml of 12.5% in toluene, 11.3 mmoles) was added and after 2 hours at −10° C., the mixture was evaporated at 10° C. in vacuo. The residue was dissolved in 50 ml of dry dichloromethane at −5° C. and treated with 1.2 g (12 mmoles) of triethylamine and 1.53 g (6 mmoles) of D,L-pipecolinic acid, phenylmethyl ester, hydrochloride. This mixture was allowed to warm to 25° C. over 3 hours, washed with 10% monobasic potassium phosphate and water, dried (sodium sulfate) and chromatographed on silica (LPS-1) in hexane:ethyl acetate 1:1, to give 1.1 g of the title compound as a colorless oil.

(D)
[3S(Z)]-1-[[3-[[(2-Amino-4-thiazolyl)(methoxyimino)acetyl]amino]-2-oxo-1-azetidinyl]carbonyl]-2-piperidinecarboxylic acid, potassium salt (3S)-1-[[3-[[(Phenylmethoxy)carbonyl]amino]-2-oxo-1-azetidinyl]carbonyl]-2-piperidinecarboxylic acid, phenylmethyl ester (1.1 g, 2.4 mmoles) was hydrogenated at 25° C. in 20 ml of dimethylformamide in the presence of 0.46 g (2.4 mmole) of p-toluenesulfonic acid and 0.8 g of 10% palladium on charcoal for 4 hours. (Z)-2-Amino-α-(methoxyimino)-4-thiazoleacetic acid (0.48 g, 2.4 mmoles) and 0.40 g (2.4 mmoles) of N-hydroxybenzotriazole in 7 ml of dimethylformamide at 0° C. and treated with 0.49 g (2.4 mmoles) of dicyclohexylcarbodiimide and allowed to come to 25° C. over 2 hours. Both solutions were chilled to 0° C., combined, and treated with 0.31 g (2.4 mmoles) of diisopropylethylamine. After 15 hours at 5° C., the solvents were evaporated at 10° C. in vacuo to a gum. This was taken up in water, filtered (Celite pad), and the pH of 3.5 adjusted to pH 6.5 with potassium bicarbonate. Filtering through Dowex AG-50 (K+) and lyophilization gave 2.7 g of a beige solid. Chromatography on HP-20 in water and combination of the most intense product spots (Rf=0.69) gave, on lyophilization, 0.275 g of final product, melting point 205°–225° C. (dec.), which analyzed for the presence of 2.28 moles of water.

Anal. Calc'd. for $C_{16}H_{19}N_6O_6SK \cdot 2.28H_2O$: C, 38.15; H, 4.72; N, 16.68; S, 6.37; K, 7.78. Found: C, 38.15; H, 4.10; N, 16.68; S, 6.12; K, 8.38.

EXAMPLE 34

[3S(Z)]-[(2-Amino-2-oxoethyl)[[3-[[(2-amino-4-thiazolyl)(methoxyimino)acetyl]amino]-2-oxo-1-azetidinyl]carbonyl]amino]acetic acid, potassium salt (A)
(3S)-[(2-Amino-2-oxoethyl)[[3-[[(t-butyloxy)carbonyl]amino]-2-oxo-1-azetidinyl]carbonyl]amino]acetic acid (S)-2,2'-[[[3-[[(t-Butyloxy)carbonyl]amino]-2-oxo-1-azetidinyl]carbonyl]imino]bisacetic acid, diphenyl ester (1.575 g, 3 mmol; see example 18A) was dissolved in 18 ml of dry tetrahydrofuran. Hydrogenolysis of the benzyl protecting groups at room temperature over 788 mg of 10% palladium on charcoal was complete after 50 minutes. The reaction mixture was filtered to remove the palladium on charcoal catalyst, toluene (~3 ml) was added, and the volatiles were evaporated to yield the presumed diacid of the azetidinone starting material.

The diacid was dissolved in 45 ml of dry tetrahydrofuran and a solution of dicyclohexylcarbodiimide (681 mg, 3.3 mmol) in 12 ml of dry tetrahydrofuran was added dropwise to the stirring reaction mixture at room temperature. The reaction mixture was stirred for 70 minutes at room temperature. The solvent volume was reduced to ~24 ml by evacuation and the reaction mixture was cooled to 0° C. An aqueous 15% diammonium phosphate solution (30 ml) was added, and the mixture was stirred vigorously for 2 hours. The tetrahydrofuran was evaporated, the reaction mixture was cooled to 0° C., and the pH was adjusted to 2.5 with 1N hydrochloric acid. Purification of this crude product by column chromatograph on HP-20 (eluting with water, 5% acetone-water, and 10% acetone-water) yielded upon lyophilization, 588 mg of the title compound.

(B)

[3S(Z)]-[(2-Amino-2-oxoethyl)[[3-[[(2-amino-4-thiazolyl)(methoxyimino)acetyl]amino]-2-oxo-1-azetidinyl]carbonyl]amino]acetic acid, potassium salt Diisopropylethylamine (0.270 ml, 1.55 mmol) was added to 219 mg (1.02 mmol) of (Z)-2-amino-4-(methoxyimino)-4-thiazoleacetic acid (containing 0.38 molar equivalents of hydrochloric acid) in 3.4 ml of dimethylformamide at 23° C. The mixture was cooled to −20° C., diphenylchlorophosphate (0.211 ml, 1.02 mmol) was added, and the resulting mixture was stirred for 30 minutes to yield a mixed anhydride.

(3S)-[(2-Amino-2-oxoethyl)[[3-[[(t-butyloxy)carbonyl]amino]-2-oxo-1-azetidinyl]carbonyl]amino]acetic acid (294 mg, 0.85 mmol) was cooled to 0° C. and a solution containing 4 ml of trifluoroacetic acid, 4 ml of dichloromethane and 0.8 ml of anisole at 0° C. was added. After stirring at 0° C. for 2 hours, toluene (~2 ml) was added, and the volatiles were evaporated. The residue was triturated with hexane and anhydrous ether to yield a white solid. The residue was then dissolved in 3.4 ml of dimethylformamide and upon cooling to 0° C., 0.491 ml (2.82 mmol) of diisopropylethylamine was added. The reaction mixture containing the mixed anhydride was immediately added, and the resulting mixture was stirred at 0° C. for 3 hours.

The volatiles were removed under vacuum, and the residue was subjected to column chromatography with water on Dowex 50X2-400 resin (K+ form). The pH of the crude product was adjusted to 2.5 with 1N hydrochloric acid, and this was subjected to chromatography on HP-20 (eluting with water, 5% acetone-water, and 10% acetone-water) to give the impure acid of the title compound. The crude product was dissolved in ~4 ml of water at 0° C. and the pH was adjusted to 6.5 with aqueous potassium bicarbonate. Purification of this solution by column chromatography on HP-20 (eluting with water) yielded, upon lyophilization, 215 mg of the title compound, melting point 187°–195° C., dec.

Anal. Calc'd. for $C_{14}H_{16}N_7O_7SK$: C, 36.12; H, 3.46; N, 21.06. Found: C, 31.92; H, 3.58; N, 17.94.

EXAMPLE 35

[3S(Z)]-[[[3-[[(2-Amino-4-thiazolyl)(methoxyimino)acetyl]amino]-2-oxo-1-azetidinyl]carbonyl](2,2-dimethoxyethyl)amino]acetic acid, potassium salt (A)

(2,2-Dimethoxyethyl)(2-phenylmethoxy-2-oxoethyl)amine

A solution of aminoacetaldehyde dimethyl acetal (2.2 ml, 0.04 mole) in ether (10 ml) was cooled to 0° C. Benzyl bromoacetate (1.6 ml, 0.02 mole) was added. After stirring at ambient temperature overnight, the solid aminoacetaldehyde dimethyl acetal hydrobromide was filtered and the solution was concentrated to an oil. Flash chromatography on silica (LPS-1) (40:60 ethyl acetate:hexane eluant) gave 2.2 gms of the purified title compound.

(B)

(3S)-[[[3-[[(Phenylmethoxy)carbonyl]amino]-2-oxo-1-azetidinyl]carbonyl](2,2-dimethyoxyethyl)amino]acetic acid, phenylmethyl ester To a slurry of (S)-3-[[(phenylmethoxy)carbonyl]amino]-2-azetidinone (0.88 g, 4 mmole) in 10 ml of dichloromethane at −10° C. under argon was added 12.5% phosgene/toluene (5.8 ml, 6.8 mmole) followed by triethylamine (0.465 g, 4.6 mmole). The reaction mixture was stirred at −10° C. for 2 hours. The reaction mixture was concentrated with no external heating and then redissolved in dichloromethane and cooled to −10° C. (2,2-Dimethoxyethyl)(2-phenylmethoxy-2-oxoethyl)amine (1.06 g, 4.2 mmole) was added followed by the addition of triethylamine. The reaction mixture was stirred at −10° C. for 45 minutes.

The reaction was worked up by pouring into 10% monobasic potassium phosphate and extracting with dichloromethane. After washing with brine and drying over anhydrous sodium sulfate, the solvent was evaporated leaving an oil. The crude material was flash chromatographed on silica (LPS-1) eluting with 3:7 ethyl acetate:hexane. The fractions containing pure material were combined and concentrated to give 0.454 gm of material which crystallized on cooling.

(C)

[3S(Z)]-[[[3-[[(2-Amino-4-thiazolyl)(methoxyimino)acetyl]amino]-2-oxo-1-azetidinyl]carbonyl](2,2-dimethoxyethyl)amino]acetic acid, potassium salt To a solution of (3S)-[[[3-[[(phenylmethoxy)carbonyl]amino]-2-oxo-1-azetidinyl]carbonyl](2,2-dimethoxyethyl)amino]acetic acid, phenylmethyl ester (0.20 gm, 0.4 mmole) in 3 ml of dimethylformamide was added to 100 mg of 10% palladium on charcoal and 76 mg (0.4 mmole) of p-toluenesulfonic acid. The protecting groups were removed by atmospheric hydrogenation at 0° C. for 3.5 hours.

To a solution of (Z)-2-amino-α-(methoxyimino)-4-thiazoleacetic acid (90.64 mg, 0.44 mmole) and N-hydroxybenzotriazole (59.5 mg, 0.44 mmole) in dimethylformamide (3 ml) under argon at 0° C. was added N,N-dicyclohexylcarbodiimide (90.7 mg, 0.44 mmole). The reaction mixture was stirred at room temperature for 1.5 hours. The side chain ester was filtered away from the solid dicyclohexylurea formed.

After the hydrogenation was completed, diisopropylethylamine (51.6 mg, 0.4 mmole) was added at 0° C. followed by the addition of the solution of side chain ester. The reaction mixture was stirred at 5° C. overnight.

The reaction mixture was concentrated as rapidly as possible using a vacuum pump (throughout the subsequent isolation and purification, the solutions were kept at 0°-5° C. at all times). The residue was dissolved in cold doubly distilled water and filtered through Celite. The pH of the filtrate was adjusted to 6.5 with 1N potassium bicarbonate. This solution was sent through a column of Dowex AG-50 K+ form and then purified on an HP-20 column eluting with water. After lyophilization, 146 mg (57.7%) of the title compound was obtained, melting point 163°-175° C., dec. 400 MHz NMR and microanalysis established the presence of 0.5 moles of potassium tolylsulfonate.

Anal. Calc'd. for $C_{16}H_{21}N_6O_8SK$: C, 36.01; H, 4.35; N, 12.92; S, 7.39; K, 9.02. Found: C, 35.60; H, 4.07; N, 12.92; S, 7.02; K, 9.29.

EXAMPLE 36

[3S(Z)]-[[[3-[[(2-Amino-4-thiazolyl)(methoxyimino)acetyl]amino]-2-oxo-1-azetidinyl]carbonyl][2-(dimethylamino)-2-oxoethyl]amino]acetic acid, potassium salt (A)
(3S)-[[[3-[[(t-Butyloxy)carbonyl]amino]-2-oxo-1-azetidinyl]carbonyl](2,2-dimethoxyethyl)amino]acetic acid (S)-2,2'-[[[3-[[(t-Butyloxy)carbonyl]amino]-2-oxo-1-azetidinyl]carbonyl]imino]bisacetic acid, dibenzyl ester (1.05 g, 2 mmol; see example 18A) was dissolved in 12 ml of dry tetrahydrofuran. Hydrogenolysis of the benzyl protecting groups at room temperature over 525 mg of 10% palladium on charcoal was complete after 1 hour. The reaction mixture was filtered to remove the palladium on charcoal catalyst, toluene (~4 ml) was added, and the volatiles were evaporated to yield the diacid of the azetidinone starting material.

The diacid was dissolved in 30 ml of dry tetrahydrofuran and a solution of dicyclohexylcarbodiimide (454 mg, 2.2 mmol) in 8 ml of dry tetrahydrofuran was added dropwise to the stirred reaction mixture at room temperature. The reaction mixture was stirred for 1.5 hours at room temperature. The reaction mixture was cooled to −78° C. and a solution of 1N dimethylamine in tetrahydrofuran (4 ml) at 0° C. was added dropwise. The reaction mixture was warmed to 0° C. and was stirred for 45 minutes. The mixture was then cooled to −78° C., and 4 ml of 0.5N hydrochloric acid was added. As the reaction mixture was warmed to 0° C., 4 ml of water was added, and the pH was adjusted to 2.5 with 0.5N hydrochloric acid. The tetrahydrofuran was evaporated, and the crude product was purified by column chromatography on HP-20 (eluting with water, 5% acetone-water, 10% acetone-water, and 20% acetone-water) to yield upon lyophilization 509 mg of the title compound.

(B)
[3S(Z)]-[[[3-[[(2-Amino-4-thiazolyl)(methoxyimino)acetyl]amino]-2-oxo-1-azetidinyl]carbonyl][2-(dimethylamino)-2-oxoethyl]amino]acetic acid, potassium salt Diisopropylethylamine (0.323 ml, 1.86 mmol) was added to 258 mg (1.2 mmol) of (Z)-2-amino-α-(methoxyimino)-4-thiazoleacetic acid (containing 0.38 molar equivalents of hydrochloric acid in 4 ml of dimethylformamide at 23° C. The mixture was cooled to −20° C., diphenyl chlorophosphate (0.249 ml, 1.2 mmol) was added, and the resulting mixture was stirred for 30 minutes to yield a mixed anhydride.

(3S)-[[[3-[[(t-Butyloxy)carbonyl]amino]-2-oxo-1-azetidinyl]carbonyl](2,2-dimethoxyethyl)amino]acetic acid (372 mg, 1 mmol) was cooled to 0° C. and a solution containing 5 ml of trifluoroacetic acid, 5 ml of dichloromethane, and 1 ml of anisole at 0° C. was added. After stirring at 0° C. for 2 hours, toluene (~3 ml) was added, and the volatiles were evaporated. The residue was triturated with hexane and anhydrous ether to yield a white solid. The residue was then dissolved in 4 ml of dimethylformamide and upon cooling to 0° C., 0.587 ml (3.32 mmol) of diisopropylethylamine was added. The reaction mixture containing the mixed anhydride was then immediately added, and the resulting mixture was stirred at 0° C. for 2 hours.

The volatiles were removed under vacuum, and the residue was subjected to column chromatography with water on Dowex 50X2-400 resin (K+ form). After lyophilization, the pH of the crude product (in ~4 ml $H_2O$) was adjusted to 2.5 with 1N hydrochloric acid, and this was then subjected to chromatography on HP-20 (eluting with water, 5% acetone-water, 10% acetone-water, and 20% acetone-water) to give the impure acid of the title compound. After lyophilization, the crude product was dissolved in ~4 ml of water at 0° C. and the pH was adjusted to 6.5 with aqueous potassium bicarbonate. Purification of this solution by column chromatography on HP-20 (eluting with water yielded, upon lyophilization, 240 mg of the title compound, melting point 162°-171° C., dec.

Anal. Calc'd. for $C_{16}H_{20}N_7O_7SK.2H_2O$: C, 36.27; H, 4.57; N, 18.51. Found: C, 36.41; H, 4.75; N, 18.37.

EXAMPLE 37

[3S(Z)]-[[[3-[[(2-Amino-4-thiazolyl)(methoxyimino)acetyl]amino]-2-oxo-1-azetidinyl]carbonyl](1-methylethyl)amino]acetic acid (A) Isopropyl[2-(phenylmethoxy)-2-oxoethyl]amine N-isopropyl ethyl glycinate (22.9 g, 0.158 mole) and 33.1 g of p-toluenesulfonic acid monohydrate (0.174 mole) were placed in a reaction vessel filtered with a reflux condenser and a Dean-Stark apparatus. Benzyl alcohol (158 ml, 1.53 mole) and 158 ml of benzene (1.77 mole) were added, and the reaction mixture was refluxed for 24 hours. The reaction mixture was cooled to room temperature, and ~800 ml of ether was added. After stirring at −30° C. overnight, the reaction mixture was filtered and the precipitate collected. The precipitate was washed with cold ether to yield 60.97 g of the impure p-toluenesulfonate salt of the title compound.

The p-toluenesulfonate salt was suspended in ~400 ml of ice-cold water and 26.22 g of potassium carbonate was added (pH 8-9). The aqueous mixture was extracted 3 times with ether and the combined organic layers were dried over sodium sulfate and filtered. The volume of the ether solution was reduced to ~400 ml and was cooled to 0° C. Water (~400 ml) was added, and the pH was adjusted to 1.5 with 1N hydrochloric acid while rapidly stirring. The ether was evaporated, and the remaining aqueous solution was lyophilized to yield 28.63 g of the title compound.

(B)
(3S)-[[[3-[[(Phenylmethoxy)carbonyl]amino]-2-oxo-1-azetidinyl]carbonyl](1-methylethyl)amino]acetic acid, phenylmethyl ester (S)-3-[[(Phenylmethoxy)carbonyl]amino]-2-azetidinone (660 mg, 3.0 mmol) was suspended in 7.5 ml of dichloromethane and cooled to −10° C. A solution of 12.5% phosgene in toluene (4.4 ml, 5.1 mmol) was added, and then triethylamine (0.481 ml, 3.45 mmol) was added dropwise to the rapidly stirring mixture. After stirring at −10° C. for 2 hours, the volatiles were evaporated without external heating. The residue was cooled to −10° C., and dissolved in 7.5 ml of dichloromethane.

Potassium carbonate (911 mg, 6.6 mmol) was added to a rapidly stirring solution of N-isopropylglycine benzyl ester hydrochloride (804 mg, 3.3 mmol) in 7.5 ml of water and 5 ml of dichloromethane at 0° C. (pH 8). The mixture was extracted 3 times with dichloromethane, and the combined organic layers were dried over sodium sulfate and filtered. The volume of solvent was reduced to ~3 ml by evacuation and dried with 4A molecular sieves to yield the free amine of the benzyl ester.

Triethylamine (0.460 ml, 3.3 mmol) was added to the solution containing the free amine, and the resulting mixture was immediately added to the solution containing the azetidinone reagent at −10° C. After stirring at −10° C. for 3 hours, the reaction mixture was poured into aqueous monobasic potassium phosphate and extracted 3 times with dichloromethane. The combined organic layers were dried over sodium sulfate and filtered. The volatiles were removed, and the residue was subjected to chromatography on silica (LPS-1) (eluting with 35% ethyl acetate-hexane) yielding 342 mg of the title compound.

(C)
[3S(Z)]-[[[3-[[(2-Amino-4-thiazolyl)(methoxyimino)acetyl]amino]-2-oxo-1-azetidinyl]carbonyl](1-methylethyl)amino]acetic acid Diisopropylethylamine (0.240 ml, 1.38 mmol) was added to 191 mg (0.89 mmole) of (Z)-2-amino-α-(methoxyimino)-4-thiazoleacetic acid (containing 0.38 molar equivalents of hydrochloric acid) in 4 ml of dimethylformamide at 23° C. The mixture was cooled to −20° C., diphenylchlorophosphate (0.184 ml, 0.89 mmol) was added, and the resulting mixture was stirred for 30 minutes to yield a mixed anhydride.

(3S)-[[[3-[[(Phenylmethoxy)carbonyl]amino]-2-oxo-1-azetidinyl]carbonyl](1-methylethyl)amino]acetic acid, phenylmethyl ester (335 mg, 0.74 mmol) was dissolved in 3 ml of dimethylformamide and 141 mg (0.74 mmol) of p-toluenesulfonic acid monohydrate was added. Hydrogenolysis of the protecting groups at room temperature over 167 mg of 10% palladium on charcoal was complete after 75 minutes. The reaction mixture was placed under nitrogen and cooled to 0° C. Diisopropylethylamine (0.425 ml, 2.44 mmol) was then added to the azetidinone, immediately followed by the mixed anhydride, and the resulting mixture was stirred at 0° C. for 2 hours.

The reaction mixture was filtered to remove the palladium on charcoal and the volatiles were removed under vacuum. The residue was subjected to column chromatography with water on Dowex 50X2-400 resin (K+ form) followed by chromatography on HP-20 (eluting with water, and 5% acetone-water) to give the impure potassium salt of the title compound. The crude product was dissolved in ~5 ml of water at 0° C. and the pH was adjusted to 2.5 with 1N hydrochloric acid. Purification of this solution by column chromatography on HP-20 (eluting with water, 5% acetone-water, 10% acetone-water, 20% acetone-water, an 25% acetone-water) yielded upon lyophilization 185 mg of the title compound, melting point 150° C., dec.

Anal. Calc'd. for $C_{15}H_{20}N_6O_6S$: C, 43.69; H, 4.85; N, 20.39. Found: C, 44.75; H, 5.15; N, 15.82.

EXAMPLE 38
[3S(Z)]-[[2-(Acetylamino)ethyl][[3-[[(2-amino-4-thiazolyl)(methoxyimino)acetyl]amino]-2-oxo-1-azetidinyl]carbonyl]amino]acetic acid, potassium salt

(A)
N-Acetyl-N'-[2-(phenylmethoxy)-2-oxoethyl]ethylenediamine

Benzyl glyoxylate (3.28 g, 20.0 mmol) in dry tetrahydrofuran (15 ml) was added dropwise in monoacetylethylenediamine (1.53 g, 15 mmol) in dry tetrahydrofuran (60 ml) at room temperature. After 2 hours, the tetrahydrofuran was removed under vacuum, and the residue was dissolved in dry methanol (100 ml). Upon cooling to 0° C., 1.55 g of sodium cyanoborohydride was added, immediately followed by dropwise addition of 1.54 ml of acetic acid. The reaction was allowed to warm to room temperature and stirred for 40 minutes. The volatiles were removed under vacuum, and the residue was extracted from aqueous sodium bicarbonate with ethyl acetate. The combined organic layers were dried with sodium sulfate, and the volatiles were removed. The residue was purified by column chromatography on silica (LPS-1) (loading with 2% methanol/dichloromethane and eluting with 5% methanol/dichloromethane to yield 1.46 g of the title compound.

(B)
(3S)-[[2-(Acetylamino)ethyl][[3-[[(phenylmethoxy)carbonyl]amino]-2-oxo-1-azetidinyl]carbonyl]amino]acetic acid, phenylmethyl ester (S)-3-[[(Phenylmethoxy)carbonyl]amino]-2-azetidinone (440 mg, 2.0 mmol) was suspended in 5 ml of dry dichloromethane and cooled to −10° C. A solution of 12.5% phosgene in toluene (2.9 ml, 3.4 mmol) was added and then triethylamine (0.307 ml, 2.2 mmol) was added dropwise to the rapidly stirring mixture. After stirring at −10° C. for 1.5 hours, the volatiles were evaporated without external heating. The residue was cooled to −10° C. and dissolved in 5 ml of dichloromethane.

Triethylamine (0.307 ml, 2.2 mmol) was added to a solution of N-acetyl-N'-[2-(phenylmethoxy)-2-oxoethyl]ethylenediamine (500 mg, 2.0 mmol) in dichloromethane (2.0 ml), and the resulting mixture was immediately added to the above-prepared solution at −10° C. After stirring at −10° C. for 15 minutes and 0° C. for 3 hours, the reaction mixture was poured into aqueous monobasic potassium phosphate and extracted three times with ethyl acetate. The combined organic layers were dried over sodium sulfate and filtered. The volatiles were removed, and the residue was subjected to chromatography on silica (LPS-1) (eluting with 10% acetonitrile/ethyl acetate) yielding 325 mg of the title compound.

(C)

[3S(Z)]-[[2-(Acetylamino)ethyl][[3-[[(2-amino-4-thiazolyl)(methoxyimino)acetyl]amino]-2-oxo-1-azetidinyl]carbonyl]amino]acetic acid, potassium salt Diisopropylethylamine (0.204 ml, 1.17 mmol) was added to 165 mg (0.77 mmol) of (Z)-2-amino-α-(methoxyimino)-4-thiazoleacetic acid (containing 38 mole % hydrochloric acid) in 2.5 ml of dimethylformamide at 23° C. The mixture was cooled to −10° C. and diphenylchlorophosphate (0.160 ml, 0.77 mmol) was added, and the resulting mixture was stirred for 30 minutes to yield a mixed anhydride.

(3S)-[[2-(Acetylamino)ethyl][[3-[[(phenylmethoxy)carbonyl]amino]-2-oxo-1-azetidinyl]carbonyl]amino]acetic acid, phenylmethyl ester (319 mg, 0.64 mmol) was dissolved in 2.5 ml of dimethylformamide and 121 mg (0.64 mmol) of p-toluenesulfonic acid monohydrate was added. Hydrogenolysis of the protecting groups at room temperature over 160 mg of 10% palladium on charcoal was complete after 1 hour. The reaction mixture was placed under an inert atmosphere and cooled to 0° C. Diisopropylethylamine (0.369 ml, 2.11 mmol) was then added to the azetidinone, immediately followed by the mixed anhydride, and the resulting mixture was stirred at 0° C. for 2 hours.

The reaction mixture was filtered to remove the palladium on charcoal and the volatiles were removed under vacuum. The residue was purified by column chromatography with water on Dowex 50X2-400 resin (K+ form). Upon lyophilization, the pH of the residue (in ∼4 ml of water at 0° C.) was adjusted to 2.5 with 1N hydrochloric acid, and this was then subjected to chromatography on HP-20 (eluting with water, 5% acetone-water, 10% acetone-water, and 15% acetone-water) to give the impure acid of the title compound. After lyophilization, the crude product was dissolved in ∼4 ml of water at 0° C., and the pH was adjusted to 7.5 with aqueous potassium bicarbonate. Purification of this solution by column chromatography on HP-20 (eluting with water) yielded, upon lyophilization, 114 mg of the title compound, melting point 170°–180° C., dec.

Anal. Calc'd. for $C_{16}H_{20}N_7O_7SK \cdot 3.0H_2O$: C, 35.09; H, 4.79; N, 17.91. Found: C, 35.15; H, 4.52; N, 17.48.

EXAMPLE 39

[3S(Z)]-N-[[2-[[(2-Amino-4-thiazolyl)(methoxyimino)acetyl]amino]-2-oxo-1-azetidinyl]carbonyl]-N-(3-hydroxyphenyl)glycine (A) Benzyl N-(3-benzyloxy)phenylglycinate To a solution of benzyl bromoacetate (4.0 ml, 25 mmole) and 3-benzyloxyaniline (4.98 g, 25 mmole) in 25 ml of dry dimethylformamide was added sodium acetate (2.05 g, 25 mmole). The reaction mixture was stirred at room temperature overnight and extracted from water with three portions of ethyl acetate. The combined organic layers were washed with water and dried over sodium sulfate. The volatiles were removed, and the residue was purified by flash chromatography on silica (LPS-1) (eluting with 10% ethyl acetate/hexane) to yield 6.0 g of moderately pure benzyl N-(3-benzyloxy)phenylglycinate.

(B)
(3S)-N-[[3-[[(Phenylmethoxy)carbonyl]amino]-2-oxo-1-azetidinyl]carbonyl]-N-[3-(phenylmethoxy)phenyl]glycine, phenylmethyl ester Benzyl N-(3-benzyloxy)phenylglycinate (780 mg) was dissolved in 6 ml of dry toluene and cooled to −15° C. A phosgene solution (2.9 ml of 12.5% in toluene, 3.4 mmole) was added to the reaction mixture followed by the dropwise addition of pyridine (0.348 ml, 4.3 mmol) with rapid stirring. The reaction mixture was stirred for 1.5 hours at −15° C. and then allowed to warm to room temperature.

The precipitate of pyridinium hydrochloride was filtered under argon, and the volatiles were removed from the filtrate. This was dissolved in 4 ml of dry tetrahydrofuran and cooled to 0° C. To this solution was added (S)-3-[[(phenylmethoxy)carbonyl]amino]-2-azetidinone (440 mg, 2.0 mmol) and dimethylaminopyridine (36 mg, 0.3 mmol). Triethylamine (0.307 ml, 2.2 mmol) was added dropwise and the reaction was allowed to warm to room temperature and stir overnight. The product was extracted from dilute aqueous hydrochloric acid with three portions of ethyl acetate. The combined organic extracts were dried with sodium sulfate, filtered, and the volatiles removed. The residue was purified by flash chromatography on silica (LPS-1) (eluting with 50% ethyl acetate/hexane) to yield 559 mg of impure title compound.

(C)
[3S(Z)]-N-[[2-[[(2-Amino-4-thiazolyl)(methoxyimino)acetyl]amino]-2-oxo-1-azetidinyl]carbonyl]-N-(3-hydroxyphenyl)glycine Diisopropylethylamine (0.305 ml, 1.75 mmol) was added to 243 mg (1.13 mmol) of (Z)-2-amino-α-(methoxyimino)-4-thiazoleacetic acid (containing 0.38 molar equivalents of hydrochloric acid in 4 ml of dimethylformamide at 23° C. The mixture was cooled to −15° C., diphenylchlorophosphate (0.234 ml, 1.13 mmol) was added, and the resulting mixture was stirred for 30 minutes to yield a mixed anhydride.

(3S)-N-[[3-[[(Phenylmethoxy)carbonyl]amino]-2-oxo-1-azetidinyl]carbonyl]-N-[3-(phenylmethoxy)phenyl]glycine, phenylmethyl ester (555 mg, ∼0.94 mmol) was dissolved in 4 ml of dimethylformamide and 179 mg (0.94 mmol) of p-toluenesulfonic acid monohydrate was added. Hydrogenolysis of the protecting groups at room temperature over 278 mg of 10% palladium on charcoal was complete after 50 minutes. The reaction mixture was placed under nitrogen and cooled to 0° C.

Diisopropylethylamine (0.540 ml, 3.10 mmol) was then added to the azetidinone, immediately followed by the mixed anhydride, and the resulting mixture was stirred at 0° C. for 3 hours.

The reaction mixture was filtered to remove the palladium on charcoal and the volatiles were removed under vacuum. The residue was suspended in 3 ml of water at 0° C., the pH was adjusted to 6.5 with aqueous potassium bicarbonate, and the resulting mixture was subjected to column chromatography with water on Dowex 50X2-400 resin (K+ form). The crude product was dissolved in ∼5 ml of water at 0° C. and the pH was adjusted to 3.0 with 1N hydrochloric acid. Purification of this suspension by column chromatography on HP-20 (eluting with water, 5% acetone/water, 10% acetone/water, 15% acetone/water, and 20% acetone/- water) yielded, upon lyophilization, 183 mg of the title compound, melting point 163°–171° C., dec.

Anal. Calc'd. for $C_{18}H_{18}N_6O_7S$: C, 46.75; H, 3.90; N, 18.18. Found: C, 47.46; H, 4.07; N, 15.12.

EXAMPLE 40

[3S(Z)]-N-[[3-[[(2-Amino-4-thiazolyl)(methoxyimino)acetyl]amino]-2-oxo-1-azetidinyl]carbonyl]-N-(4-hydroxyphenyl)glycine, potassium salt (A)

N-[2-(Phenylmethoxy)-2-oxoethyl]-4-benzyloxyaniline

4-Benzyloxyaniline hydrochloride (5.893 g, 25 mmol) was added to a solution of benzyl bromoacetate (4.0 ml, 25 mmol) in 25 ml of dry dimethylformamide. Sodium acetate (2.051 g, 25 mmole) and 13.82 g (0.1 mole) of potassium carbonate were added, and the reaction mixture was stirred at room temperature overnight. The reaction mixture was extracted from water with three portions of ethyl acetate. The combined organic layers were washed with water and dried over sodium sulfate. The volatiles were removed, and the residue was purified by flash column chromatography on silica (LPS-1) (eluting with 15% ethyl acetate/hexane) to yield 5.64 g of the title compound.

(B)

(3S)-N-[[3-[[(Phenylmethoxy)carbonyl]amino]-2-oxo-1-azetidinyl]carbonyl]-N-[4-(phenylmethoxy)phenyl]glycine, phenylmethyl ester Benzyl-N-(4-benzyloxyphenyl)glycinate (694 mg, 2.0 mmole) was dissolved in 6 ml of dry toluene and cooled to 0° C. A phosgene solution (2.9 ml, 12.5% in toluene) was added to the reaction mixture followed by the dropwise solution of pyridine (0.348 ml, 4.3 mmol) with rapid stirring. The reaction was stirred for 1.5 hours at 0° C. and then allowed to warm to room temperature. The precipitate of pyridinium hydrochloride was filtered under argon, and the volatiles were removed from the filtrate. This was dissolved in 4 ml of dry tetrahydrofuran and cooled to 0° C. To this solution was added (S)-3-[[(phenylmethoxy)carbonyl]amino]-2-azetidinone (440 mg, 2.0 mmole) and 36 mg (0.3 mmole) of dimethylaminopyridine. Triethylamine (0.307 ml, 2.2 mmole) was then added dropwise, and the reaction mixture was allowed to warm to room temperature and stir overnight. The product was extracted with ethyl acetate from dilute aqueous hydrochloric acid. The combined organic extracts were dried with sodium sulfate and the volatiles removed. The residue was purified by flash chromatography on silica (LPS-1) (eluting with 1:1 ethyl acetate/hexane) to yield 465 mg of the title compound.

(C)

[3S(Z)]-N-[[3-[[(2-Amino-4-thiazolyl)(methoxyimino)acetyl]amino]-2-oxo-1-azetidinyl]carbonyl]-N-(4-hydroxyphenyl)glycine, potassium salt N-Hydroxybenzotriazole hydrate (125 mg, 0.924 mmol) and 191 mg (0.924 mmol) of (Z)-2-amino-α-(methoxyimino)-4-thiazoleacetic acid (containing 0.15 molar equivalents of methanol were dissolved in 3.3 ml of dimethylformamide and cooled to 0° C. N,N'-Dicyclohexylcarbodiimide (191 mg, 0.924 mmol) was added, and the mixture was warmed to room temperature. The reaction mixture was stirred for 30 minutes to yield the N-hydroxybenzotriazole ester.

(3S)-N-[[3-[[(Phenylmethoxy)carbonyl]amino]-2-oxo-1-azetidinyl]carbonyl]-N-[4-(phenylmethoxy)phenyl]glycine, phenylmethyl ester (457 mg, 0.77 mmol) was dissolved in 3.3 ml of dimethylformamide and 147 mg (0.77 mmol) of p-toluenesulfonic acid monohydrate was added. Hydrogenolysis of the groups at room temperature over 229 mg of 10% palladium on charcoal was complete after 45 minutes. The reaction mixture was placed under nitrogen and cooled to 0° C. Diisopropylethylamine (0.442 ml, 2.54 mmol) was then added to the azetidinone immediately followed by the N-hydroxybenzotriazole ester, and the resulting mixture was stirred at 5° C. overnight.

The reaction mixture was filtered to remove the palladium on charcoal and the dicyclohexylurea precipitate, and the volatiles were removed under vacuum. The residue was dissolved in ~3 ml of water at 0° C., and the pH was adjusted to 6.5 with aqueous potassium bicarbonate. This solution was subjected to column chromatography with water on Dowex 50X2-400 resin (K+ form) to yield impure title compound. The crude product was dissolved in ~3 ml of water at 0° C. and the pH was readjusted to 6.5 with 1N hydrochloric acid. Purification of this solution by column chromatography on HP-20 (eluting with water, and 5% acetone/water) yielded, upon lyophilization, 108 mg of the title compound, melting point 162°–168° C., dec.

Anal. Calc'd. for $C_{18}H_{17}N_6O_7SK.2.44H_2O$: C, 39.75; H, 4.05; N, 15.45. Found: C, 39.75; H, 4.05; N, 15.59.

EXAMPLE 41

(R)-4-[(Aminocarbonyl)oxy]-1-[[(S)-3-[[(2-amino-4-thiazolyl)(methoxyimino)acetyl]amino]-2-oxo-1-azetidinyl]carbonyl]-L-proline (A)

(trans)-1-[[3S-[[(Phenylmethoxy)carbonyl]amino]-2-oxo-1-azetidinyl]carbonyl]-4-[(aminocarbonyl)oxy]-L-proline, phenylmethyl ester (trans)-1-[[3S-[[(Phenylmethoxy)carbonyl]amino]-2-oxo-1-azetidinyl]carbonyl]-4-hydroxy-L-proline, phenylmethyl ester (1.32 g, 2.83 mmole; see example 25A) in 25 ml of dry dichloromethane at −5° C. was added dropwise chlorosulfonylisocyanate (0.4 g, 2.83 mmole). The reaction mixture was stirred at −5° C. for 20 minutes at which point it became turbid white. Sodium sulfite (0.36 g, 2.86 mmole) in 2 ml water was added and the reaction was stirred and allowed to warm to 15° C. over a period of 1 hour. Ethyl acetate and water were added and the layers were separated. The organic layer was washed with water and brine and dried over anhydrous sodium sulfate. After concentrating to a residue, the crude product was purified on a silica (LPS-1) column eluting with ethyl acetate:hexane (1:1) to give 1 gm of pure compound.

(B)

(R)-4-[(Aminocarbonyl)oxy]-1-[[(S)-3-[[(2-amino-4-thiazolyl)(methoxyimino)acetyl]amino]-2-oxo-1-azetidinyl]carbonyl]-L-proline A mixture of (trans)-1-[[3S-[[(phenylmethoxy)carbonyl]amino]-2-oxo-1-azetidinyl]carbonyl]-4-[(aminocarbonyl)oxy]-L-proline, phenylmethyl ester (0.5 gms, 0.98 mmole), p-toluenesulfonic acid monohydrate (0.19 gms, 1 mmole) and 10% palladium on charcoal (0.25 gms) in 5 ml dimethylformamide was stirred at room temperature under a stream of hydrogen for 3 hours at which time tlc confirmed that the deprotection was completed. To (Z)-2-amino-α-(methoxyimino)-4- thiazoleacetic acid (0.206 gms, 1 mmole) and N-hydroxybenzotriazole (0.135 gms, 1 mmole) in 3 ml of dimethylformamide at 0° C. was added dicyclohexylcarbodiimide (0.206 gms, 1 mmole). This was stirred at ambient temperature for 1 hour. The deprotected β-lactam was cooled to 0° C. and diisopropylethylamine (0.129 gms, 1 mmole) was added, followed by the N-hydroxybenzotriazole ester. The reaction mixture was stirred at 5° C. overnight and the dimethylformamide was removed at room temperature. The reaction mixture was diluted with water, filtered through Celite and adjusted to pH 6.8 with 1N potassium bicarbonate. This aqueous solution was applied to an AG-50 (K+) column and eluted with water until all of the fluorescent material was collected. The aqueous solution was concentrated to a small volume and chromatographed twice on an HP-20 column eluting with water to achieve complete separation from N-hydroxybenzotriazole. However, the potassium salt of the title compound was contaminated with a large amount of the potassium salt of p-toluenesulfonic acid. The sample was then taken up in water and adjusted to pH 2.55 with 1% hydrochloric acid. This solution was then applied to an HP-20 column and eluted first with water until all the p-toluenesulfonic acid was removed and then eluted with an acetone/water gradient to recover the product. The fractions containing pure product were lyophilized to a white solid (61 mg), melting point >190° C., dec.

EXAMPLE 42

[3S(Z)]-[[[3-[[(2-Amino-4-thiazolyl)[[1,1-dimethyl-2-oxo-2-(1-piperazinyl)ethoxy]imino]acetyl]amino]-2-oxo-1-azetidinyl]carbonyl]methylamino]acetic acid (A) N-Tritylpiperazine To a solution of piperazine (25.9 g, 0.30 mol) in tetrahydrofuran (300 ml) at 0° C. was added triphenylmethyl chloride (27.9 g, 0.10 mol). The reaction was stirred for 48 hours at room temperature. The product was extracted from aqueous sodium carbonate with three portions of ether. The combined organic layers were washed with three portions of water, dried with sodium sulfate, and the volatiles were then evaporated. The residue was subjected to chromatography on silica (LPS-1) (eluting with 90:10:4 ether/acetonitrile/triethylamine) to yield 7.62 g of N-tritylpiperazine.

(B)
(Z)-2-Amino-α-[[1,1-dimethyl-2-oxo-2-(N-tritylpiperazinyl)ethoxy]imino]-4-thiazoleacetic acid, methyl ester To a solution of (Z)-2-amino-α-[(1-carboxy-1-methylethoxy)imino]-4-thiazoleacetic acid, methyl ester (3.16 g, 11.0 mmol) in dimethylformamide (44 ml) and N,N-diisopropylethylamine (2.11 ml, 12.1 mmol) at −10° C. was added diphenylchlorophosphate (2.51 ml, 12.1 mmol). After one hour at −10° C., a solution of N-tritylpiperazine (3.87 g, 11.0 mmol correcting for 7% by weight triethylamine) in tetrahydrofuran (20 ml) and triethylamine (1.54 ml, 11.0 mmol) was added over 15 minutes. The reaction was stirred for an additional 15 minutes at −10° C. and for 2 hours at 0° C.

The product was extracted from aqueous sodium bicarbonate with three portions of ethyl acetate, and the combined organic layers were washed with two portions of water. After drying with sodium sulfate, the volatiles were removed. The residue was subjected to column chromatography on Mallinckrodt CC-7 silica (eluting with 1:1 ethyl acetate/hexane) to yield 4.02 g of the title compound.

(C)
(Z)-2-Amino-α-[[1,1-dimethyl-2-oxo-2-(N-tritylpiperazinyl)ethoxy]imino]-4-thiazoleacetic acid (Z)-2-Amino-α-[[1,1-dimethyl-2-oxo-2-(N-tritylpiperazinyl)ethoxy]imino]-4-thiazoleacetic acid, methyl ester (4.03 g, 6.75 mmol) was suspended in a solution of 0.90 g of potassium hydroxide in ethanol (22.5 ml) and water (1.8 ml), and stirred overnight at room temperature. The reaction was then heated to 60° C. for 30 minutes. Upon cooling to room temperature, water (22.5 ml) was added, and the reaction mixture was filtered through Celite. The filtrate was then acidified to pH 3 with 1N hydrochloride acid while cooling in ice, and the precipitate that formed was isolated by filtration. The precipitate was washed with water, ether and acetonitrile to yield 1.71 g of the title compound.

(D)
[3S(Z)]-[[[3-[[(2-Amino-4-thiazolyl)[[1,1-dimethyl-2-oxo-2-(N-trityl-1-piperazinyl)ethoxy]imino]acetyl]amino]-2-oxo-1-azetidinyl]carbonyl]methylamino]acetic acid, potassium salt Diisopropylethylamine (0.148 ml, 0,85 mmol) was added to 455 mg (0.78 mmmol) of (Z)-2-amino-α-[[1,1-dimethyl-2-oxo-2-(N-tritylpiperazinyl)ethoxy]imino]-4-thiazoleacetic acid in 3 ml of dimethylformamide at 23° C. The mixture was cooled to −15° C., diphenylchlorophosphate (0.162 ml, 0.78 mmol) was added, and the resulting mixture was stirred for 30 minutes to yield a mixed anhydride.

(S)-[N-[[3-[[(Phenylmethoxy)carbonyl]amino]-2-oxo-1-azetidinyl]carbonyl]methylamino]acetic acid, phenylmethyl ester (333 mg, 0.78 mmol, see example 8A) was dissolved in 5 ml of dimethylformamide and 148 mg (0.78 mmol) of p-toluenesulfonic acid monohydrate was added. Hydrogenolysis of the protecting groups at room temperature over 166 mg of 10% palladium on charcoal was complete after 1 hour. The reaction mixture was placed in an inert atmosphere and cooled to 0° C. Diisopropylethylamine (0.448 ml, 2.57 mmol) was then added to the azetidinone, immediately followed by the mixed anhydride, and the resulting mixture was stirred at 5° C. overnight.

The reaction mixture was filtered to remove the palladium on charcoal, and the volatiles were removed under vacuum. The residue was subjected to column chromatography with 20% acetone-water on Dowex 50X2-400 resin (K+ form). Upon lyophilization, the crude product was dissolved in water and purified by column chromatography on HP-20 (eluting with water, 10% acetone-water, 20% acetone-water, and 40% acetone-water) to yield upon lyophilization 266 mg of the title compound.

(E)
[3S(Z)]-[[[3-[[(2-Amino-4-thiazolyl)[[1,1-dimethyl-2-oxo-2-(1-piperazinyl)ethoxy]imino]acetyl]amino]-2-oxo-1-azetidinyl]carbonyl]methylamino]acetic acid

[3S(Z)]-[[[3-[[(2-Amino-4-thiazolyl)[[1,1-dimethyl-2-oxo-2-(N-trityl-1-piperazinyl)ethoxy]imino]acetyl]amino]-2-oxo-1-azetidinyl]carbonyl]methylamino]acetic acid, potassium salt (60 mg, 0.075 mmol) was dissolved in 1 ml of 98% formic acid at room temperature. After 2 hours, the volatiles were removed under vacuum (without external heating). The residue was purified by column chromatography on HP-20 (eluting with water, 5% acetone-water, and 10% acetone-water) to yield, upon lyophilization, 18 mg of the title compound, melting point 220°-225° C., dec.

Anal. Calc'd. for $C_{20}H_{28}N_8O_7S.2.27H_2O$: C, 44.02; H, 5.60; N, 20.54. Found: C, 44.02; H, 5.57; N, 19.82.

EXAMPLE 43

[3S(Z)]-N-[[3-[[(2-Amino-4-thiazolyl)(methoxyimino)acetyl]amino]-2-oxo-1-azetidinyl]carbonyl]-N-(3,4-dihydroxyphenyl)glycine, potassium salt (A) Benzyl N-(3,4-dibenzyloxy)phenylglycinate To a solution of benzyl bromoacetate (2.39 ml, 15 mmole) and 3,4-dibenzyloxyaniline (4.575 g, 15 mmole) in 15 ml of dry dimethylformamide was added sodium acetate (1.231 g, 15 mmole). The reaction was stirred at room temperature overnight and extracted from water with three portions of ethyl acetate. The combined organic layers were washed with water, dried over sodium sulfate and filtered. The volatiles were removed, and the residue was purified by flash chromatography on silica (LPS-1) (eluting with 15% ethyl acetate/hexane) to yield 3.86 g of the title compound.

(B)
(3S)-N-[[3-[[(Phenylmethoxy)carbonyl]amino]-2-oxo-1-azetidinyl]carbonyl]-N-[3,4-(diphenylmethoxy)phenyl]glycine, phenylmethyl ester Benzyl N-(3,4-dibenzyloxy)phenylglycinate (902 mg, 2.0 mmole) was dissolved in 6 ml of dry toluene and cooled to 0° C. A phosgene solution (2.9 ml of 12.5% in toluene, 3.4 mmole) was added to the reaction mixture followed by the dropwise addition of pyridine (0.348 ml, 4.3 mmole) with rapid stirring. The reaction mixture was stirred for 1.5 hours at 0° C. and then allowed to warm to room temperature. The precipitate of pyridinium hydrochloride was filtered under argon, and the volatiles were removed from the filtrate. This was dissolved in 4 ml of dry tetrahydrofuran and cooled to 0° C. To this solution was added the (S)-3-[[(phenylmethoxy)carbonyl]amino]-2-azetidinone (440 mg, 2.0 mmole) and dimethylaminopyridine (36 mg, 0.3 mmol). Triethylamine (0.307 ml, 2.2 mmole) was then added dropwise, and the reaction mixture was allowed to warm to room temperature and stir overnight. The product was extracted from dilute aqueous hydrochloric acid with three portions of ethyl acetate. The combined organic extracts were dried with sodium sulfate, filtered, and the volatiles removed. The residue was purified by flash chromatography on silica (LPS-1) (eluting with 55% ethyl acetate/hexane) to yield 500 mg of the title compound.

(C)
[3S-[3α(Z),4β]]-N-[[3-[[(2-Amino-4-thiazolyl)(methoxyimino)acetyl]amino]-2-oxo-1-azetidinyl]carbonyl]-N-(3,4-dihydroxyphenyl)glycine, potassium salt N-Hydroxybenzotriazole hydrate (127 mg, 0.936 mmole) and 193 mg (0.936 mmole) of (Z)-2-amino-α-(methoxyimino)-4-thiazoleacetic acid (containing 0.15 molar equivalents of methanol were dissolved in 3.4 ml of dimethylformamide and cooled to 0° C. N,N-Dicyclohexylcarbodiimide (193 mg, 0.936 mmole) was added, and the mixture was warmed to room temperature. The reaction mixture was stirred for 30 minutes to yield the N-hydroxybenzotriazole ester.

Benzyl N-(3,4-dibenzyloxy)phenylglycinate (543 mg, 0.78 mmole) was dissolved in 3.4 ml of dimethylformamide and 148 mg (0.78 mmole) of p-toluenesulfonic acid monohydrate was added. Hydrogenolysis of the protecting groups at room temperature over 272 mg of 10% palladium on charcoal was complete after 45 minutes. The reaction mixture was placed under nitrogen and cooled to 0° C. Diisopropylethylamine (0.447 ml, 2.57 mmole) was then added to the azetidinone immediately followed by the N-hydroxybenzotriazole ester, and the resulting mixture was stirred at 5° C. overnight.

The reaction mixture was filtered to remove the palladium on charcoal and the dicyclohexylurea precipitate, and the volatiles were removed under vacuum. The residue was suspended in ~3 ml of water at 0° C., and the pH was adjusted to 6.5 with aqueous potassium bicarbonate. Acetone (~2 ml) was added, and the resulting solution was subjected to column chromatography with water on Dowex 50X2-400 resin (K+ form) to yield impure title compound. The crude product was dissolved in ~3 ml of water at 0° C. and the pH was readjusted to 6.5 with 1N hydrochloric acid. Purification of this solution by column chromatography on HP-20 (eluting with water, and 5% acetone/water) yielded, upon lyophilization, 66 mg of the title compound, melting point 165°-170° C., dec.

Anal. Calc'd. for $C_{18}H_{17}N_6O_8SK.1.80H_2O$: C, 39.39; H, 3.76; N, 15.32; K, 7.11. Found: C, 39.39; H, 3.96; N, 14.84; K, 7.11.

What is claimed is:
1. A compound having the formula

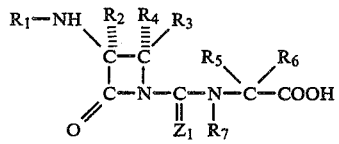

or a pharmaceutically acceptable ester or salt thereof, wherein $Z_1$ is oxygen or sulfur;

$R_1$ is an acyl group derived from a carboxylic acid;

$R_2$ is hydrogen or methoxy;

$R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, carboxy, —CH$_2$X$_1$, —S—X$_2$, —O—X$_2$,

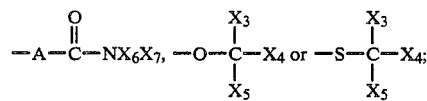

wherein $X_1$ is azido, amino, hydroxy, carboxy, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano, —S—X$_2$ or —O—X$_2$; X$_2$ is alkyl, phenyl, or substituted phenyl; one of X$_3$ and X$_4$ is hydrogen and the other is hydrogen or alkyl, or X$_3$ and X$_4$ when taken together with the carbon atom to which they are attached form a cycloalkyl group; X$_5$ is formyl, alkanoyl, phenylcarbonyl, (substituted phenyl)carbonyl, phenylalkylcarbonyl, (substituted phenyl)alkylcarbonyl, carboxy, alkoxycarbonyl, aminocarbonyl, (substituted amino)carbonyl, or cyano; A is —CH=CH—, —(CH$_2$)$_n$—, —CH$_2$—O—, —CH$_2$—NH—, —CH$_2$—S—CH$_2$— or —CH$_2$—O—CH$_2$—; n is 0, 1 or 2; and X$_6$ and X$_7$ are the same or different and each is hydrogen, alkyl, phenyl or substituted phenyl, or X$_6$ is hydrogen and X$_7$ is amino, substituted amino, alkanoylamino or alkoxy, or X$_6$ and X$_7$ when taken together with the nitrogen atom to which they are attached form a 4, 5, or 6-membered nitrogen containing heterocycle;

R$_5$ and R$_6$ are the same or different and each is hydrogen, alkyl, alkenyl, alkynyl, phenyl, substituted phenyl, cycloalkyl or a 4, 5, 6 or 7-membered heterocycle, or R$_5$ and R$_6$ together with the carbon atom to which they are attached are cycloalkyl, or one of R$_5$ and R$_6$ is hydrogen and the other is halomethyl, dihalomethyl, trihalomethyl, alkoxycarbonyl, alkenyl, alkynyl, 2-phenylethenyl, 2-phenylethynyl, carboxy, —CH$_2$—X$_1$, or

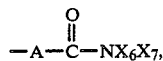

or R$_6$ is hydrogen and R$_5$ together with R$_7$ and the atoms to which they are attached form a 4, 5, or 6-membered nitrogen containing heterocycle; and R$_7$ is hydrogen, alkyl, phenyl, substituted phenyl, cycloalkyl, a 4, 5, 6 or 7-membered heterocycle,

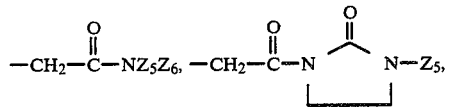

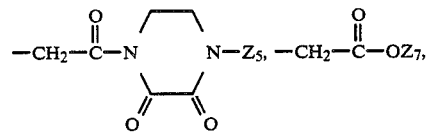

or —(CH$_2$)$_n$—Z$_3$ wherein n is 2, 3 or 4 and Z$_3$ is azido, —NZ$_5$Z$_6$, halogen, hydroxy,

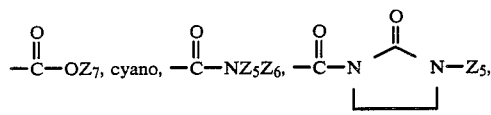

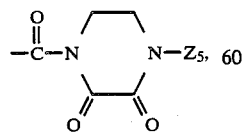

alkanoyloxy, alkoxy, phenyloxy, (substituted phenyl)oxy, (a 4, 5, 6 or 7-membered heterocycle)—O—, mercapto, alkylthio, phenylthio, (substituted phenyl)thio, alkylsulfinyl, alkylsulfonyl,

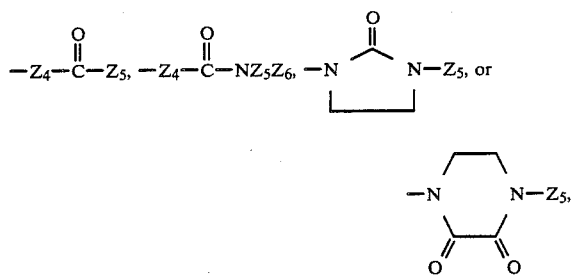

wherein Z$_4$ is oxygen, sulfur or

Z$_5$ is hydrogen, alkyl, phenyl, substituted phenyl, phenylalkyl or (substituted phenyl)alkyl, Z$_6$ is hydrogen, alkyl, phenyl, substituted phenyl, phenylalkyl, (substituted phenyl)alkyl, alkanoyl, phenylcarbonyl, or (substituted phenyl)carbonyl, and Z$_7$ is hydrogen, alkyl, phenyl or substituted phenyl;

wherein the terms "alkyl" and "alkoxy" refer to groups having 1 to 10 carbon atoms;

the term "cycloalkyl" refers to groups having 3, 4, 5, 6 or 7 carbon atoms;

the term "substituted alkyl" refers to alkyl groups substituted with one, or more, azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the terms "alkanoyl", "alkenyl", and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms), alkanoyloxy, aminocarbonyl or carboxy groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolidinyl, oxazolidinyl, pyrrolidinyl, tetrahydropyrimidinyl, dihydrothiazolyl, hexahydroazepinyl, or one of the above groups substituted with one, or more, oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl, wherein the alkyl group has 1 to 4 carbon atoms, groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one, or more, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl, wherein the alkyl group has 1 to 4 carbon atoms, groups;

the term "substituted amino" refers to a group having the formula —NZ$_8$Z$_9$ wherein Z$_8$ is hydrogen, alkyl, phenyl, substituted phenyl, phenylalkyl or (substituted phenyl)alkyl and Z$_9$ is alkyl, phenyl, substituted phenyl, phenylalkyl, (substituted phenyl)alkyl, hydroxy, cyano, alkoxy, phenylalkoxy, or amino;

the expression "a 4, 5, or 6-membered nitrogen containing heterocycle" refers to 1-pyrrolidinyl, Δ$^3$-pyrrolin-1-yl, 1-azetidinyl, 1-piperidinyl, Δ$^3$-piperidein-1-yl, Δ$^4$-piperidein-1-yl, 3-oxazolidinyl, 3-thiazolidinyl, 1-imidazolidinyl, 4-thiomorpholinyl, 4-morpholinyl, 1-piperazinyl, 1-hexahydroopyrimidinyl, tetrahydro-2H-1,3-thiazin-3-yl, tetrahydro-2H-1,3-oxazin-3-yl, 3-thiazolidinyl,-1-oxide, 3-thiazolidinyl,1,1-dioxide, 4-thiomorpholinyl,1-oxide, 4-thiomorpholinyl,1,1-dioxide, tetrahydro-2H-1,3-thiazin-3-yl,1-oxide, tetrahydro-2H-1,3-thiazin-3-yl,1,1-dioxide, or one of the above groups substituted with one, or more, oxo, halogen, hydroxy, amino, cyano, trifluoromethyl, alkyl of 1 to 4 carbon atoms, alkoxy of 1 to 4 carbon atoms, alkylsulfonyl, phenyl, substituted phenyl, azido, carboxy, aminocarbonyl, OZ$_{10}$, NHZ$_{10}$, or SZ$_{10}$ groups where Z$_{10}$ is alkanoyl, aminocarbonyl, aminosulfonyl, phenylcarbonyl, (substituted phenyl)carbonyl, alkyl, substituted alkyl, phenyl or substituted phenyl.

2. A compound in accordance with claim 1 wherein Z$_1$ is oxygen and R$_2$ is hydrogen.

3. A compound in accordance with claim 2 wherein R$_7$ is hydrogen.

4. A compound in accordance with claim 2 wherein R$_7$ is alkyl.

5. A compound in accordance with claim 2 wherein R$_7$ is phenyl or substituted phenyl.

6. A compound in accordance with claim 2 wherein R$_7$ is —(CH$_2$)$_n$—Z$_3$.

7. A compound in accordance with claim 2 wherein R$_3$, R$_4$, R$_5$ and R$_6$ are each independently hydrogen or methyl.

8. A compound in accordance with claim 2 wherein R$_3$, R$_4$, R$_5$ and R$_6$ are each hydrogen.

9. A compound in accordance with claim 1 wherein R$_1$ is

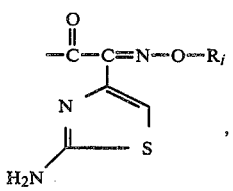

and R$_i$ is methyl, ethyl, carboxymethyl, 1-carboxy-1-methylethyl, 2,2,2-trifluoroethyl or 1-carboxycyclopropyl.

10. A compound in accordance with claim 2 wherein R$_1$ is

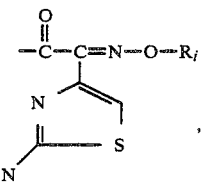

and R$_i$ is methyl, ethyl, carboxymethyl, 1-carboxy-1-methylethyl, 2,2,2-trifluoroethyl or 1-carboxycyclopropyl.

11. A compound in accordance with claim 1 having the formula

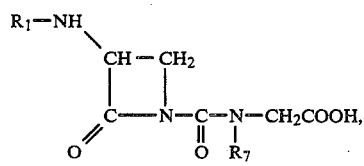

or a pharmaceutically acceptable ester or salt thereof, wherein R$_1$ is an acyl group derived from a carboxylic acid and R$_7$ is methyl or ethyl.

12. A compound in accordance with claim 11 wherein R$_1$ is

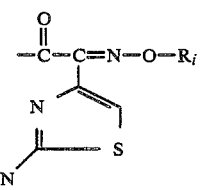

and R$_i$ is methyl, ethyl, carboxymethyl, 1-carboxy-1-methylethyl, 2,2,2-trifluoroethyl or 1-carboxycyclopropyl.

13. A compound in accordance with claim 1 having the formula

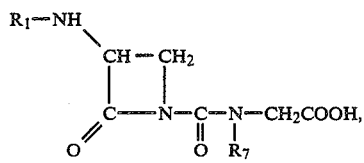

or a pharmaceutically acceptable ester or salt thereof, wherein R$_1$ is an acyl group derived from a carboxylic acid and R$_7$ is phenyl or substituted phenyl.

14. A compound in accordance with claim 13 wherein R$_1$ is

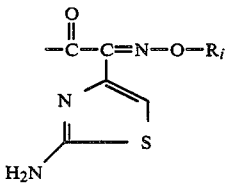

and R*i* is methyl, ethyl, carboxymethyl, 1-carboxy-1-methylethyl, 2,2,2-trifluoroethyl or 1-carboxycyclopropyl.

15. A compound in accordance with claim 1 having the formula

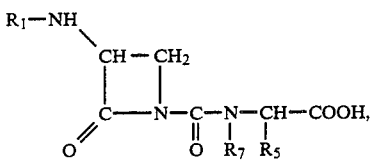

or a pharmaceutically acceptable ester or salt thereof, wherein $R_1$ is an acyl group derived from a carboxylic acid and $R_5$ together with $R_7$ and the atoms to which they are attached form a 4, 5, or 6-membered nitrogen containing heterocycle.

16. A compound in accordance with claim 15 wherein $R_5$ together with $R_7$ and the atoms to which they are attached are pyrrolidinyl or pyrrolidinyl substituted in the 4-position with halogen, hydroxy, aminocarbonyloxy, aminocarbonylamino, or aminosulfonylamino.

17. A compound in accordance with claim 15 wherein $R_5$ together with $R_7$ and the atoms to which they are attached are azetidinyl or azetidinyl substituted in the 3-position with halogen, hydroxy, aminocarbonyloxy, aminocarbonylamino, or aminosulfonylamino.

18. A compound in accordance with claim 15 wherein $R_1$ is

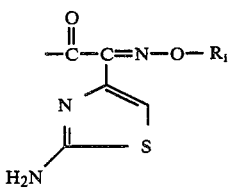

and R*i* is methyl, ethyl, carboxymethyl, 1-carboxy-1-methylethyl, 2,2,2-trifluoroethyl or 1-carboxycyclopropyl.

19. A compound in accordance with claim 16 wherein $R_1$ is

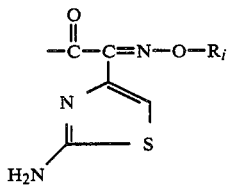

and R*i* is methyl, ethyl, carboxymethyl, 1-carboxy-1-methylethyl, 2,2,2-trifluoroethyl or 1-carboxycyclopropyl.

20. A compound in accordance with claim 17 wherein R*i* is

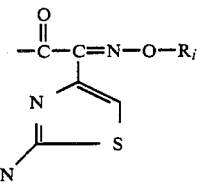

and R*i* is methyl, ethyl, carboxymethyl, 1-carboxy-1-methylethyl, 2,2,2-trifluoroethyl or 1-carboxycyclopropyl.

21. The compound in accordance with claim 1, [3S(Z)]-1-[[3-[[(2-amino-4-thiazolyl)(methoxyimino)acetyl]amino]-2-oxo-1-azetidinyl]carbonyl]-L-proline, or a pharmaceutically acceptable salt thereof.

22. The compound in accordance with claim 1, [3S(Z)]-1-[[3-[[(2-amino-4-thiazolyl)[(1-carboxy-1-methylethoxy)imino]acetyl]amino]-2-oxo-1-azetidinyl]carbonyl]-L-proline, or a pharmaceutically acceptable salt thereof.

23. The compound in accordance with claim 1, (trans)-1-[[3S(Z)]-[3-[[(2-amino-4-thiazolyl)(methoxyimino)acetyl]amino]-2-oxo-1-azetidinyl]carbonyl]-4-hydroxy-L-proline, or a pharmaceutically acceptable salt thereof.

24. The compound in accordance with claim 1, (S)-1-[[3S(Z)]-[3-[[(2-amino-4-thiazolyl)(methoxyimino)acetyl]amino]-2-oxo-1-azetidinyl]carbonyl]-2-azetidinecarboxylic acid, or a pharmaceutically acceptable salt thereof.

25. The compound in accordance with claim 1, (S)-1-[[(S)-3-[(Z)-[(2-amino-4-thiazolyl)-[(carboxymethoxy)imino]acetyl]amino]-2-oxo-1-azetidinyl]carbonyl]-2-azetidinecarboxylic acid, or a pharmaceutically acceptable salt thereof.

26. The compound in accordance with claim 1, (S)-1-[[(S)-3-[[(Z)-(2-amino-4-thiazolyl)[(1-carboxy-1-methylethoxy)imino]acetyl]amino]-2-oxo-1-azetidinyl]carbonyl]-2-azetidinecarboxylic acid, or a pharmaceutically acceptable salt thereof.

27. The compound in accordance with claim 1, [3S(Z)]-N-[[3-[[(2-amino-4-thiazolyl)(methoxyimino)acetyl]amino]-2-oxo-1-azetidinyl]carbonyl]-N-(4-hydroxyphenyl)glycine, or a pharmaceutically acceptable salt thereof.

28. The compound in accordance with claim 1, (R)-4-[(aminocarbonyl)oxy]-1-[[(S)-3-[[(2-amino-4-thiazolyl)-(methoxyimino)acetyl]amino]-2-oxo-1-azetidinyl]carbonyl]-L-proline, or a pharmaceutically acceptable salt thereof.

29. The compound in accordance with claim 1, [3S(Z)]-2-[[[1-(2-amino-4-thiazolyl)-2-[[1-[[(carboxymethyl)methylamino]carbonyl]-2-oxo-3-azetidinyl]amino]-2-oxoethylidene]amino]oxy]-2-methylpropanoic acid, or a pharmaceutically acceptable salt thereof.

30. The compound in accordance with claim 1, [3S(Z)]-[N-[[3-[[(2-amino-4-thiazolyl)(methoxyimino)acetyl]amino]-2-oxo-1-azetidinyl]carbonyl]methylamino]acetic acid, or a pharmaceutically acceptable salt thereof.

31. The compound in accordance with claim 1, [3S(Z)]-N-[[3-[[(2-amino-4-thiazolyl)(methoxyimino)acetyl]amino]-2-oxo-1-azetidinyl]carbonyl]-N-ethylglycine, or a pharmaceutically acceptable salt thereof.

32. A compound having the formula

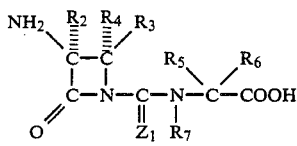

or a salt thereof, or a carboxy protected derivative thereof, wherein
$Z_1$ is oxygen or sulfur;
$R_2$ is hydrogen or methoxy;
$R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, carboxy, —$CH_2X_1$, —S—$X_2$, —O—$X_2$,

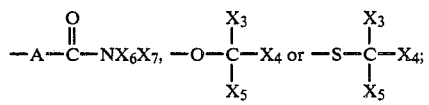

wherein $X_1$ is azido, amino, hydroxy, carboxy, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano, —S—$X_2$ or —O—$X_2$; $X_2$ is alkyl, phenyl, or substituted phenyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxy, alkoxycarbonyl, aminocarbonyl, (substituted amino)carbonyl, or cyano; A is —CH=CH—, —$(CH_2)_n$—, —$CH_2$—O—, —$CH_2$—NH—, —$CH_2$—S—$CH_2$— or —$CH_2$—O—$CH_2$—; n is 0, 1 or 2; and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, or 6-membered nitrogen containing heterocycle;

$R_5$ and $R_6$ are the same or different and each is hydrogen, alkyl, alkenyl, alkynyl, phenyl, substituted phenyl, cycloalkyl or a 4, 5, 6 or 7-membered heterocycle, or $R_5$ and $R_6$ together with the carbon atom to which they are attached are cycloalkyl, or one of $R_5$ and $R_6$ is hydrogen and the other is halomethyl, dihalomethyl, trihalomethyl, alkoxycarbonyl, alkenyl, alkynyl, 2-phenylethenyl, 2-phenylethynyl, carboxy, —$CH_2$—$X_1$, or

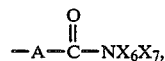

or $R_6$ is hydrogen and $R_5$ together with $R_7$ and the atoms to which they are attached form a 4, 5, or 6-membered nitrogen containing heterocycle; and
$R_7$ is hydrogen, alkyl, phenyl, substituted phenyl, cycloalkyl, a 4, 5, 6 or 7-membered heterocycle,

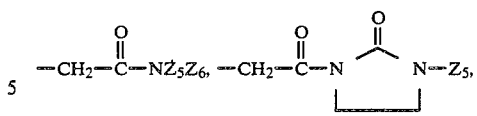

or —$(CH_2)_n$—$Z_3$ wherein n is 2, 3 or 4 and $Z_3$ is azido, —$NZ_5Z_6$, halogen, hydroxy,

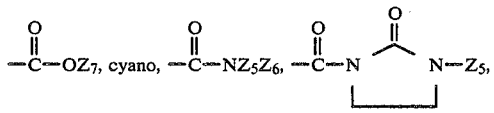

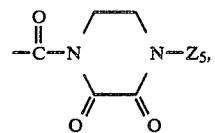

alkanoyloxy, alkoxy, phenyloxy, (substituted phenyl)oxy, (a 4, 5, 6 or 7-membered heterocycle)—O—, mercapto, alkhylthio, phenylthio, (substituted phenyl)thio, alkylsulfinyl, alkylsulfonyl,

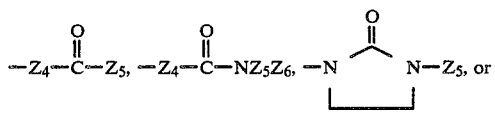

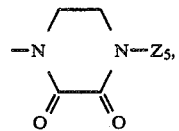

wherein $Z_4$ is oxygen, sulfur or

$Z_5$ is hydrogen, alkyl, phenyl, substituted phenyl, phenylalkyl or (substituted phenyl)alkyl, $Z_6$ is hydrogen, alkyl, phenyl, substituted phenyl, phenylalkyl, (substituted phenyl)alkyl, alkanoyl, phenylcarbonyl, or (substituted phenyl)carbonyl, and $Z_7$ is hydrogen, alkyl, phenyl or substituted phenyl;
wherein the terms "alkyl" and "alkoxy" refer to groups having 1 to 10 carbon atoms;
the term "cycloalkyl" refers to groups having 3, 4, 5, 6 or 7 carbon atoms;
the term "substituted alkyl" refers to alkyl groups substituted with one, or more, azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

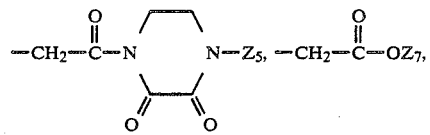

the terms "alkanoyl", "alkenyl", and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl (of 1 to 4 carbon atom), alkoxy (of 1 to 4 carbon atoms), alkanoyloxy, aminocarbonyl or carboxy groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolidinyl, oxazolidinyl, pyrrolidinyl, tetrahydropyrimidinyl, dihydrothiazolyl, hexahydroazepinyl, or one of the above groups substituted with one, or more, oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl, wherein the alkyl groups has 1 to 4 carbon atoms, groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one, or more, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl, wherein the alkyl group has 1 to 4 carbon atoms, groups;

the term "substituted amino" refers to a group having the formula $-NZ_8Z_9$ wherein $Z_8$ is hydrogen, alkyl, phenyl, substituted phenyl, phenylalkyl or (substituted phenyl)alkyl and $Z_9$ is alkyl, phenyl, substituted phenyl, phenylalkyl, (substituted phenyl)alkyl, hydroxy, cyano, alkoxy, phenylalkoxy, or amino;

the expression "a 4, 5, or 6-membered nitrogen containing heterocycle" refers to 1-pyrrolidinyl, $\Delta^3$-pyrrolin-1-yl, 1-azetidinyl, 1-piperidinyl, $\Delta^3$-piperidein-1-yl, $\Delta^4$-piperidein-1-yl, 3-oxazolidinyl, 3-thiazolidinyl, 1-imidazolidinyl, 4-thiomorpholinyl, 4-morpholinyl, 1-piperazinyl, 1-hexahydropyrimidinyl, tetrahydro-2H-1,3-thiazin-3-yl, tetrahydro-2H-1,3-oxazin-3-yl, 3-thiazolidinyl,-1-oxide, 3-thiazolidinyl,1,1-dioxide, 4-thiomorpholinyl,1-oxide, 4-thiomorpholinyl,1,1-dioxide, tetrahydro-2H-1,3-thiazin-3-yl,1-oxide, tetrahydro-2H-1,3-thiazin-3-yl,1,1-dioxide, or one of the above groups substituted with one, or more, oxo, halogen, hydroxy, amino, cyano, trifluoromethyl, alkyl of 1 to 4 carbon atoms, alkoxy of 1 to 4 carbon atoms, alkylsulfonyl, phenyl, substituted phenyl, azido, carboxy, aminocarbonyl, $OZ_{10}$, $NHZ_{10}$, or $SZ_{10}$ groups where $Z_{10}$ is alkanoyl, aminocarbonyl, aminosulfonyl, phenylcarbonyl, (substituted phenyl)carbonyl, alkyl, substituted alkyl, phenyl or substituted phenyl.

* * * * *